Figure 1:
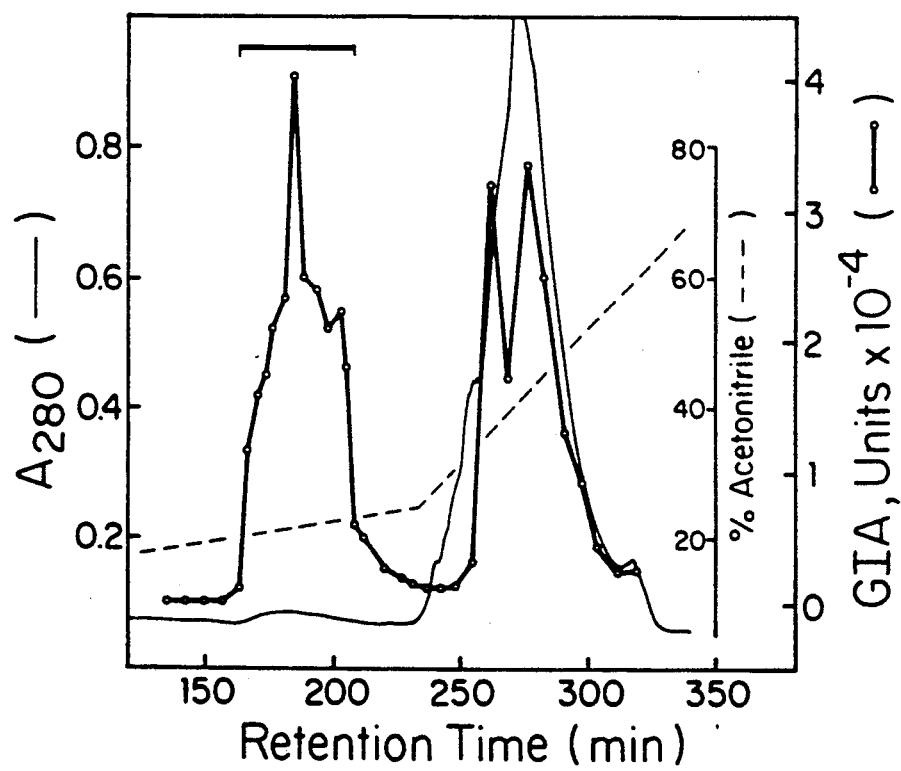

United States Patent [19]

Shoyab et al.

[11] Patent Number: 5,115,096

[45] Date of Patent: May 19, 1992

[54] AMPHIREGULIN: A BIFUNCTIONAL GROWTH MODULATING GLYCOPROTEIN

[75] Inventors: Mohammed Shoyab, Seattle; Vicki L. McDonald, Kent; James G. Bradley, Woodinville; Gregory D. Plowman, Seattle, all of Wash.

[73] Assignee: Oncogen, Seattle, Wash.

[21] Appl. No.: 297,816

[22] Filed: Jan. 17, 1989

Related U.S. Application Data

[63] Continuation-in-part of Ser. No. 181,884, Apr. 15, 1988, abandoned, which is a continuation-in-part of Ser. No. 148,327, Jan. 25, 1988, abandoned.

[51] Int. Cl.$^5$ ............................................. C07K 9/00
[52] U.S. Cl. ................................... 530/322; 530/324
[58] Field of Search ........................................ 530/322

[56] References Cited

PUBLICATIONS

Shoyab et al. (1988), *Proc. Natl. Acad. Sci., U.S.A.*, 85, 6526–6532.
Shoyab et al. (1989), *Science*, 243, 1074–1076.

*Primary Examiner*—Douglas W. Robinson
*Assistant Examiner*—Jon Weber
*Attorney, Agent, or Firm*—Pennie & Edmonds

[57] ABSTRACT

A novel cell growth regulatory factor, named Amphiregulin, is described. This extremely hydrophilic glycoprotein, having a median molecular weight of 22,500 daltons, demonstrates unusual biological activity. Amphiregulin is a bifunctional cell growth regulatory factor which exhibits potent inhibitory activity on DNA synthesis in neoplastic cells, yet promotes the growth of certain normal cells. The invention is based, in part, on the discovery that MCF-7 cells, when treated with the tumor promoting agent, 12-O-tetradecanoyl-phorbol-13-acetate (TPA), express and secrete two distinct yet functionally equivalent forms of Amphiregulin. These two forms are structurally identical and perfectly homologous except that the truncated form lacks an amino-terminal hexapeptide found in the larger form. The Amphiregulin gene has been cloned and used to construct plasmids which direct the expression of bioactive Amphiregulin in transformed *Escherichia coli* cells. A wide variety of uses for Amphiregulin are encompassed by the present invention, including the treatment of wounds and cancers.

23 Claims, 35 Drawing Sheets

```
       1                  10                    20
       V V K P P Q D K T E  S E N T S D K P K R  K K K G G K N G K 30                 40                    50
       N  R R N R K K N P C  N A E F Q N F C I H  G E C K Y I 60                 70                     78
       E H L E  A V T C K C Q Q E Y  F G E R C G E K
```

IEF

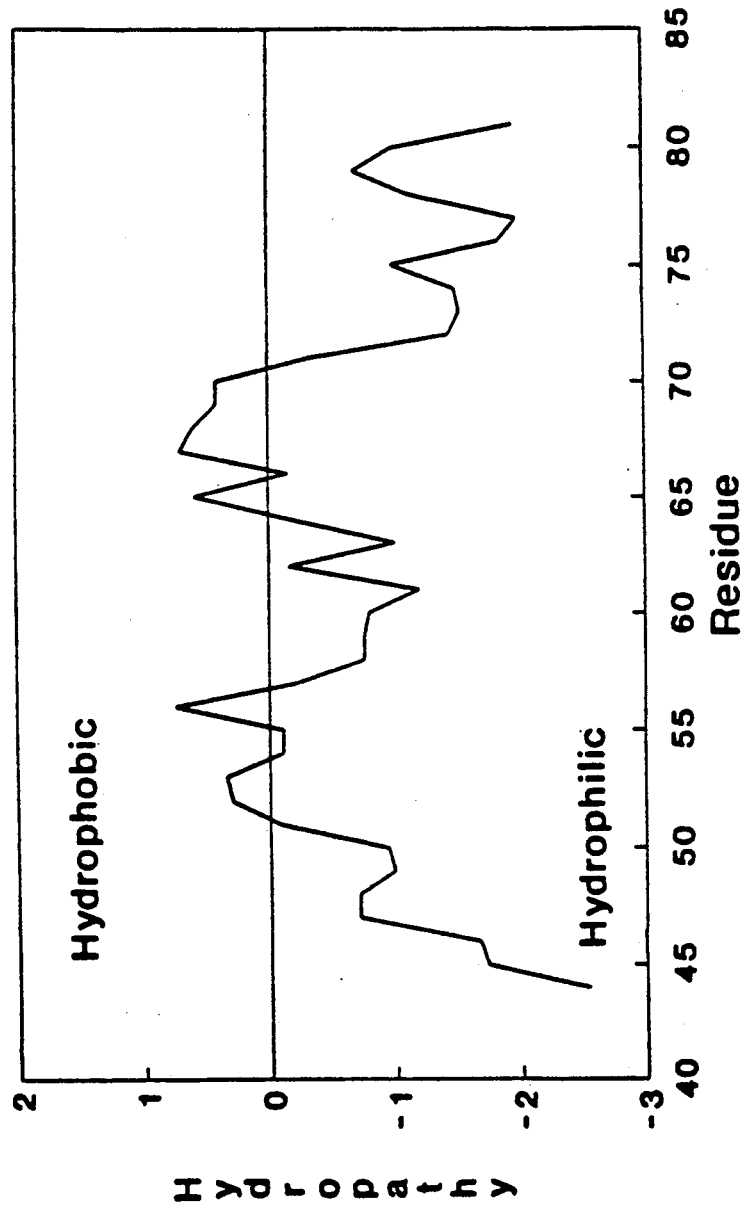
FIG. 11B Human AR - EGF-like Domain Hydropathy

| EGF Superfamily | | 1 | 5 | 10 | 15 | 20 | 25 | 30 | 35 | 40 | 45 |
|---|---|---|---|---|---|---|---|---|---|---|---|
| AR | Human | C | N A E F | Q N F C | I H - G E | C K Y I E H L E A V T | C K P A | C Q Q | E Y F G E R | C G E H | S M K T H S |
| TGF-α | Human | C | P D S H T | Q F C F | H - G T C | R F L V Q E E D K P A | C V C H | S G Y V G A R | C E H A D | L L A V V |
| TGF-α | Rat | C | P D S H T | Q Y C F | H - G T C | R F L V Q E D K P A | C V C H | S G Y V G V R | C E H A D | L L A V V |
| EGF | Human | C | P L S H D | G Y C L | H D G V C | M Y I E A L D K Y A | C N C V | V G Y I G E R | C Q Y R D | L K W W E |
| EGE | Mouse | C | P S S Y D | G Y C L | N G G V C | M H I E S L D S Y T | C N C V | I G Y S G D R | C Q T R D | L R W W E |
| VGF | Viral | C | P P E Y D | G Y C L | N G G V C | M H A R D I D P Y A | C N C V | I G Y S G D R | C Q T R D | L R W Y E |
| SFGF | Viral | C | G P N Z N | D Y K C | - - - - - | F F T (IALDNVSIT) P F | P F C | N Y V G H N | C Q F V D | L V T Y * |
| MGF | Viral | C | G P N Z N | D Y K C | - - - - - | F F T (VALNVSLN) P F | P F C | N Y V G S R | C Q F I N | L I T I K * |

| Notch | Fly | C | - - - - - | - - - - - | - - - - - | - Q L K T L E E Y T | C A C A | N G Y T G E R | C E T K N L | C A S S |
| Lin-12 | Nematode | C | - - - - - | - Q D F H | - - - - - | - M H T S D H S P V | C Q C P | V G F I G K R | C E K E C P | I G F G |
| EGF | Urchin | C | - - - - - | - A S L P | - - - - - | - I D G I A G Y T | C A C Q | R L G Y T G V N | C E D L |

| Protein Z | Bovine | C | - - - - - | - A S Q P | C L L N G G T C | - Q D S I R G Y A | C T C A | P G Y E G G | C A F A E S E C H P |
| Factor XII | Human | C | - - - - - | - R T E S | C P N P G G T C | - L E V E G H R L | C P C P | V G G Y T G P | C R V D T K A S C Y |
| Factor X | Human | C | - - - - - | - E S N P | C L N G G S C | - K D D I N S Y E | C W C P | F G F E G K N | C E L D V T C N I K S |
| Factor IX | Human | C | - - - - - | - A S L P | C L N G G S C | - I D G I G K A S | C T C G | E G G Y W E G R | C E L D V T R A T C Y |
| Protein C | Human | C | - - - - - | - S P L P | C N E D G C | - C Y H S Q L Y F S D | C W C P | W Q G E F C Q | C Q R F L N C D |
| Protein S | Human | C | - - - - - | - S E P R | C P R G G C | - I D G I G Y E | C A G L | V A Q R E F F D | C R E V R R |
| tPA | Human | C | - - - - - | - L D N N | G G C - - - | - I Q A L - - - | C V C P | P G Y I G S R | C D D C A S G Y F G |
| LDL Recep. | Human | C | - - - - - | - L P | - - - - - | - V Q D P V T L Q L A | C V C | D P T G Y I G K N | C E C Q T Q G R S S |

| Laminin | Human | C P D G P D S G | R Q F A R S | C Y Q D P V T L Q L A | H G K G F L E C G I |
| LAP | Human | C E C R C | R D Q S R D R S L | C H |

| | | 50 | 55 | 60 | 65 | 70 | 75 | 80 |
|---|---|---|---|---|---|---|---|---|
| | | M I D S S L S K - | I A L A A I A A F H S A V - | I L T A V A V I T V Q L R R |
| | | A A S Q K K R H A G G Q Q | K Q A I T A L V V S I V A L A V | L I I T C V L I I H C C Q V R K |
| | | A A S Q K K R H A G G Q Q | K Q A I T A L V V S I V A L A V | L I I T C V L I H C C Q V R K |
| | | L R H A G Y G Q Q K H D I M | Y V A V C M V A L V L V G | I I I T C C L L S V Y R F |
| | | R S E N P N T T T S Y I P S P G I M | L V L V G | |

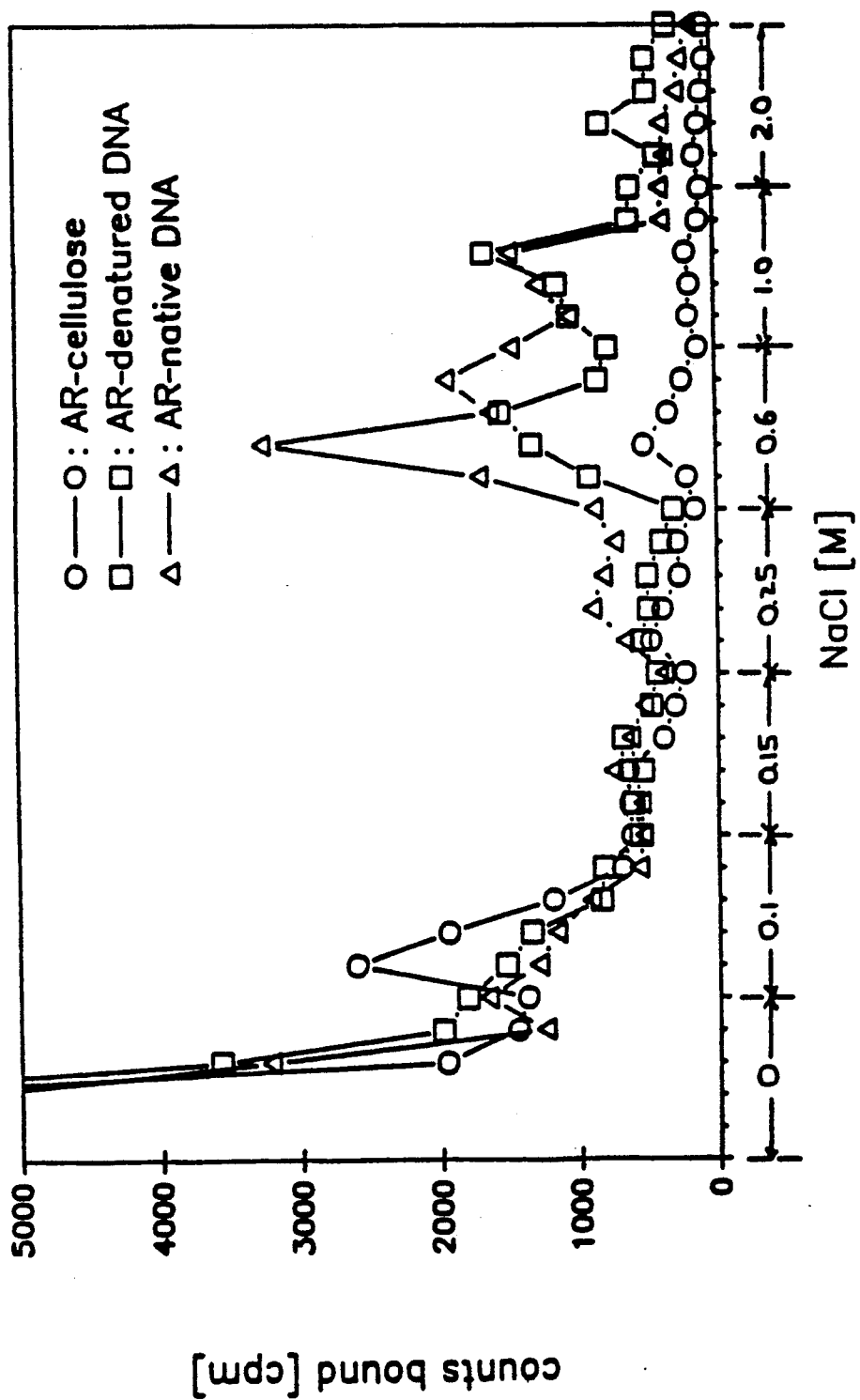

Amphiregulin Precursor

```
MRAPLLPPAP VVLSLLILGS GHYAAGLDLN DTYSGKREPF SGDHSADGFE   50
VTSRSEMSSG SEISPVSEMP SSSEPSSGAD YDYSEEYDNE PQIPGYIVDD  100
SVRVEQVVKP PQNKTESENT SDKPKRKKKG GKNGKNRRNR KKKNPCNAEF  150
QNFCIHGECK YIEHLEAVTC KCQQEYFGER CGEKSMKTHS MIDSSLSKIA  200
LAAIAAFMSA VILTAVAVIT VQLRRQYVRK YEGEAEERKK LRQENGNVHA  250
IA                                                     252
```

Mature Amphiregulin

```
         ↓
SVRVEQVVKP PQNKTESENT SDKPKRKKKG GKNGKNRRNR KKKNPCNAFF
QNFCIHGECK YIEHLEAVTC KCQQEYFGER CGEK
```

| Peptide | Residue | Length | Region |
|---|---|---|---|
| 259 | 166–184 EAVTCKCQQEYFGERCGEK | 19 | EGF-like |
| 264 | 108–130 VKPPQNKTESENTSDKPKRKKKG | 23 | Hydrophilic |
| 279 | 31–50 DTYSGKREPFSGDHSADGFE | 20 | N-Terminal #1 |
| 280 | 71–90 SSSEPSSGADYDYSEEYDNE | 20 | N-Terminal #2 |
| 281 | 221–240 VQLRRQYVRKYEGEAEERKK | 20 | Cytoplasmic |

*FIG. 15*

Human Amphiregulin cDNA Sequence

```
   1  AGACGTTCGCACACCTGGGTGCCAGGCGCCCCAGAGGTCCGGGACAGCCCGAGGCGCCGCCCCGAGCTCCCCAAGCCTTCGAGAGCGGCGC
 101  ACACTCCGGTCTCCACTGCTCTTCCAACACCCGCTCGTTTTGCGGCAGCTCGTGTCCCAGAGACCGAGTTGCCCCAGAGACCGAGACGCGCCGCTGC
                                                         1                  10                     20
                                                         M   R   A   P   L   L   P   P   A   P   V   V   L   S   L   L   L   G   S   H
 201  GAAGGACCA                                       ATG AGA GCC CCG CTG CTA CCG CCG GCG CCG GTG GTG CTG TCG CTC TTG CTA GGC TCA CAT
                                                                             30
       Y   A   A   G   L   D   L   N   D   T   Y   S   G   K   R   E   P   F   S   G   D   H   S   A   D
 276  TAT GCT GCT GGA TTG GAC CTC AAT GAC ACC TAC TCT GGG AAG CGT GAA CCA TTT TCT GGG GAC CAC AGT GCT GAT
           50                                                        60                            70
       G   F   E   V   T   S   R   S   E   M   S   S   G   S   E   I   S   P   V   S   E   M   P   S   S
 351  GGA TTT GAG GTT ACC TCA AGA AGT GAG ATG AGT TCT GGG AGT GAG ATT TCC CCT GTG AGT GAA ATG CCT TCT AGT
                                                                                                   90
       S   E   P   S   S   G   A   D   Y   D   Y   S   E   E   Y   D   N   E   P   Q   I   P   G   Y   I
 426  AGT GAA CCG TCC TCG GGA GCC GAC TAT GAC TAC TCA GAA GAG TAT GAT AAC GAA CCA CAA ATA CCT GGC TAT ATT
                    100                                                           110                                 120
       V   D   D   S   V   R   V   E   Q   V   V   K   P   P   Q   N   K   T   E   S   E   N   T   S   D
 501  GTC GAT GAT TCA GTC AGA GTT GAA CAG GTA GTT AAG CCC CCC CAA AAC AAG ACG GAA AGT GAA AAT ACT TCA GAT
                                                    130                                          140
       K   P   K   R   K   K   K   G   G   K   N   G   K   N   R   R   N   R   K   K   K   N   P   C   N
 576  AAA CCC AAA AGA AAG AAA AAG GGA GGA AAA AAT GGA AAA AAT AGA AGA AAC AGA AAG AAG AAA AAT CCA TGT AAT
                                        150                                    160                                         170
       A   E   F   Q   N   F   C   I   H   G   E   C   K   Y   I   E   H   L   E   A   V   T   C   K   A
 651  GCA GAA TTT CAA AAT TTC TGC ATT CAC GGC GAA TGC AAA TAT ATA GAG CAC CTG GAA GCA GTA ACA TGC AAA TGT
                                                180                                                           190
       Q   Q   E   F   G   E   R   C   G   E   K   S   M   K   T   H   S   M   I   D   S   S   L   S   S
 726  CAG CAA GAA TAT TTC GGT GAA CGG TGT GGG GAA AAG TCC ATG AAA ACT CAC AGC ATG ATT GAC AGT AGT TTA TCA
                                                                      210                                               220
       K   I   A   A   L   A   A   L   A   A   F   M   S   A   V   I   L   T   A   V   A   V   I   T   V   Q
 801  AAA ATT GCA GCC TTA GCA GCC ATA GCT GCC TTT ATG TCT GCT GTG ATC CTC ACA GCT GTT GCT GTT ATT ACA GTC CAG
                                                                                      230
       L   R   R   Q   Y   V   R   K   Y   E   G   E   A   E   E   R   K   K   L   R   Q   E   N   G   N
 876  CTT AGA AGA CAA TAC GTC AGG AAA TAT GAA GGA GAA GCT GAG GAA CGA AAG AAA CTT CGA CAA GAG AAT GGA AAT
                    250
       V   H   A   I   A
 951  GTA CAT GCT ATA GCA TAACTGAAGATAAAATTACAGGATATCACATTGGAGTCACTGCCAAGTCATAGCCATAAATGATGAGTCGGTCCTCTTC
1046  CAGTGGATCATAAGACAATGGACCCTTTTGTTATGATGGTTTTAAACTTTCAATTGTCACTTTCTGTATATAAGGTGCACGAAGGTA
1146  AAAAGTATTTTTTTCAAGTTGTAAATAATTATTTAATATTTAACCAAAAAAAAAAA
```

FIG. 16

Human Amphiregulin Genomic Sequence

```
 -858  GAATTCATATCCACCTGGCTTTGAACATTATCGGCTGTGAGATGGTGTAGGTAAAATTTAAGTGCATAATTTGGCAATAATAAATCATCAATAAATATT
 -758  AATGTTGATGAGGCCCCTGGGCCACATAAAGAAATAGGGAGTGAGGGATTTGAAATTCTGCCACTTCACAGAAATGGTGGAAGGGCTCTTGATTG
 -658  AGATAGAAGCCCATCTACATGAGCAATTCCTCATTGAGTTCTCTGTCTTTATCCTTGTTGGAAACATCAGGCAAAGTCACTCTTGGTCTTAAAGTA
 -558  CTTTTACATCTAAATACGGAACTCTTCTATTTAATCCGCTCTGTCTGCCCTCTATTTAAGTATACAAAGAGGTTTAAGTTCCATTGCATCTCAGCGAATCATTACGCACA
 -458  TCAGGTACTACGTCCGGAACTCCAGTCCTGCTCGCCCTCAAAAACGGCTTGCAGCTAGAGTTTTAAGTTCCACTGCATCTCAGCGAATCTTACGCACA
 -358  GAGCAGGGCGTGTGTCTCCGGACATAAGTTTCGGTGCAGTTTCCGCACATTGTCGGGCGCGCCCTTCTGGGGCGCCCCTTGCGCCAGCACGTGCG
 -258  GCCCCTCCCGGCTGAGCCTCCGGCCCCCGACCGAGCTCCCCAAGCCTTCCCCAGAGCGGGGCGCGCACTCCGGTCTGCCACTGCGCTCTTCCAACACCCGCTCGTTTGCGGCAGCT
 -158  GGGCGCGCGCCCGCGCCCCGACGTTCCAGACACCGAGCTCCCCAAGCCTTCCCCAGAGCGGGGCGCGCACTCCGGTCTGCCACTGCGCTCTTCCAACACCCGCTCGTTTGCGGCAGCT
```

```
                                                                                                        1                                       10
                                                                                                        M   R   A   P   L   L   P   P   A   P
  -58  CGTGTCCCAGAGACCGAGTTGCCCCAGAGACCGAGACGCCGCGCTGCGAAGGACCAA  ATG AGA GCC CCG CTG CTA CCG CCG GCG CCG

V   V   L   S   L   L   I   L   L   G   S   G
   31  GTG GTG CTG TCG CTC TTG ATA CTC GGC TCA Ggtgaggattcaacggcgctgaactgctgggctctcctcccatggcaggt..(2.1 kb).

H   Y   A   A   G   L   D   L   N   D   T
         ...agcacccctacttttacctttcgttttctttttattcccctcccgcagGC CAT TAT GCT GCT GGA TTG GAC CTC AAT GAC ACC Y   S   G   K   R   E   E   P   F   S   G   D   H   S   A   D   G   F   E   V   T   S   R   S   E   H
   97  TAC TCT GGG AAG CGT GAA GAG CCA TTT TCT GGG GAC CAC AGT GCT GAT GGA TTT GAG GTT ACC TCA AGA AGT GAG ATG S   S   G   S   E   I   S   P   V   S   E   M   P   S   S   S   E   P   S   S   G   A   D   Y   D
  172  TCT TCA GGG AGT GAG ATT TCC CCT GTG AGT GAG ATG CCT TCT AGT GAA CCG TCC TCG GGA GCC GAC TAT GAC Y   S   E   E   Y   D   N   E   P   Q   I   P   G   Y   I   V   D   D   S   V   R   V
  247  TAC TCA GAA GAG TAT GAT AAC GAA CCA CAA ATA CCT GGC TAT ATT GTC GAT GAT TCA GTC AGA Ggtgagtagggataa agcaaaatatggcctgtgagatgtgggtttata..(1.4 kb)..aattatattcaagttgagagacttgtcaataatcttttttttagTI 120
              E   Q   V   V   K   P   P   Q   N   K   T   E   S   E   N   T   S   D   K   P   K   R   K   K   K
  313  GAA CAG GTA GTT AAG CCC CCC CAA AAC AAG ACG GAA AGT GAA AAT ACT TCA GAT AAA CCC AAA AGA AAG AAG
```

FIG. 17

```
                                                                                    150
          130                            140                                                     200
      G   G   K   N   G   K   N   R   R   N   R   K   K   K   N   P   C   N   A   E   F   Q   N   F   C
388   GGA GGC AAA AAT GGA AAA AAT AGA AGA AAC AGA AAG AAG AAA AAT CCA TGT AAT GCA GAA TTT CAA AAT TTC TGC 160                       170                                           gtaagcatatagattttgtattt
      I   H   G   E   C   K   Y   I   E   H   L   E   A   V   T   C   K
463   ATT CAC GGA GAA TGC AAA TAT ATA GAG CAC CTG GAA GCA GTA ACA TGC AgtaagttttcctaaagcatatagattttgcagAA TGT CAG CAA GAA
                                                                                                        C   Q   Q   E ctagcaccatgtctg....(1.25 kb)...cacaccgcacgtgagtgtgattataattttaaatgtgaattgcttgcagAA TGT CAG CAA GAA
                                                              190                                                200
                                                                                                                   A
      Y   F   G   E   R   C   G   G   E   K   S   M   K   T   H   S   M   I   D   S   S   L   S   K   I   A
526   TAT TTC GGT GAA CGG TGT GGG GAA AAG TCC ATG AAA ACT CAC AGC ATG ATT GAC AGT TTA TCA AAA ATT GCA
                                         210                                       220
                                                                                   T   V   Q
      L   A   A   I   A   A   F   M   S   A   V   I   L   T   A   V   A   V   I   T   V   Q
601   TTA GCA GCC ATA GCT GCC TTT ATG TCT GTG ATC CTC ACA GCT GTT GCT ATT ACA GTC CAgtaagtatgacata acttacaaattcttaataaataatgggaggttaat...(2.0 kb)...tatagataatagaaccttgataacattagaatgcctgttctctgaagG
                                                                                      240
      L   R   Q   Y   V   R   K   Y   E   G   G   E   A   E   E   R   K   K   L   R   Q   E   N   G   N
666   CTT AGA AGA CAA TAC GTC AGG AAA TAT GAA GGA GAA GCT GAG GAA CGA AAG AAA CTT CGA CAA GAG AAT GGA AAT
            250
      V   H   A   I   A
742   GTA CAT GCT ATA GCA TAA CTGAAGATAAAATTACAGgtttgagtttaaatatcttttgatcatatccataatttgaaaaatttaac...

..(2.0 kb)...gtaacattttgttttattttattttattttctcacagGATATCACATTGGAGTCACTGCCAAGTCATAGCCATA
      AATGATGAGTCGGTCCTCTTTCCAGTGGATCATAAGACAATGACCCTTTTGTTATGATGGTTTAAACTTTCAATTGTCACTTTTATGCTATTCTG
      TATATAAAGGTGCACGAAGGTAAAAGTATTTTTCAAGTGTAAATAATTAATTGAAGTGTATTTATTTATTTACAGCTCATTAAACTTT
      TTTAACCAAAcaaattgagagtttgaatattggtctgatattgcaagactccagtgtactttctc
```

FIG. 17 CONTINUED

```
NruI                   CMV Enhancer -->
TCGCGATGTACGGGCCAGATATACGCGTTGACATTGATTATTGACTAGTTATTAATAGTAAT

CAATTACGGGGTCATTAGTTCATAGCCCATATATGGAGTTCCGCGTTACATAACTTACGGTA

AATGGCCCGCCTGGCTGACCGCCCAACGACCCCCGCCCATTGACGTCAATAATGACGTATGT

TCCCATAGTAACGCCAATAGGGACTTTCCATTGACGTCAATGGGTGGACTATTTACGGTAAA

NdeI
CTGCCCACTTGGCAGTACATCAAGTGTATCATATGCCAAGTACGCCCCCTATTGACGTCAAT

GACGGTAAATGGCCCGCCTGGCATTATGCCCAGTACATGACCTTATGGGACTTTCCTACTTG

GCAGTACATCTACGTATTAGTCATCGCTATTACCATGGTGATGCGGTTTTGGCAGTACATCA

ATGGGCGTGGATAGCGGTTTGACRCACGGGGATTTCCAAGTCTCCACCCCATTGACGTCAAT

GGGAGTTTGTTTTGGCACCAAAATCAACGGGACTTTCCAAAATGTCGTAACAACTCCGCCCC

EcoRI HIV TATA -->
ATTGACGCAAATGGGCGGAATTCCTGGGCGGGACTGGGGAGTGGCGAGCCCTCAGATGCTGC

ATATAAGCAGCTGCTTTTTGCCTGTACTGGGTCTCTCTGGTTAGACCAGATCTGAGCCTGGG

HindIII   PstI
AGCTCTCTGGCTAACTAGAGAACCCACTGCTTAAGCCTCAATAAAGCTTGGGCTGCAGGGCG

GGGCCTCCCCACCAAACTAGCCCTGTTCGCGCTCTCTCGGCAGTGCCGGGGGGCGCCGCCTC

TGF-b Signal Sequence -->
      M  P  P  S  G  L  R  L  L  P  L  L  L  P  L  L  W  L  L  V
CCCCATGCCGCCCTCCGGGCTGCGGCTGCTGCCGCTGCTGCTACCGCTGCTGTGGCTACTGG NaeI    SstII    AR -->
   L  T  P  S  R  P  A  A  G  V  V  K  P  P  Q  N  K  T  E  S
TGCTGACGCCTAGCCGGCCAGCCGCGGGAGTAGTTAAGCCCCCCCAAAACAAGACGGAAAGT E  N  T  S  D  K  P  K  R  K  K  K  G  G  K  N  G  K  N  R  R
GAAAATACTTCAGATAAACCCAAAAGAAAGAAAAAGGGAGGCAAAAATGGAAAAAATAGAAG N  R  K  K  K  N  P  C  N  A  E  F  Q  N  F  C  I  H  G  E  C
AAACAGAAAGAAGAAAAAATCCATGTAATGCAGAATTTCAAAATTTCTGCATTCACGGAGAAT K  Y  I  E  H  L  E  A  V  T  C  K  C  Q  Q  E  Y  F  G  E
GCAAATATATAGAGCACCTGGAAGCAGTAACATGCAAATGTCAGCAAGAATATTTCGGTGAA R  C  G  E  K  *     EcoRV/XbaI
CGGTGTGGGGAAAAGTAA  GATATCTAGA*
```

FIG. 19

FIG. 20

```
HincII
    trp-35                       lac-10           mRNA 5' lac
G (TTGACA) ATTAATCATCGGCTCG (TATAATG) TGTGG AATTGTGAGCG binding site      lacSD                  croSD       BglII
GATAACAATTTCACAC (AGGA) AACAGGATCACTA (AGGA) GGTTCAGATCT PvuI
AlkP signal->
ATGAAACAATCTACGATCGCCCTCGCACTTCTCCCACTGCTGTTCACTCC
 M   K   Q   S   T   I   A   L   A   L   L   P   L   L   F   T   P AR->
AGTGACAAAAGCTGTAGTTAAGCCCCCCCAAAACAAGACGGAAAGTGAAAA
 V   T   K   A   V   V   K   P   P   Q   N   K   T   E   S   E   N TACTTCAGATAAACCCAAAAGAAAGAAAAAGGGAGGCAAAAATGGAAAAAA
 T   S   D   K   P   K   R   K   K   K   G   G   K   N   G   K   N TAGAAGAAACAGAAAGAAGAAAAATCCATGTAATGCAGAATTTCAAAATTT
 R   R   N   R   K   K   K   N   P   C   N   A   E   F   Q   N   F CTGCATTCACGGAGAATGCAAATATATAGAGCACCTGGAAGCAGTAACATG
 C   I   H   G   E   C   K   Y   I   E   H   L   E   A   V   T   C SspI                                       EcoRV
CAAATGTCAGCAAGAATATTTCGGTGAACGGTGTGGGGAAAAGTAAGATAT
 K   C   Q   Q   E   Y   F   G   E   R   C   G   E   K   *

XbaI    (SalI/BamHI)
CTAGAGTCGATCCGTGACTAATTGGGGACCCTAGAGGTCCCCTTTTTTATTTTAAAA
``` pTacAPHILE

```
Hinc II
    trp-35                              lac-10              mRNA 5'  lac
G (TTGACA) ATTAATCATCGGCTCG (TATAATG) TGTGG AATTGTGAGCG binding site      lacSD                        croSD           BgI II
GATAACAATTTCACAC (AGGA)  AACAGGATCACTA (AGGA) GGTTCAGATCT PvuI
AlkP signal—>
ATGAAACAATCTACGATCGCCCTCGCACTTCTCCCACTGCTGTTCACTCC
 M  K  Q  S  T  I  A  L  A  L  L  P  L  L  F  T  P SstII    AR Hydrophilic domain —>
AGTGACCGCGGGAGTAGTTAAGCCGCCCCAAAAACAAGACGGAAAGTGAAAA
 V  T  A  G  V  V  K  P  P  Q  N  K  T  E  S  E  N TACTTCAGATAAACCCAAAAGAAAGAAAAAGGGAGGCAAAAATGGAAAAAA
 T  S  D  K  P  K  R  K  K  K  G  G  K  N  G  K  N EcoRI
               EGF->
TCGAAGAAACAGAAAGAAGAAGAATTCTGACTCTGAATGCCCGCTGTCTCA
 R  R  N  R  K  K  K  N  S  D  S  E  C  P  L  S  H TGACGGCTACTGCCTGCATGACGGCGTATGCATGTACATCGAAGCTCTGGA
 D  G  Y  C  L  H  D  G  V  C  M  Y  I  E  A  L  D SphI
CAAGTACGCATGCAACTGCGTTGTTGGCTACATCGGCGAACGTTGCCAGTA
 K  Y  A  C  N  C  V  V  G  Y  I  G  E  R  C  Q  Y BamHI  xbaI
CCGTGACCTGAAATGGTGGGAACTGCGTTAAGGATCCTCTAGAGTCGATCC

GTGACTAATTGGGGACCCTAGAGGTCCCCTTTTTTATTTTAAAA
```

*FIG. 21*

AMPHIREGULIN: A BIFUNCTIONAL GROWTH MODULATING GLYCOPROTEIN

The present application is a continuation-in-part of copending application Ser. No. 181,884 filed Apr. 15, 1988 which is a continuation-in-part of copending application Ser. No. 148,327 filed Jan. 25, 1988 both now abandoned each of which is incorporated by reference herein in its entirety.

1. INTRODUCTION

The present invention relates to the production and uses of Amphiregulin, a novel growth regulatory glycoprotein. The proteins of the invention strongly inhibit the growth of several tumor-derived cell lines while promoting cell growth in several other cell lines. A wide range of therapeutic applications of this bifunctional growth regulator are described, including but not limited to the treatment of wounds and the diagnosis and treatment of cancers.

2. BACKGROUND OF THE INVENTION

Cellular growth and differentiation appear to be initiated, promoted, maintained, and regulated by a multiplicity of stimulatory, inhibitory, and synergistic factors and hormones. The alteration and/or breakdown of the cellular homeostasis mechanism seems to be a fundamental cause of growth related diseases, including neoplasia. Growth modulatory factors are implicated in a wide variety of pathological and physiological processes including signal transduction, cell communication, growth and development, embryogenesis, immune response, hematopoiesis, cell survival and differentiation, inflammation, tissue repair and remodeling, atheroscleorosis and cancer. Justifiably, there is a great deal of interest in isolating, characterizing, and defining the functional mechanisms of growth modulatory factors because of their potential use in the diagnosis, prognosis, and treatment of cancer. Moreover, acquiring knowledge of these factors will aid in the understanding of the basic mechanisms behind normal growth control and the loss thereof in cancer cells.

Epidermal growth factor (EGF), transforming growth factor-$\alpha$ (TGF$\alpha$), platelet-derived growth factor (PDGF), fibroblast growth factor (FGF), nerve growth factor (NGF), transforming growth factor-$\beta$ (TGF$\beta$), insulin growth factor I and II (IGF I, IGF II), hematopoietic growth factors such as erythropoietin, colony stimulating factors (CSF 1 and 2), interleukins (IL-1 to 6), interferons (IFN $\alpha$, $\beta$, $\gamma$), tumor necrosis factor $\alpha$ and $\beta$ (TNF $\alpha$, $\beta$), leukoregulin, oncostatin M, and other less defined factors are growth and differentiation modulatory proteins produced by a variety of cell types either under normal physiological conditions or in response to exogenous stimuli. Most of these factors appear to act in autocrine and paracrine fashions. (For reviews see: Goustin, et al., 1986, Cancer Res. 46: 1015-1029; Rozengurt, 1986, Science 234: 161-66; Pardee, 1987, Cancer Res. 47: 1488-1491; Sachs, 1986, Sci. Amer. 254: 40-47; Marshall, 1987, Cell 50: 5-6; Melcher and Anderson, 1987, Cell 30: 715-720; Clemens and McNurlan, 1985, Biochem. J. 226: 345-360; Nathan, 1987, J. Clin. Invest. 79: 319-326; Sporn and Roberts, 1986, J. Clin. Invest. 78: 329-332; Old, 1987, Nature, 326: 330-331; Beutler and Cerami, 1987, New Eng. J. Med. 316: 379-385; Weinstein, J. Cell. Biochem., 33: 213-224; Zarling, et al., 1987, Proc. Natl. Acad. Sci. U.S.A. 83: 9739-9744; Sporn and Todaro, 1985, N. Eng. J. Med. 303: 878-880; Sporn and Roberts, 1985, Nature 313:, 745-747).

Biologically active phorbol esters such as 12-0-tetradecanoyl-phorbol-13-acetate (TPA) are potent tumor-promoters in vivo and elicit and modulate a wide variety of biological and biochemical responses in vivo as well as in vitro (Blumberg, 1981, Crit. Rev. Toxicol. 9: 153-197; Slaga, 1983, Cancer Surv. 2: 595-612). It has been known for some time that TPA inhibits the growth of the human breast adenocarcinoma cell line MCF-7. In addition, TPA also alters the morphology of MCF-7 cells inasmuch as TPA treated cells exhibit the morphological characteristics of secretory cells (Osborne, et al., 1981, J. Clin. Invest. 67: 943-951; Valette et al., 1987, Cancer Res. 47: 1615-1620).

3. SUMMARY OF THE INVENTION

The present invention relates to Amphiregulin, a novel cell growth regulatory factor which demonstrates unusual bifunctional cell growth regulatory activity. Amphiregulin inhibits the growth of neoplastic cells yet augments the growth of certain normal cells. Amphiregulin is an extremely hydrophilic glycoprotein having a median molecular weight of 22,500 daltons which occurs in two distinct yet functionally equivalent forms, a truncated form and a larger form. Except for the additional six N-terminal residues found in the larger form, the two forms are perfectly homologous at the amino acid level (FIG. 12). The invention is partly based on applicants' discovery that TPA-treated MCF-7 cells release a glycoprotein which inhibits the growth of the A431 epidermoid carcinoma cell line and other tumor cell lines, but augments the growth of normal human fibroblasts and some other cell lines.

The invention is described by way of examples in which Amphiregulin is identified, purified to homogeneity, and thoroughly characterized structurally and functionally. In other examples, the isolation and sequencing of both cDNA and genomic clones encoding the Amphiregulin precursor are described. These clones were used to prepare expression vectors capable of directing the high level synthesis of biologically active Amphiregulin in transformed bacterial and transfected eucaryotic host cells.

A wide variety of uses for this unique factor are encompassed by the invention described herein.

4 BRIEF DESCRIPTION OF THE FIGURES

FIG. 1. Preparative reversed-phase HPLC of breakthrough and wash.

Figure 2:
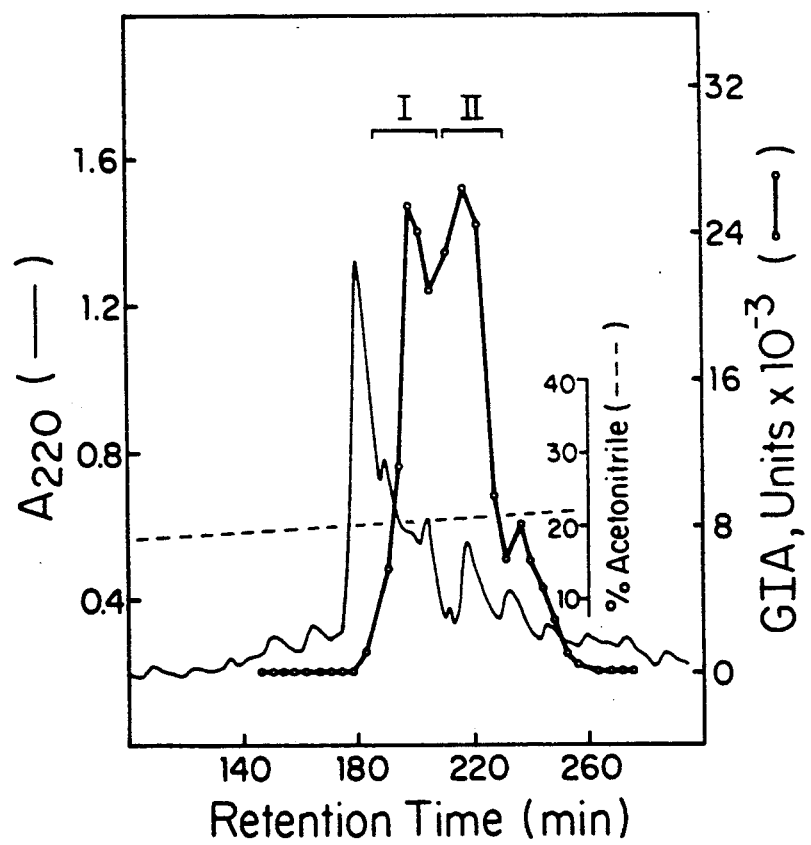

FIG. 2. Semi-preparative reversed phase HPLC of pooled fractions 47 to 62 from FIG. 1.

Figure 3:
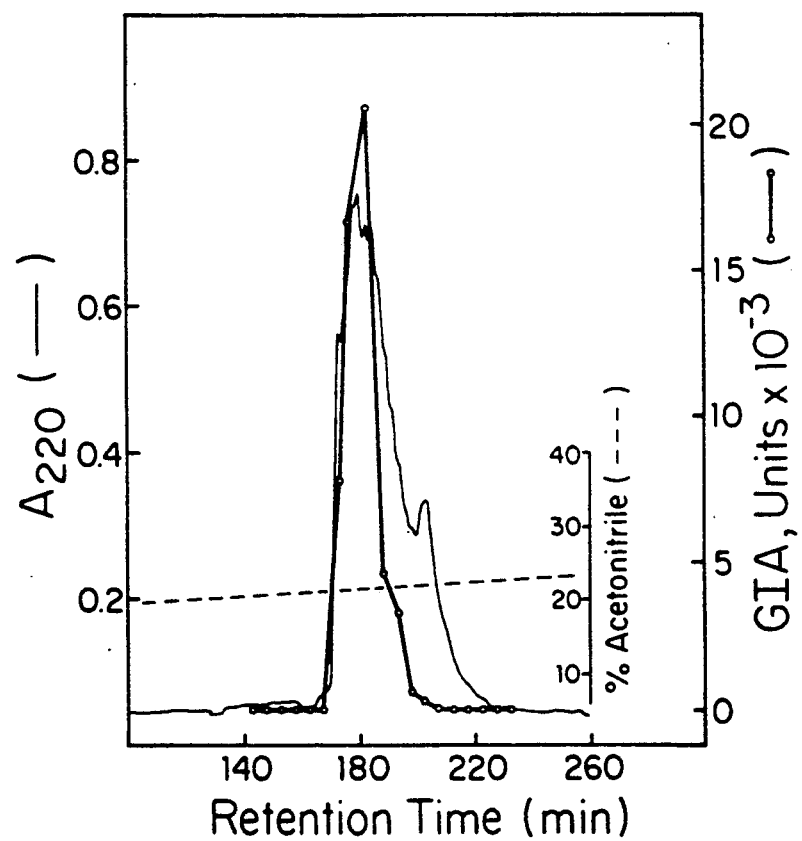

FIG. 3A. Analytical reversed-phase HPLC of pool I from previous run.

Figure 3B:
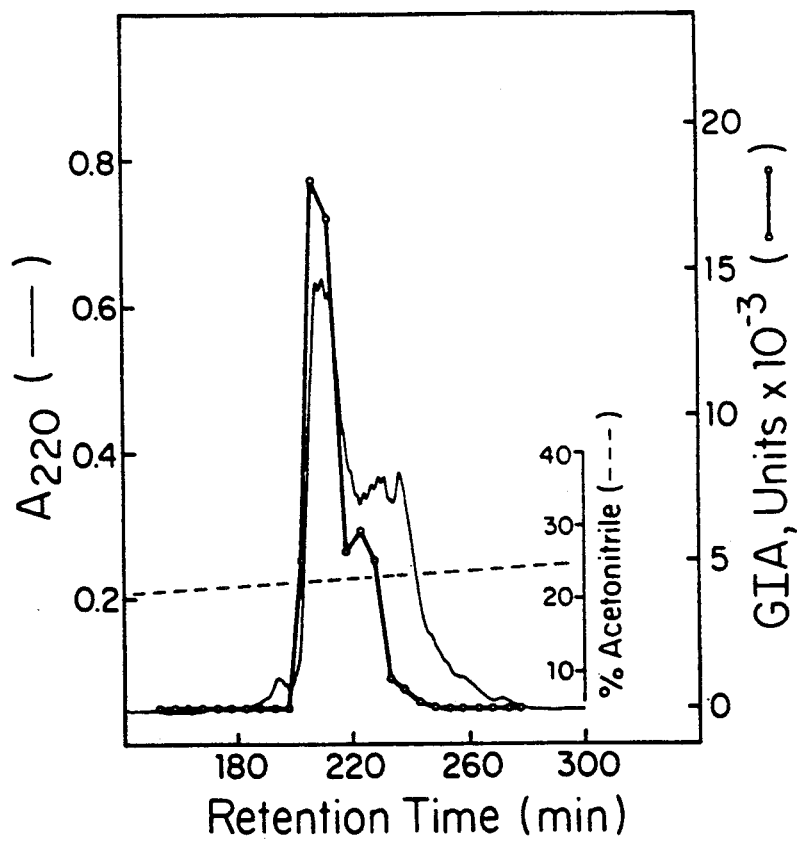

FIG. 3B. Analytical reversed-phase HPLC of pool II from previous run.

Figure 4:
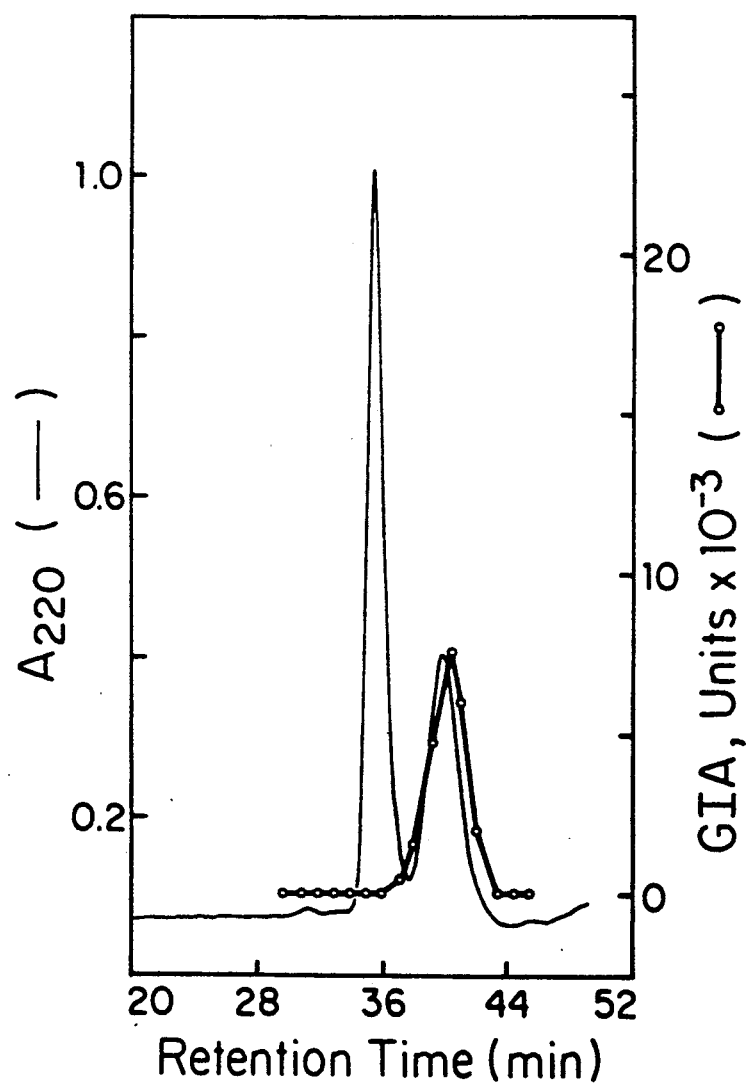

FIG. 4. Gel permeation chromatography of fractions from FIG. 3A and 3B on Bio-Sil TSK 250 columns. Chromatography was performed as described in Section 6.3.2., infra. (A) HPLC of concentrated fraction 35 (FIG. 3A); (B) HPLC of concentrated fraction 36 (FIG. 3A); (C) HPLC of concentrated fraction 37 (FIG. 3A); (D) HPLC of concentrated fractions 41 and 42 together (FIG. 3B).

Figure 5:
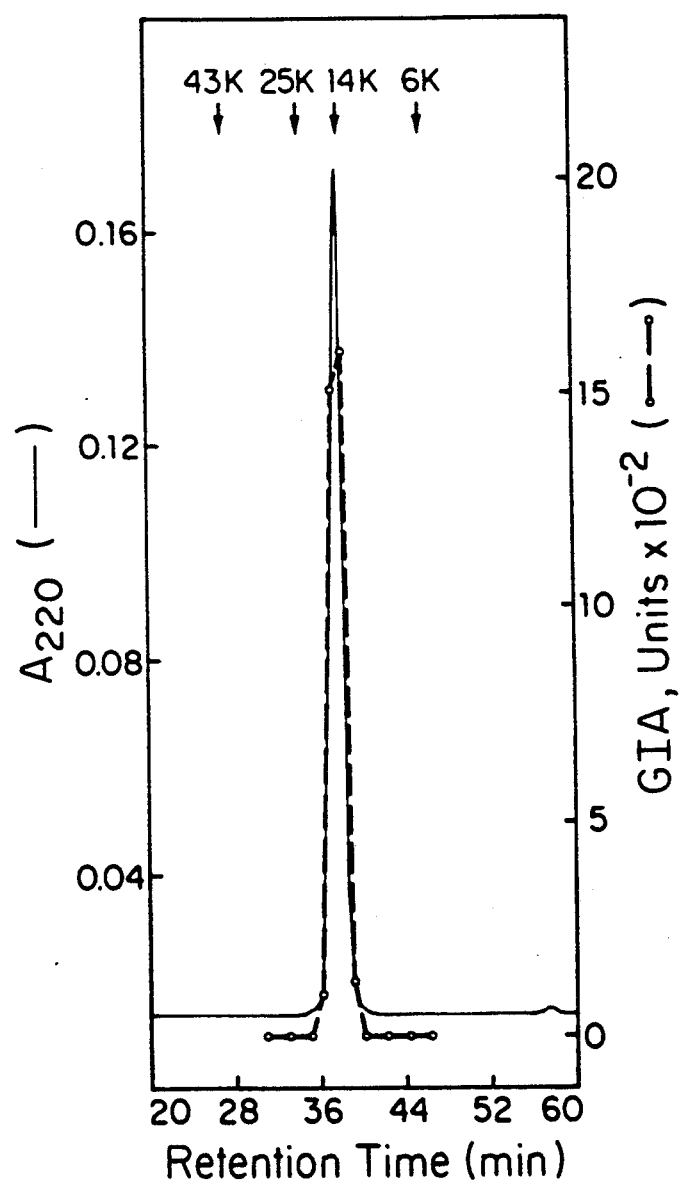

FIG. 5. Analysis of purified AR and S-pyridylethylated-AR (SPE-AR) by gel permeation HPLC on Bio-Sil TSK 250 columns. Chromatography was performed as described in Section 6.3.2., infra. The molecular weight markers used were ovalbumin, 43 kD; chymotrypsinogen A, 25 kD; ribonuclease, 14 kD; and insulin, 6 kD; (A) AR; (B) SPE-AR.

Figure 6A:
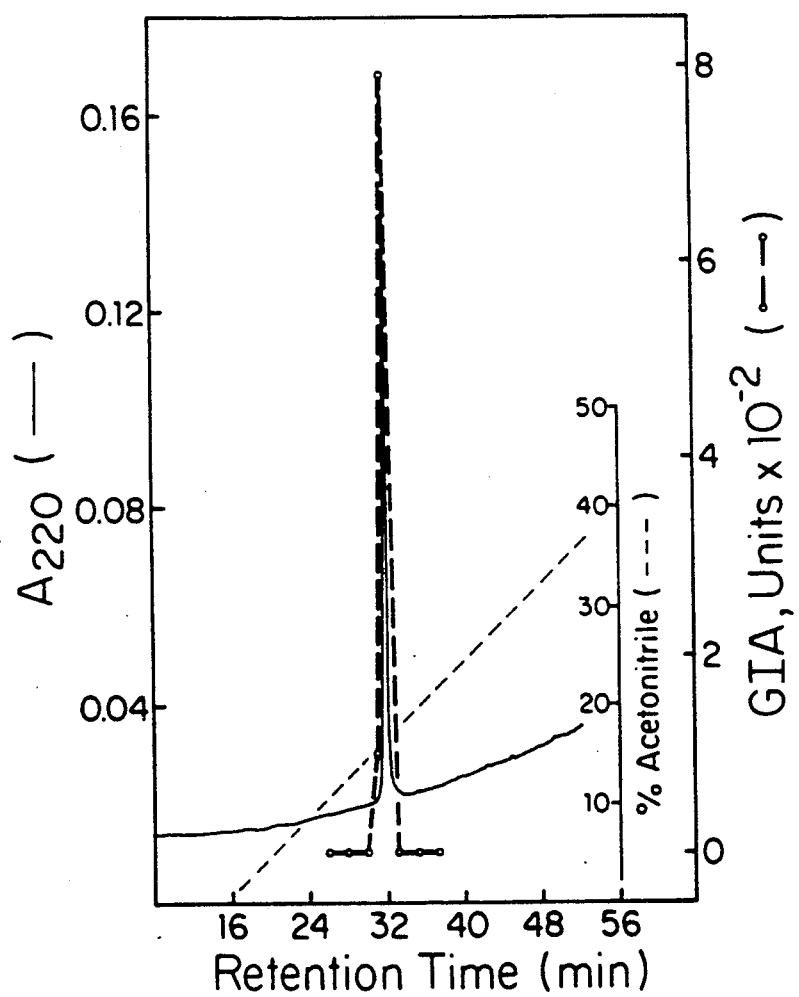
Figure 6B:
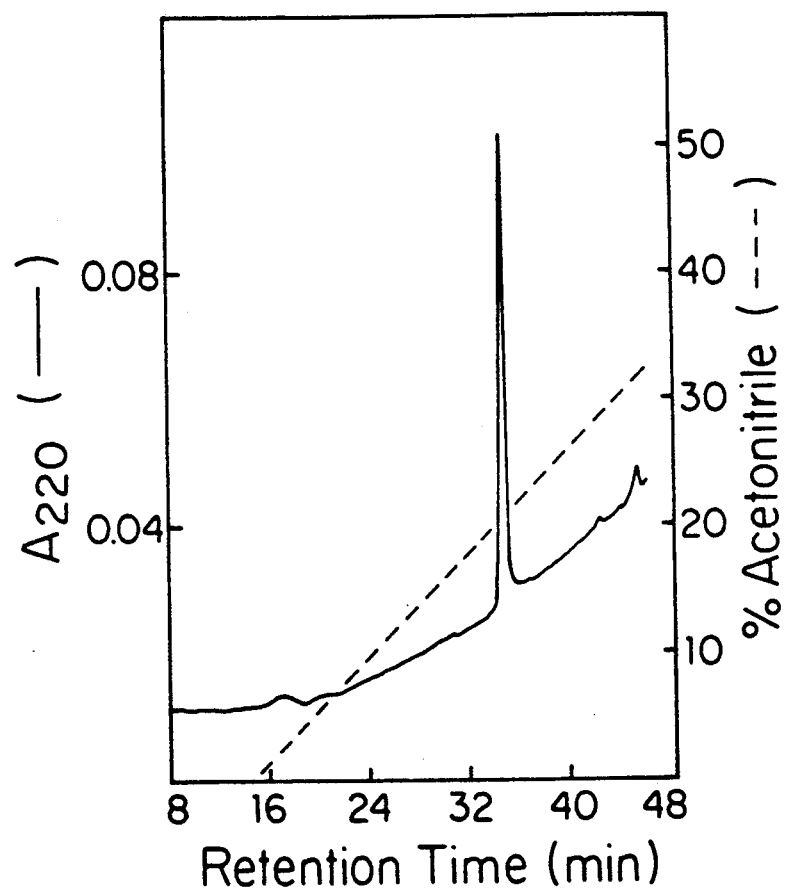

FIG. 6. Analysis of AR and SPE-AR on a reversed-phase ultrapore RPSC C3 column (4.6×75 mm). The gradient was run between primary solvent 0.1% TFA and the secondary solvent acetonitrile with 0.1% TFA at a flow rate of 1 mL/min at room temperature. 1 ml fractions were collected. (A) AR; (B) SPE-AR.

FIG. 7. SDS-PAGE analysis of AR Proteins. (A) A 15% SDS-PAGE gel (0.75 mm×18 cm×15 cm, Bio-Rad) with a discontinuous buffer system were run at 30 milliampere constant current. The molecular weight markers used were phosphorylase B, 92.5 kD; BSA, 66.2 kD; ovalbumin, 43 kD; carbonic anhydrase, 31 kD; chymotrypsinogen A, 25.7 kD; soybean trypsin inhibitor, 21.5 kD; lactoglobulin, 18.4 kD; lysozyme, 14.4 kD; aprotonin, 6.2 kD; and insulin subunit, 3 kD. Lane 1: AR; Lane 2: NG-AR; Lane 3: SPE-AR; Lane 4: NG-SPE-AR. (B) 20% SDS-PAGE minigel (0.75 mm×10 cm×7 cm) was run at 200 volts constant voltage. The same molecular weight markers as above were used. Lane 1: AR; Lane 2: NG-AR; Lane 3: Phospholipase treated NG-AR, separated on rp HPLC.

Figure 8:
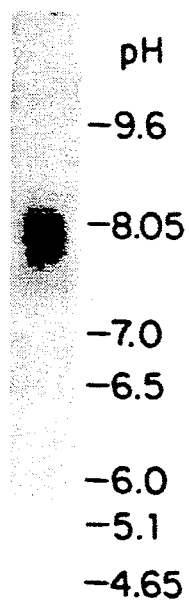

FIG. 8. IEF analysis of $^{125}$I-labeled AR. The following standards, having $P_I$ values of between 4.65 and 9.6 were used: phycocyanin, 4.65; β-Lactoglobulin B, 5.1; bovine carbonic anhydrase, 6.1; human carbonic anhydrase 6.5; equine myoglobin, 7.0; whale myglobin 8.05; α-chymotrypsin, 8.8; and cytochrome C, 9.6.

FIG. 9 (A) Dose response curve of AR on the inhibition of $^{125}$I-deoxyuridine incorporation into DNA of A431 cells; (B) Effect of AR on the stimulation of $^{125}$I-deoxyuridine incorporation into DNA of human foreskin fibroblasts (Sadamoto).

Figure 10:
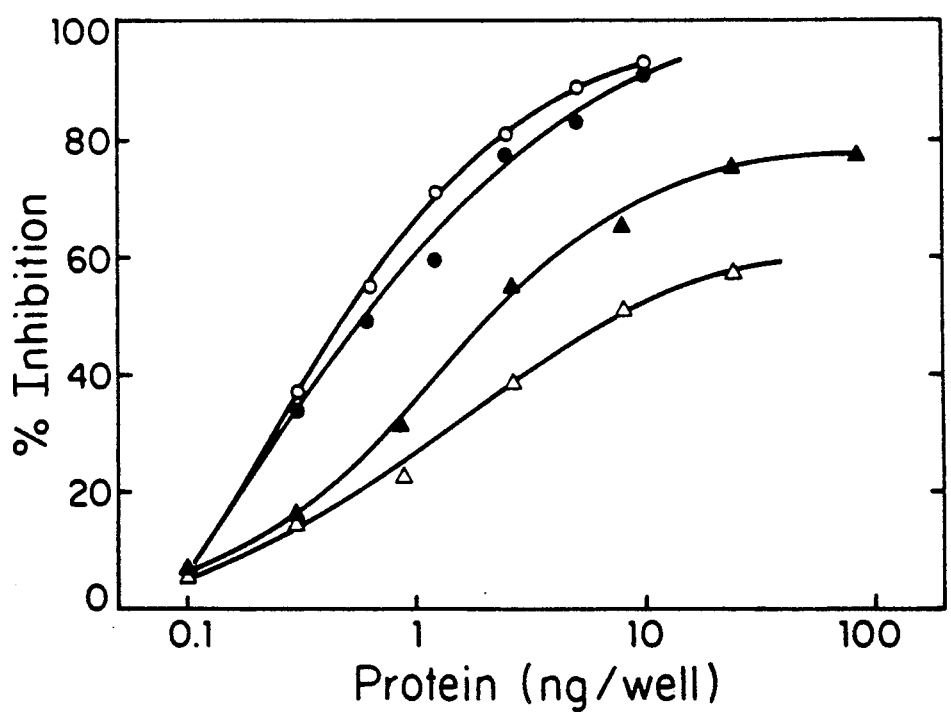

FIG. 10. Competition of $^{125}$I-EGF binding to fixed A431 cells or A431 plasma membranes by murine EGF and AR. Binding assays were performed as described in Section 6.1.5., infra. 100 μl or 50 μl samples per well were used for assays with fixed cells or membranes, respectively.

| Symbol | Receptor Source | Competitor |
|--------|-----------------|------------|
| ● | Fixed cells | EGF |
| ▲ | Fixed cells | AR |
| ○ | Membranes | EGF |
| △ | Membranes | AR |

Figure 11:
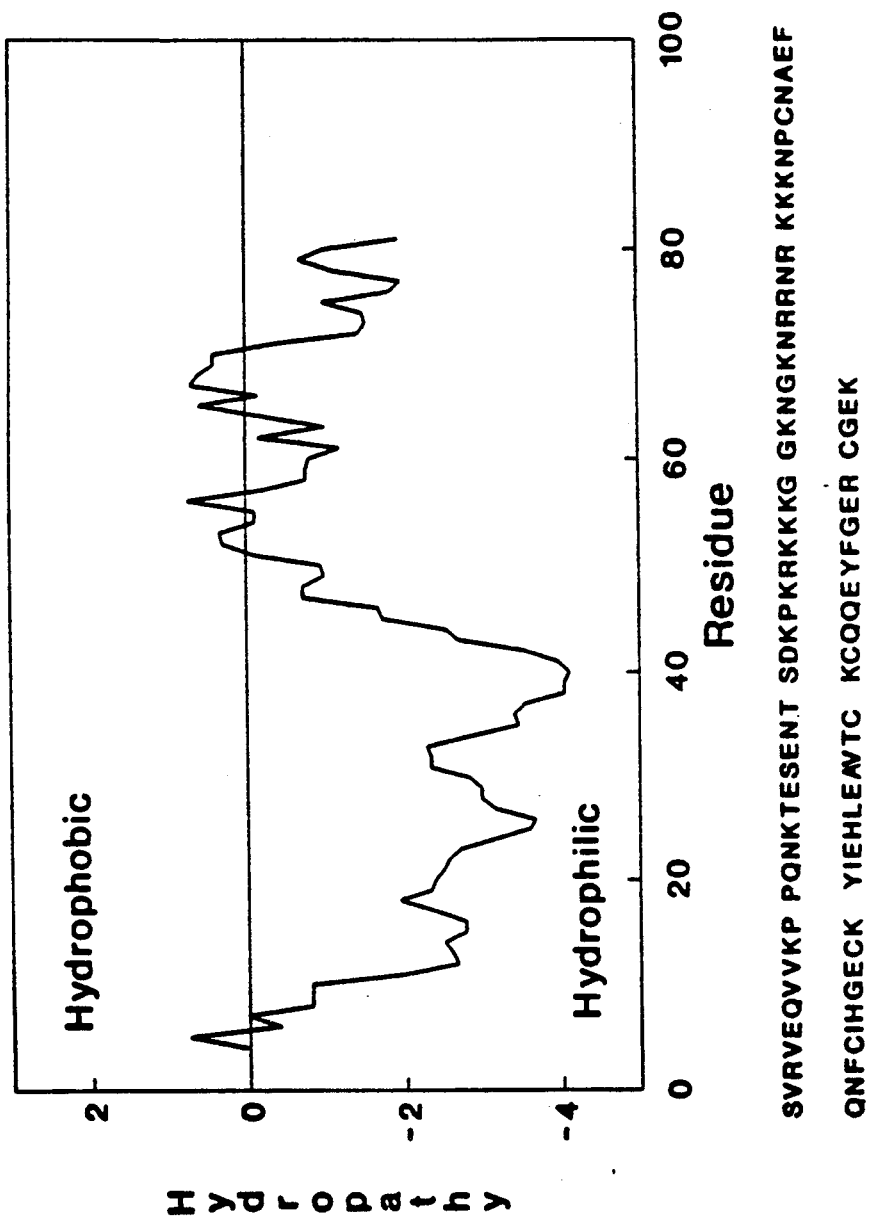
Figure 11C:
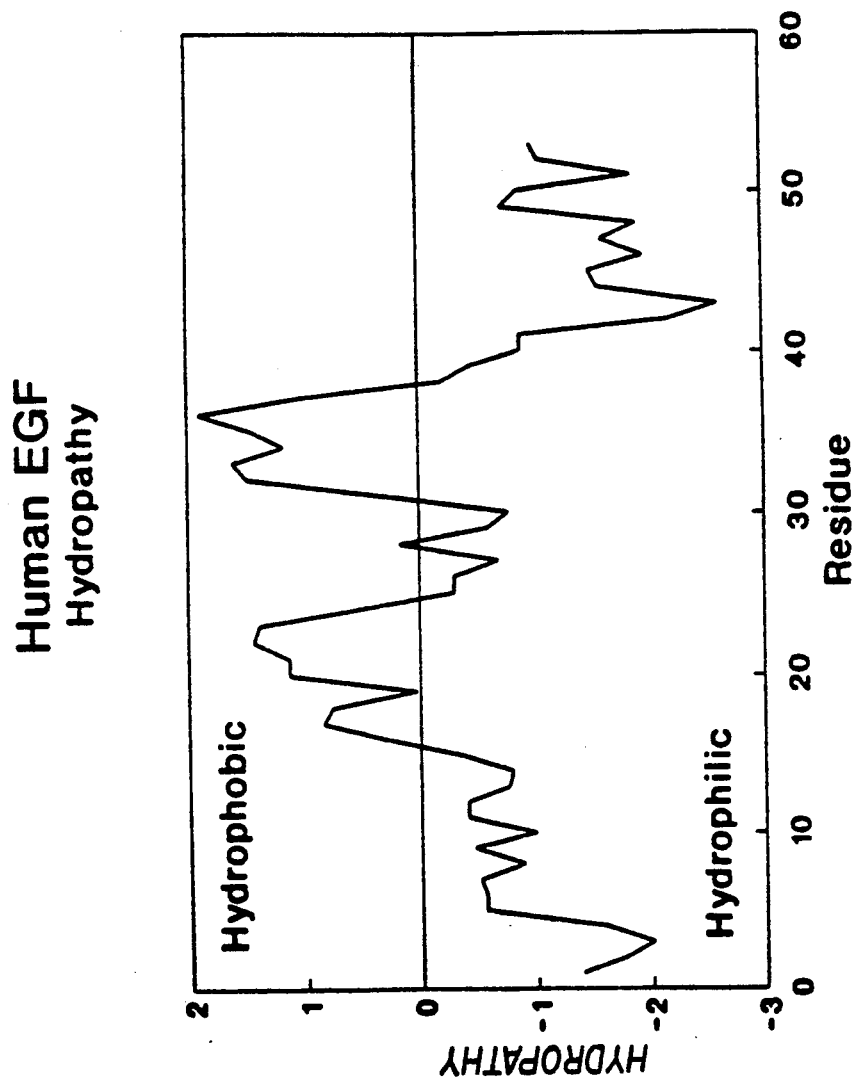

FIG. 11. Hydropathy analysis of AR and human EGF (Kyte and Doolittle). (A) AR (residues 1–84); (B) AR (residues 44–84); (C) EGF (residues 1–53); (D) AR precursor (residues 1–252); (E) comparison of human AR (residues 1–84) and EGF (residues 1–53) [alignment is according to FIG. 13 such that cysteine, residue 46 of mature AR corresponds to cysteine, residue 6 of mature EGF].

FIG. 12(A) Amino acid sequence of mature AR and (B) truncated AR. The standard single letter code for amino acids is used: Alanine (A); Arginine (R); Asparagine (N); Aspartic acid (D); Cysteine (C); Glutamine (Q); Glutamic Acid (E); Glycine (G); Histidine (H); Isoleucine (I); Leucine (L); Lysine (K); Methionine (M); Phenylalanine (F); Proline (P); Serine (S); Threonine (T); Tryptophan (W); Tyrosine (Y); and Valine (V).

FIG. 13. Comparison of amino acid sequences of amphiregulin (AR) and members of the EGF superfamily.

FIG. 14. (A) $^{125}$I-AR binding to cellulose (○), denatured DNA cellulose (□), and native DNA cellulose (△). (B) $^{125}$I-AR binding to cellulose (○) and to DNA-cellulose (□) is compared to $^{125}$I-EGF binding to cellulose (△) and to DNA-cellulose (▽).

FIG. 15. Synthetic amphiregulin peptides generated by solid-phase technique. Five peptides, corresponding to residues 166–184 (No. 259), 108–130 (No. 264), 31–50 (No. 279), 71–90 (No. 280) and 221–240 (No. 281) were produced by solid phase synthesis, then purified by reverse-phase HPLC.

FIG. 16. Nucleotide and deduced amino-acid sequence of cDNA clone pAR1, encoding human amphiregulin.

FIG. 17. The human amphiregulin genomic sequence.

Figure 18:
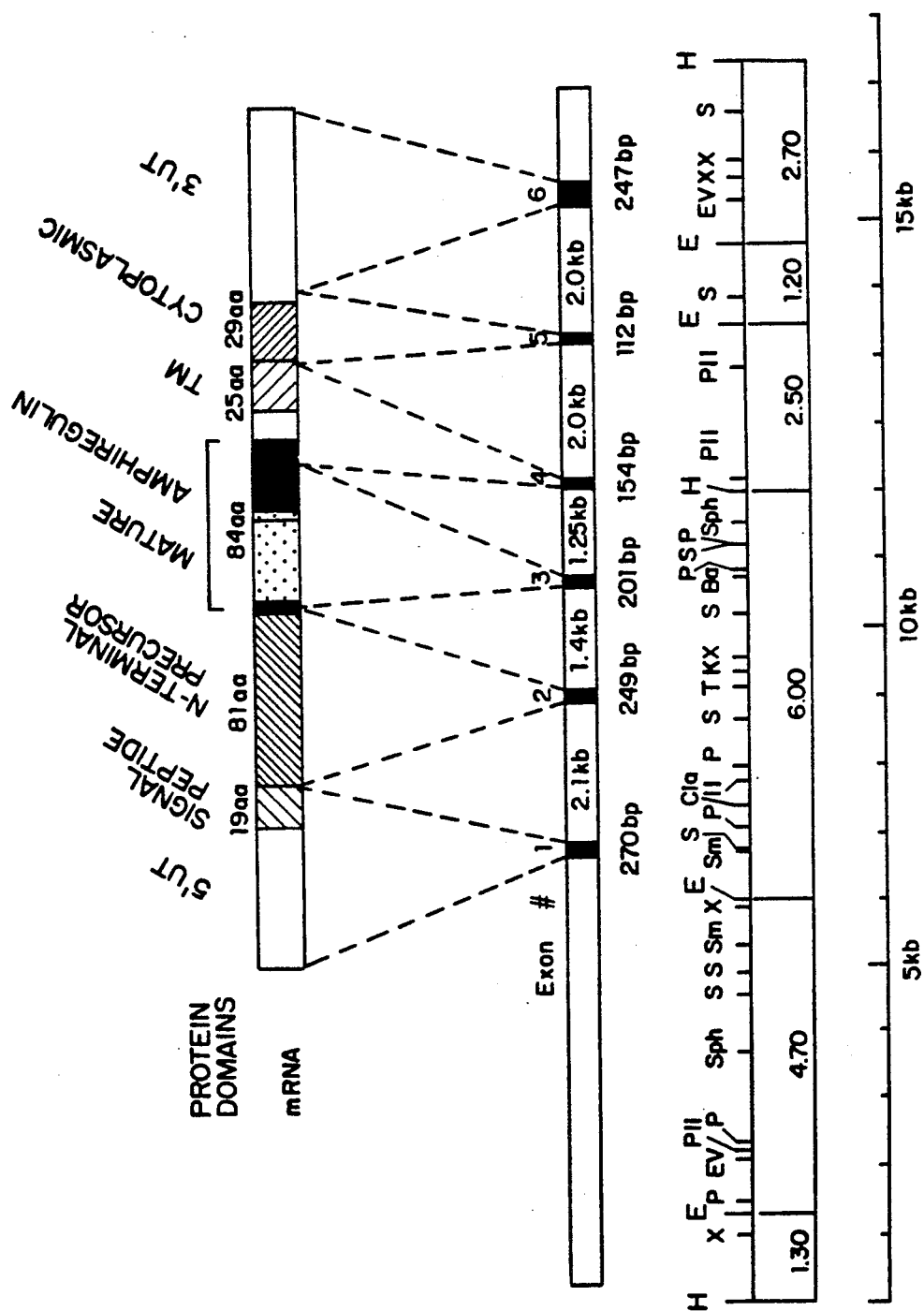

FIG. 18. Schematic diagram of the exon structure and protein domains of the AR molecule, relating to the genomic sequence.

FIG. 19. Nucleotide sequence of pDCHBAR1 Expression Vector.

FIG. 20. Nucleotide sequence of pTacAPAR1.

FIG. 21. Nucleotide sequence of pTacAPHILE.

5. DETAILED DESCRIPTION OF THE INVENTION

The present invention relates to Amphiregulin (AR), to nucleotide sequences encoding AR and the AR precursor, and to the production of AR by conventional or recombinant DNA methods.

AR, a novel cell growth regulatory factor, is expressed and secreted by TPA treated MCF-7 cells as two distinct yet functionally equivalent forms. The two forms are structurally identical except for an additional 6 amino-terminal residues in the larger form. AR exhibits potent inhibitory activity on DNA synthesis in neoplastic cells and therefore has potential as a powerful anti-tumor compound. Of particular interest is the ability of AR to promote growth in fibroblasts and other normal cells, suggesting that AR may be useful in treating conditions which require the acceleration of cell growth, i.e., burns and wounds.

AR, or fragments and derivatives thereof, have widespread potential therapeutic use in the treatment and monitoring of neoplasias as well as in the treatment of wounds. AR may also find use in the modulation of bone resorption and the immune response, and the stimulation of the arachidonic acid cascade. The Amphiregulin gene and gene-products, methods for their production, and uses thereof are described in more detail in the subsections and examples that follow.

5.1. Production and Purification of Amphiregulin

Amphiregulin is secreted by the human breast carcinoma cell line MCF-7 when treated with the tumor promoting agent 12-0-Tetradecanoyl-Phorbol-13-Acetate (TPA). Amphiregulin can be isolated from the conditioned media of such cultured TPA-treated MCF-7 cells and subsequently purified to high specific activity. Amphiregulin may also be isolated from other cell lines with or without induction by treatment with TPA or other tumor promoting agents. Alternatively, Amphiregulin may be produced by recombinant DNA techniques, or by solid phase peptide synthesis.

Amphiregulin may be purified by utilizing various procedures and techniques known in the art, including but not limited to chromatography (e.g., reverse phase liquid, gel permeation, liquid exchange, ion exchange, size exclusion, and affinity chromatography), centrifugation, electrophoretic procedures, differential solubility, or by any other standard technique for the purification of proteins.

In a specific embodiment of the invention, MCF-7 cells are treated with TPA for 48 hours and grown in fresh serum-free medium for 4 days. The resulting conditioned media is collected and used to prepare crude AR as described in Section 6.2, infra. A combination of reverse phase liquid and gel permeation chromatography can be used to purify AR to apparent homogeneity, as described in Section 6.3, infra, and results in AR purified between 1,842-fold and 2,270-fold over the crude starting material. The method is reproducible and yields purified AR preparations having specific activities of between 2.7 and $3.4 \times 10^6$ units/mg protein.

5.2. The Amphiregulin Gene

5.2.1. Isolation and Cloning of the Amphiregulin Gene

In the practice of the method of the invention, the nucleotide coding sequence for human amphiregulin, or its functional equivalent can be used to generate recombinant molecules which will direct the expression of the human amphiregulin product. The nucleotide coding sequence for AR may be obtained from cell sources that produce AR-like activity. For example, in a specific embodiment, the human breast carcinoma cell line MCF-7 is used as the source of the AR nucleotide coding sequence. The coding sequence may be obtained by cDNA cloning of RNA isolated and purified from such cellular sources or by genomic cloning. Either cDNA or genomic libraries of clones may be prepared from the DNA fragments generated using techniques known in the art, including but not limited to the use of restriction enzymes.

The fragments which contain the gene for AR may be identified in a number of ways known in the art. For example, a portion of the AR amino acid sequence can be used to deduce the DNA sequence, which DNA sequence can then be chemically synthesized, radioactively labeled, and used as a hybridization probe.

Other methods which can be used to isolate the AR gene include but are not limited to chemically synthesizing the gene sequence itself from a known sequence which may, for example, be derived from the amino acid sequence of AR. Alternatively, in vitro translation of selected mRNA followed by functional or immunological assays of the translation products can be used. The identified and isolated gene can then be inserted into an appropriate cloning vector. A large number of vector-host systems known in the art may be used. Possible vectors include, but are not limited to, plasmids or modified viruses, where the vector system is compatible with the host cell. Such vectors include, but are not limited to, bacteriophages such as lambda derivatives, or plasmids such as PBR322 or pUC plasmid derivatives. Recombinant molecules can be introduced into host cells via transformation, transfection, infection, electroporation, etc.

In a particular embodiment, the AR gene expressed by MCF-7 cells is cloned by selecting mRNA produced in response to treatment of MCF-7 cells with TPA and constructing a cDNA library in bacteriophage λgt10. Since untreated MCF-7 cells apparently do not synthesize and secrete AR protein, it was presumed that the induction of AR by TPA might also be noticed at the level of transcription and that such a cDNA library should be considerably enriched for AR-containing sequences. Probing the cDNA library with degenerate and best guess oligonucleotides based on human codon usage (Lathe, 1985, J. Mol. Biol. 183:1-12 and as described in section 8.1, infra) resulted in isolation of AR cDNA clones. These cDNA clones were then used to characterize the AR mRNA and the AR gene. Furthermore, the nucleotide sequence of the AR cDNA (section 8.2, infra and FIG. 16) can be used to deduce AR primary amino acid sequence.

Due to the inherent degeneracy of nucleotide coding sequences, other DNA sequences which encode substantially the same or a functionally equivalent amino acid sequence may be used in the practice of the methods of the invention. Such alterations of the AR nucleotides sequence include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

The AR cDNA can be used as a probe to detect the AR mRNA in TPA-induced MCF-7 cells. The AR mRNA is approximately 1400 bp in length.

As described in section 9, infra, the AR cDNA can be used to characterize the AR gene. The chromosome assignment of the human AR gene was determined by in situ hybridization of $^3$H-labelled AR cDNA to normal metaphase chromosomes, revealing that the human AR gene resides on chromosome 4 region 4q13-21, a region thought to be involved in lymphocyte differentiation (see section 9.2, infra). The cDNA ws also used to isolate genomic DNA spanning the entire AR gene, including the 5' regulatory region. The AR gene was found to be approximately 10 kb in length, and is partitioned into 6 exons. The 5' regulatory region was incorporated into an expression vector containing a promoter-less chloramphenicol acetyltransferase (CAT) gene. This construct was able to stimulate transcription of the CAT gene when introduced transiently into MCF-7 cells, and activity was stimulated 6-7 fold by the addition of TPA (see section 9.4, infra). In specific embodiments of the invention, this 5' regulatory region can be used in expression vectors to control transcription of the AR gene or other structural genes. The chimeric AR-CAT construct can also be used to search for factors which regulate the expression of AR as described in Section 9 et seq. herein.

5.2.2. Construction of Expression Vectors Containing the Amphiregulin Coding Sequence In order to express a biologically active, mature form of AR, an expression vector/host system should be chosen which provides not only for high levels of transcription and translation but for the correct processing of the gene product. This is especially important when employing the entire coding sequence of the Amphiregulin precursor in the expression contructs since the mature form of Amphiregulin appears to be derived from the precursor product via cellular processing events. For example, a mammalian host cell system may be chosen for its ability to correctly process and secrete Amphiregulin into the extracellular environment.

Specifically, it appears that two forms of mature Amphiregulin are synthesized as the middle part of a common 252 amino acid precursor from which the two mature forms are liberated via alternate protelytic processing events. Additionally, Amphiregulin is glycosylated and may undergo tyrosine-sulfation, further underscoring the importance of selecting an expression system which is capable of executing these post-translational modifications, if desired in the final product.

A variety of animal/host expression vector systems (i.e., vectors which contain the necessary elements for directing the replication, transcription and translation of the AR coding sequence in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionine promoter).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionine promoter) or from viruses that grow in these cells, (e.g. vaccinia virus 7.5K promoter or Moloney murine sarcoma virus long terminal repeat) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where the entire AR gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the AR coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

Any of the methods previously described for the insertion of DNA fragments into a vector may be used to construct expression vectors containing the AR gene and appropriate transcriptional/translational control signals. These methods may include in vitro recombinant DNA techniques, synthetic techniques and in vivo recombinations (genetic recombination).

For example, in cases where an adenovirus is used as an expression vector, the AR coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing AR in infected hosts. Similarly, the vaccinia 7.5K promoter may be used.

An alternative expression system which could be used to express AR is an insect system. In one such system, *Autographa californica* nuclear polyhedrosis virus (AcNPV) is used as a vector to express foreign genes. The virus grows in *Spodoptera frugiperda* cells. The AR coding sequence may be cloned into non-essential regions (for example the polyhedrin gene) of the virus and placed under control of an AcNPV promoter (for example the polyhedrin promoter). Successful insertion of the AR coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera fruqiperda* cells in which the inserted gene is expressed.

Retroviral vectors prepared in amphotropic packaging cell lines permit high efficiency expression in numerous cell types. This method allows one to assess cell-type specific processing, regulation or function of the inserted protein coding sequence.

In addition, a host cell strain may be chosen which modulates the expression of the inserted sequences, or modifies and processes the gene product in the specific fashion desired. Expression from certain promoters can be elevated in the presence of certain inducers, (e.g. zinc and cadmium ions for metallothionein promoters). Therefore, expression of the genetically engineered AR may be controlled. This is important if the protein product of the cloned foreign gene is lethal to host cells. Furthermore, modifications (e.g. glycosylation) and processing (e.g., cleavage) of protein products are important for the function of the protein. Different host cells have characteristic and specific mechanisms for the post-translational processing and modification of proteins. Appropriate cell lines or host systems can be chosen to ensure the correct modification and processing of the foreign protein expressed.

Expression vectors which may be used according to the present invention include, but are not limited to, the following:

Plasmid pSV2Neo. Plasmid pSV2Neo is described in Southern et al., (1982) J. Mol. Applied Genetics 1,327–341.

Plasmid pSV2dhfr. Plasmid pSV2dhfr (Subramani et al., 1981, Mol. Cell Biol. 1,854–864), contains the mouse dihydrofolate reductase (dhfr) gene under the control of the SV40 promoter.

Plasmid pH3M. Plasmid pH3M (Aruffo et al., 1987, Proc. Natl. Acad. Sci. U.S.A., 84, 3365–3369), contains a chimeric promoter composed of the human cytomegalovirus (CMV) AD169 immediate early enhancer fused to the HIV LTR positions −67 to +80. The LTR is followed by a polylinker with 5'-to-3' sites: HindIII, XbaI, XhoI, BstXI, XhoI, PstI, and XbaI. The small t antigen splice/polyadenylation signals from pSV2 and an SV40 origin of replication are downstream from the polylinker. The latter permits amplification in cells containing the SV40 large T antigen such as COS and WOP cells. A supressor tRNA gene supports growth in pVX based vectors and bacteria carrying the P3 plasmid such as MC1061/P3.

Plasmid pH3M/bOncM. Plasmid pH3M/bOncM was obtained from Najma Malik, Oncogen. It contains the simian TGF-β 5' untranslated and leader sequence fused to the Oncostatin M coding sequence inserted into pH3M at the HindIII/XhoI (filled) sites. The TGF-β sequence consists of 85 bp 5' untranslated region beginning at a HindIII (originating from pSP65 polylinker) and an adjacent PstI site from the TGF-β cDNA, followed by 87 bp encoding the 29 amino acid signal sequence, which normally is cleaved between a glycine-leucine dipeptide sequence.

Plasmid pH3ARP. Plasmid pH3ARP is a pH3M based vector designed for transient expression of the AR precursor in COS cells. It contains 13 bp of the AR 5' untranslated region, and the entire coding region and 3' untranslated sequences. This plasmid was generated by ligation of the 4 kb fragment of the pH3M vector digested with HindIII and XbaI, oligonucleotides EVSAL3 and EVSAL4, and the gel purified 1.1 kb HgaI/XbaI cDNA fragment from pAR1. EVSAL3 and EVSAL4 are complimentary with a 5' HindIII, EcoRV, SalI, and HgaI sites. The construct also retains the EcoRI to XbaI polylinker sites from pEMBL18 just following the 3' untranslated region.

|        |    | HindIII | EcoRV | SalI | HgaI |
|--------|----|---------|-------|------|------|
| EVSAL3 | 5' | AGCTTGATATCGTCGA |
| EVSAL4 | 3' | ACTATAGCAGCTGACGC |

Plasmid pSVDR/bOM. Plasmid pSVDR/bOM was obtained from Jeff Kallestad, Oncogen. It is a fusion between pSV2dhfr and pH3M/bOM and provides a vector with a cDNA driven by the CMV/HIV promoter of pH3M flanked by TGF-β signal sequence and SV40 polyadenylation signals, in addition to the mouse dhfr gene driven by SV40 early promoter. It was generated by ligation of BamHI/NruI (filled) digested pH3m/bOM with BamHI digested pSV2dhfr.

Plasmid pHras. Plasmid pHras is a mammalian expression vector developed by Stan McKnight, Univ. of Washington, Dept. of Pharmacology. It is a pML based vector which contains a 754 bp EcoRI to Tth111I fragment of Harvey Ras LTR, a polylinker with SmaI, BamHI, SalI, PstI, HindIII, and ClaI followed by the mouse DHFR cDNA and Hepatitis B virus 3' untranslated/polyadenlyation signal. The distance from the BamHI in the polylinker to the ATG of DHFR is 54 bp.

Plasmid pHLARGE. Plasmid pHLARGE is a mammalian expression construct which contains the 10 kb AR genomic sequences (SmaI to HindIII) driven by the Harvey ras LTR and followed by a nonfunctional, promoterless DHFR gene. It was formed by three-way ligation of the following fragments: 4.6 kb pHras SmaI/HindIII fragment; 6.0 kb SmaI/HindIII AR genomic fragment from pARH12; and 6.4 kb HindIII AR genomic fragment from pARH6.

Plasmid pHLARG1pcD. Plasmid pHLARG1pcD is a polycistronic mammalian expression construct. It contains the AR precursor cDNA sequence followed by the mouse dhfr gene driven by a single Harvey ras LTR. The primary transcript is a polycistronic message with 74 bp between the stop codon of AR and the ATG start codon of dhfr, thereby permitting the ribosome to reinitiate and translation to continue. pH3ARP was digested with EcoRV and the 700 bp fragment isolated. This fragment contained 13 bp AR 5' untranslated region, the complete AR precursor coding region, and 21 bp of 5' untranslated sequence. This fragment was ligated with the BamHI cut, filled, and phoshatased vector pHras.

Plasmid pLOSNL. Plasmid pLOSNL was obtained from Dusty Miller, Fred Hutchison Cancer Research Center, Seattle, Wash. This retroviral expression vector was designed for generation of high titer, amphotropic helper free viral stocks capable of infecting, but not replicating in, a broad host range. The vector contains: a mutated Moloney murine leukemia virus LTR with packaging signals deleted; psi+ sequences; the ornithine transcarbamylase (OTC) gene containing two XhoI sites for insertion of a cDNA and subsequent inactivation of the OTC gene; SV2Neo, a selectable marker; the 3' LTR; and a pBR322 Amp resistant backbone.

Plasmid pLARSNL. Plasmid pLARSNL is an amphotropic retroviral expression construct containing the AR precursor cDNA coding region, lacking a poly(A) tail, driven by the viral LTR. SV2Neo permits selection for expressing transfectants. pLARSNL was generated by ligation of the 800 bp SalI fragment from pHLARG1pcD with the 7.7 kb XhoI digested and phosphatased pLOSNL vector fragment.

5.2.3. Identification of Transfectants or Transformants Expressing the Amphiregulin Gene Product The host cells which contain the recombinant AR coding sequence and which express the biologically active, mature product may be identified by at least four general approaches: (a) DNA-DNA, DNA-RNA or RNA-antisense RNA hybridization; (b) the presence or absence of "marker" gene functions; (c) assessing the level of transcription as measured by the expression of AR mRNA transcripts in the host cell; and (d) detection of the mature gene product as measured by immunoassay and, ultimately, by its biological activity.

In the first approach, the presence of the human AR coding sequence inserted in the expression vector can be detected by DNA-DNA hybridization using probes comprising nucleotide sequences that are homologous to the human AR coding sequence.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the AR coding sequence is inserted within a marker gene sequence of the vector, recombinants containing the AR coding sequence can be identified by the absence of the marker gene function. Alternatively, a marker gene can be placed in tandem with the AR sequence under the control of the same or different promoter used to control the expression of the AR coding sequence. Expression of the marker in response to induction or selection indicates expression of the AR coding sequence.

In the third approach, transcriptional activity for the AR coding region can be assessed by hybridization assays. For example, polyadenylated RNA can be isolated and analyzed by Northern blot using a probe homologous to the AR coding sequence or particular portions thereof. Alternatively, total nucleic acids of the host cell may be extracted and assayed for hybridization to such probes.

In the fourth approach, the expression of the mature protein product can be assessed immunologically, for example by Western blots, immunoassays such as radioimmuno-precipitation, enzyme-linked immunoassays and the like. The ultimate test of the success of the expression system, however, involves the detection of the biologically active AR gene product. Where the host cell secretes the gene product the cell free media obtained from the cultured transfectant host cell may be assayed for AR activity. Where the gene product is not secreted, cell lysates may be assayed for such activity. In either case, biological assays such as the growth inhibition and stimulation assays described herein or the like may be used.

5.3. Structure of Amphiregulin

Amino acid sequencing of purified AR revealed that the preparation is comprised of an unequal mixture of two nearly identical forms of AR (see FIG. 12). One form, the larger of the two, comprises roughly 16% of the preparation. The other form, a truncated AR, comprises the remainder and majority of the preparation, and differs from its longer counterpart only in that it lacks the amino-terminal hexapeptide, SVRVEQ. The two forms are otherwise perfectly homologous at the amino acid level.

AR is an extremely hydrophilic glycoprotein with a median relative molecular weight of 22,500 daltons. N-Glycanase treatment, which removes N-linked carbohydrate, causes AR to migrate as a single band with relative molecular weight of 14,000, in good agreement with molecular weight calculations from AR gel permeation chromatography data. Under non-reducing conditions, AR migrated similarly. AR is, therefore, a single chain glycoprotein.

The primary structure of AR has been compared with many protein sequences. These comparisons show that AR is a unique protein having no significant structural homology with any of the compared proteins. The AR primary structure is, however, related to several other growth factors, most of which belong to the EGF-super family. It is reasonable to classify AR as a member of this group of proteins since several of its structural features closely parallel the highly conserved structural features found among the EGF-family proteins. For example, the N-terminal AR sequence resembles the N-terminal sequences of the TGFα, VGF, and MGF, in that this region is rich in proline, serine, and threonine residues. AR also has sites for N-linked glycosylation as do the N-terminal precursor regions of the TGFs and VGF. AR shows further sequence homology with other EGF-like proteins, with the conservation of 6 cysteine residues involved in 3 disulfide bonds which define the secondary structure of the mature forms of these growth factors. However, hydropathy analysis reveals significant differences between homologous AR and EGF sequences. For further comparisons between AR and other members of the EGF superfamily, refer to Table I, FIG. 13 and sections 9.7 and 9.8.

TABLE I

| Protein | Species | Region #1 | Region #2 |
|---------|---------|-----------|-----------|
| EGF | Human | CLHDGVCMYIE | CNCVVGYIGERC |
| TGF-α | Human | CFH-GTCRFLV | CVCHSGYVGARC |
| VGF | Vaccinia | CLH-GDCIHAR | CRCSHGYTGIRC |
| SGF | Shope | CLNNGTCFTIA | CVCRINYEGSRC |
| Factor IX | Human | CLNXGSCKDDI | CWCPFGFEGKNC |
| Factor X | Human | CQNXGKCKDGL | CTCLEGFEGKNC |
| Factor XII | Human | CLHXGRCLEVE | CHCPVGYTGPFC |
| Protein C | Human | CCGXGTCIDGI | CDCRSGWEGRFC |
| AR | Human | CIH-GECKYIE | CKCQQEYFGERC |

| Combined Homology Scores for Regions #1 and #2 | | | |
|---|---|---|---|
| | EGF Score | Coag. Score | AR Score |
| Growth Factor Family | >20 | <20 | <40 |
| Coagulation Factors | <25 | >25 | <40 |
| Amphiregulin Subfamily | <20 | <20 | >40 |

The Amphiregulin amino acid sequences shown in FIG. 12 as well as functional equivalents are within the scope of the invention. For example, the amphiregulin product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, and tyrosine.

5.4. Properties of Amphiregulin

AR is a single chain glycoprotein with a median molecular weight of about 22,500 daltons which exhibits bifunctional growth modulatory activities on a variety of cells in culture. Structurally, AR is related to the EGF family of growth factors and, in addition, may share functional similarities with other members of this family as indicated by the ability of AR to effectively compete with EGF for receptor binding.

AR is a monomeric protein which requires intrachain disulfide bonds for activity, does not require glycosylation for its biological activities, is stable under moderate acid and base treatments, and is stable when heat treated at 56° C. for 30 minutes. AR loses complete biological activity when reduced, when heated at 100° C. for 5 minutes, when digested with trypsin, endopeptidase Lys-C, endopeptidase Arg, and endopeptidase Glu.

Proteolytic cleavage by phospholipase D appears to convert AR to an active fragment or fragments with relative molecular weight of about 5600, as deduced from SDS-PAGE analysis Active fragments of AR are encompassed by the present application and are further discussed in Section 5.5, infra.

AR has potent anti-proliferative effects in vitro on several human cancer cell lines of epithelial origin. For example, AR effectively inhibits DNA synthesis of epidermal carcinoma of vulva A431, breast adenocarcinoma HTB 132, cervical epidermoid carcinoma CRL 1550, ovarian papillary adenoma HTB 75, ovarian teratocarinoma HTB 1572, and breast adenocarcinoma HTB 26 cells. A 50% inhibition of DNA synthesis is observed in A431 cells treated with 0.13 nM AR.

Normal rat kidney NRK-SA6 cells ordinarily do not form colonies in soft agar. However, the combination of exogenous EGF and TGF-β added to the culture medium of these cells induces anchorage-independent growth, indicating a transformed phenotype. A combination of exogenous AR and TGF-β also induces the anchorage-independent growth of NRK-Sa6 cells, albeit at a lower level (see Table V), providing direct evidence that AR and EGF are functionally related.

The synergistic action of AR with TGF-β strongly implicates AR as an important factor in the regulation of cell growth. Thus, the present invention provides research tools previously unavailable for investigating the complex and emerging story of normal cell growth control and the characteristic loss of growth control in neoplastic cells.

AR also induces the proliferation of human foreskin fibroblasts (Table IV). A two fold increase in DNA synthesis in these cells was observed at about 50 pM concentration of AR. A maximum stimulation of about six-fold occurs at approximately 5 nM.

The mechanism by which AR signals cell proliferation or growth inhibition is not known. However, preliminary studies aimed at characterizing AR-receptor binding suggest that AR may have a specific receptor. AR competes with EGF for binding to the EGF-receptor and may also compete with EGF for binding to other common receptors, including possibly the AR-specific receptor itself. It is known that ligand binding to the EGF receptor initiates a growth stimulatory signal, in part, by activating tyrosine kinase activity. Binding of AR to the EGF receptor may similarly initiate a proliferative response or, conversely, may block the initiation of a proliferative signal by limiting the number of EGF-receptors available for binding EGF or other signal-generating ligands.

Alternatively, another mechanism by which AR inhibits cell growth is possible and is suggested by the data presented in Table I. Four clones of the A431 cell line, having variable EGF binding sites per cell, were tested for sensitivity to AR inhibitory activity. The observed lack of correlation between AR sensitivity and the number of EGF binding sites per cell suggests that the growth inhibitory signal generated by AR is initiated by a receptor binding event which does not involve the EGF receptor. Such an event may antagonize growth proliferative signals generated by other growth factors such as, for example, TGF-α. Thus, AR may exert its anti-proliferative effect by specifically blocking a cell's mitogenic response to TGF-α or other autocrine growth factors.

AR is an extremely hydrophilic protein, the amino acid sequence of which generates a unique hydropathy profile bearing little similarity to the profiles for the other EGF-family proteins (FIG. 11). AR is a basic protein with a PI of 7.6 to 8.0.

5.4.1. Characterization of Ar Induction of Tpa

TPA induces a pleiotropic response on cells, including changes in cell morphology, cell proliferation and differentiation, membrane transport, receptor-ligand interactions, protein phosphorylation, and phospholipid metabolism. Protein kinase C (PKC) is a $Ca^{2+}$ and phospholipid-dependent protein kinase which functions as a receptor for TPA. Binding of TPA to PKC results in the phosphorylation of numerous substrates including growth factor receptors, cytoskeletal proteins and trans-activating regulatory proteins.

c-AMP is another regulatory molecule which exerts diverse effects on cells, primarily through cAMP-dependent protein kinase A. Intracellular levels of cAMP are regulated by a combination of receptor-mediated activation and adenylate cyclase inhibition. Some studies indicate that TPA and cAMP induced gene expression may converge as a common pathway. To study the regulation of AR gene expression, we chose to look at the effect of various activators or inhibitors of both these regulatory pathways on the production of AR specific RNA in MCF-7 cells.

Forskolin is a drug which activates adenylate cyclase, resulting in increased intracellular cAMP. When administered to MCF-7 cells at 25 uM for 4 hours, a marked stimulation of AR mRNA was observed, suggesting cAMP pathways also play a role in the regulation of AR expression.

5.5. Amphiregulin-Related Derivatives, Analogues, and Peptides

The production and use of derivatives, analogues, and peptides related to AR are also envisioned and are within the scope of the invention. Such derivatives, analogues, and peptides which exhibit growth modulatory activity may find applications in the diagnosis, prognosis, and treatment of a wide variety of neoplasias. Such derivatives, analogues, or peptides may have enhanced or diminished biological activities in comparison to native AR and/or may expand or limit the AR GIA-susceptible cell range and still be within the scope of the invention. Similarly, the production and use of derivatives, analogues, and peptides related to AR which exhibit enhanced or diminished growth stimulatory activity and/or which expand or limit the range of cells responsive to AR's growth stimulatory activity may find useful applications including, but not limited to, the treatment of wounds and burns.

AR-related derivatives, analogues, and peptides of the invention may be produced by a variety of means known in the art. Procedures and manipulations at the genetic and protein levels are within the scope of the invention.

At the protein level, numerous chemical modifications could be used to produce AR-like derivatives, analogs, or peptides by techniques known in the art, including but not limited to specific chemical cleavage by endopeptidases (e.g. cyanogen bromides, trypsin, chmotripsin, V8 protease, and the like) or exopeptidases, acetylation, formylation, oxidation, etc.

5.6. Anti-Amphiregulin Antibody Production

Also within the scope of the invention is the production of polyclonal and monoclonal antibodies which recognize Amphiregulin, or related proteins.

Various procedures known in the art may be used for the production of polyclonal antibodies to epitopes of AR. For the production of antibodies, various host animals can be immunized by injection with the AR protein, or a synthetic AR peptide, including but not limited to rabbits, mice, rats, etc. Various adjuvants may be used to increase the immunological response, depending on the host species, including but not limited to Freund's (complete and incomplete), mineral gels such as aluminum hydroxide; surface active substances such as lysolecithin, pluronic polyols, polyanions, peotides, oil emulsions, keyhole lympet hemocyanins, dinitrophenol, and potentially useful human adjuvants such as BCG (bacille Calmette-Guerin) and *Corynebacterium parvum*.

A monoclonal antibody to an epitope of AR can be prepared by using any technique which provides for the production of antibody molecules by continuous cell lines in culture. These include but are not limited to the hybridoma technique originally described by Kohler and Milstein (1975, Nature 256, 495-497), and the more recent human B-cell hybridoma technique (Kosbor et al., 1983, Immunology Today 4:72) and EBV-hybridoma technique (Cole et al., 1985, Monoclonal Antibodies and Cancer Therapy, Alan R. Liss, Inc., pp. 77-96).

Antibody fragments which contain the idiotype of the molecule could be generated by known techniques. For example, such fragments include but are not limited to: the F(ab')$_2$ fragment which can be produced by pepsin digestion of the antibody molecule; the Fab' fragments which can be generaged by reducing the disulfide bridges of the F(ab')$_2$ fragment, and the two Fab or Fab fragments which can be generated by treating the antibody molecule with papain and a reducing agent.

Antibodies to AR may find use in the qualitative and quantitative detection of mature AR and its precursor and subcomponent forms, in the affinity purification of AR proteins, and in the elucidation of AR biosynthesis, metabolism and function. Antibodies to AR may also be useful as diagnostic and therapeutic agents.

5.7. Uses of Amphiregulin

The bifunctional nature of AR provides for a wide variety of uses in vitro and in vivo. Any compound which includes AR, or fragments and derivatives thereof which exhibit growth inhibitory and/or growth stimulatory activity, either alone or in conjunction with other biologically active growth factors, inhibitors, or immunomodulatory agents, may be employed in the practice and method of the invention.

The localization of the AR gene to a region involved in lymphocyte differentiation suggests AR may play a role in hematopoeitic cell development, activation or immunosuppression. This function is also supported by the homology between the AR3-untranslated region and similar regions from other cytokines.

The subject compounds may be used in the modulation of angiogenesis, bone resorption, immune response, and synaptic and neuronal effector functions. AR may also be used in the modulation of the arachidonic acid cascade. Enzymatic oxidation of arachidonic acid leads to a multitude of important products such as prostaglandins, thromboxanes, prostacyclins, and leukotrienes. Such products are extremely potent, ubiquitous agents with numerous physiological effects including, for example, muscle contraction, platelet aggregation, leukocyte migration, and gastric secretion. AR, AR-related molecules, and compositions thereof may be especially useful in the treatment of wounds and in the diagnosis and treatment of cancer.

5.7.1. Treatment of Wounds

AR may be used in a method for treating wounds, such as cutaneous wounds, corneal wounds, and various other epithelial and stromal disruptions, such as chronic ulcers, burns, surgical incisions, traumatic wounds, and injuries to the hollow, epithelial-lined organs, such as the esophagus, stomach, large and small intestines, mouth, and genital and urinary tracts. The method relies on the topical application of a treatment composition including AR in a physiologically-acceptable carrier.

The compositions of the present invention may be used for treating a wide variety of wounds including substantially all cutaneous wounds, corneal wounds, and injuries to the epithelial-lined hollow organs of the body. Wounds suitable for treatment include those resulting from trauma such as burns, abrasions, cuts, and the like as well as from surgical procedures such as surgical incisions and skin grafting. Other conditions suitable for treatment with the compositions of the present invention include chronic conditions, such as chronic ulcers, diabetic ulcers, and other non-healing (trophic) conditions.

AR may be incorporated in physiologically-acceptable carriers for application to the affected area. The nature of the carriers may vary widely and will depend on the intended location of application. For application to the skin, a cream or ointment base is usually preferred; suitable bases include lanolin, Silvadene (Marion) (particularly for the treatment of burns), Aquaphor (Duke Laboratories, South Norwalk, Conn.), and the like. If desired, it will be possible to incorporate AR containing compositions in bandages and other wound dressings to provide for continuous exposure of the wound to the peptide. Aerosol applications may also find use.

The concentration of AR in the treatment composition is not critical but should be enough to induce epithelial cell proliferation. The compositions may be applied topically to the affected area, typically as eye drops to the eye or as creams, ointments or lotions to the skin. In the case of the eyes, frequent treatment is desirable, usually being applied at intervals of 4 hours or less. On the skin, it is desirable to continually maintain the treatment composition on the affected area during the healing, with applications of the treatment composition from two to four times a day or more frequently.

The amount employed of the subject polypeptide will vary with the manner of administration, the employment of other active compounds, and the like, generally being in the range of about 1 $\mu$g to 100 $\mu$g. The subject polypeptide may be employed with a physiologically acceptable carrier, such as saline, phosphate-buffered saline, or the like. The amount of compound employed will be determined empirically, based on the response of cells in vitro and response of experimental animals to the subject polypeptides or formulations containing the subject polypeptides.

AR compounds may find use alone or in combination with other growth factors, inhibitors or immunomodulators.

5.7.2 Diagnosis and Treatment of Neoplasias

The compositions of the present invention may be useful in the diagnosis, prognosis, and treatment of a wide variety of neoplasias.

A number of diagnostic uses of AR and related molecules are envisioned. In the practice of the invention, the subject polypeptides may be joined to a label, such as a radioisotope, enzyme, fluorescer, chemiluminescer, enzyme fragment, particle, etc. Such compounds may be used to titrate the number of receptors for AR on a cell. Identification of receptors for AR is an indication of potential responsiveness of the cell to the bilogical effects of AR and related molecules. AR, AR-related molecules, and/or antibodies thereto may be used in competitive assays for detection of AR in media, particularly in physiological media. A wide variety of diagnostic assays known in the art may be used.

The presence and levels of AR in body fluids and tissues may directly or inversely relate to the presence and pervasiveness of certain cancers. Assays which can detect and/or quantify AR may find use in cancer diagnosis and prognosis. (See Section 5.6, supra).

The present invention also relates to the detection of AR mRNA. Assays which utilize nucleic acid probes to detect sequences comprising all or part of a known gene sequence are well known in the art and may be used. AR mRNA levels may indicate emerging or existing neoplasias and, therefore, assays which can quantify AR mRNA levels provide a valuable diagnostic tool.

In addition, malignant cells expressing the AR receptor may be detected by using labeled AR or AR-related molecules in a receptor binding assay, or by the use of antibodies to the AR receptor itself. Cells may be distinguished in accordance with the presence and density of receptors for AR, thereby providing a means for predicting the susceptibility of such cells to the biological activities of AR.

AR may be used as an anti-neoplastic compound. For in vivo use, the subject compositions may be administered in a variety of ways, including but not limited to, injection, infusion, topically, parenterally, etc. Administration may be in any physiologically acceptable carrier, including phosphate buffered saline, saline, sterilized water, etc. AR and related molecules may also be encapsulated in liposomes and may be conjugated to antibodies which recognize and bind to tumor or cell specific antigens, thereby provided a means for "targeting" the compositions of the invention.

AR may be useful in vivo for inducing terminal differentiation in tumor cells. Such cells have diverted from the ordinary course of cell differentiation characteristic of normal cells and are capable of continued proliferation. Normal cells, in contrast, differentiate into cells which are incapable, under most circumstances, of further cell division. Thus, the ability of AR to reactivate normal cell differentiation in tumors and, ultimately, to arrest continued tumor growth may find valuable use in tumor therapy regimens.

AR and related derivatives, analogues, and peptides thereof may be used alone or with at least one other anti-proliferative compound, including, for example, an interferon, TGF-$\beta$1, TGF-$\beta$2, tumor necrosis factor-$\beta$, tumor necrosis factor-$\alpha$, etc., in the treatment of hormonally responsive carcinomas which may affect a wide variety of organs, such as the lungs, breast, prostate, colon, etc. Hormonally responsive carcinomas can also be treated by inducing production of AR in the carcinoma cells. Inducers include but are not limited to estrogens such as 17-B estradiol, compounds with estrogenic activity, and compounds with anti-estrogenic activity such as Tamoxifen. Any combination of these compounds may also be used as an inducer.

The compounds of the invention may be used in vitro to inhibit the growth of cells or cell lines sensitive to AR as distinguished from cells which are not sensitive. In this way, heterogeneous mixtures or cell lines can be freed of undesirable cells, where the undesirable cells are sensitive to AR's growth inhibitory activity. For example, the compounds of the invention may be used in vitro to eliminate malignant cells from marrow for autologous marrow transplants, and to eliminate or inhibit the proliferation of malignant cells in blood prior to reinfusion.

The most effective concentration of AR for inhibiting proliferation of a given cell may be determined by adding various concentrations of AR to the tumor cell of interest and monitoring the amount of ininhibition of cell proliferation. The most effective concentration of individual inducers and/or combinations of inducers may be determined by monitoring the production of AR in the carcinoma cells.

6. EXAMPLE: PRODUCTION, PURIFICATION, AND CHARACTERIZATION OF HUMAN AMPHIREGULIN

The subsections below describe the purification and characterization of Amphiregulin produced by MCF-7 cells treated with TPA.

6.1. Materials and Methods

The following procedures were used to induce AR synthesis in MCF-7 cells and to prepare and characterize substantially pure AR.

6.1.1. Sds-Polyacrylamide Gel Electrophoresis

Proteins were analyzed on SDS-PAGE slab gels (normal or mini Bio-Rad system) as described (Laemmli, 1970, Nature 227: 680–685), and were detected by silver staining (Merril et al., 1981, Science 211: 1437–1439).

6.1.2. Isoelectricfocusing

Isoelectric focusing was performed essentially as described by the Isolab Technical data sheet for Resolve IEF gels. Briefly, samples were loaded onto precast agarose gels (85×100 mm, pH 3–10) and were focused on a Resolve model FR-2500 isoelectricfocusing unit using a Bio-Rad model 3000 Xi computer-controlled electrophoresis power supply. Bio-Rad IEF standards were focused alongside the sample, stained, and the dry gel exposed to Kodak X-Omat AR film with a DuPont Cronex lightening plus intensifier screen.

6.1.3. Iodination of Protein

Proteins were labeled with $^{125}$I using the chloramine T method (Barridge, 1978, Methods Enzymol. 50: 54–65).

6.1.4. Protein Determination

Protein concentrations were determined by absorption at various wavelengths (210 to 280 nm). The methods of Lowry (Lowry et al., 1951, J. Biol. Chem. 193: 265–275) and Bradford (1976, Anal. Biochem. 72: 248–252) were used with bovine serum albumin as a standard.

6.1.5. $^{125}$I-EGF Binding Assay

The binding assays were performed either in 48 well tissue culture plates, when freshly grown and/or formalin fixed A431 cells were used as described (Carpenter, et al., 1979, J. Biol. Chem. 245, 4484—4891; Shoyab, et al., 1979, Nature 279: 387–391; DeLarco, et al., 1980, J. Biol. Chem. 255: 3685–3690), or by immobilizing plasma membranes onto 96-well polyvinyl chloride plates as described (Kimball and Warren, 1984, Biochem. Biophys. Acta 771: 82–88).

6.2. Production of Amphiregulin

6.2.1. Collection of Conditioned Media from TPA Treated MCF-7 Cells

MCF-7 cells were cultured in T 150 Corning tissue culture flasks in a total volume of 25 ml of 50% IMDM (Iscove's Modified Dulbecco's Media)+50% DMEM containing 0.6 µg/ml of insulin and 15% heat inactivated fetal bovine serum (MCF-7 complete media). Approximately $1 \times 10^6$ cells were seeded per flask and incubated at 37° C. with 5% $CO_2$. On day six, all media was removed and 20 ml of fresh MCF-7 complete media containing 100 ng/ml of TPA was added to each flask. Forty-eight hours later, the media was removed and each flask rinsed with 15 ml of 50% IDMM+50% DMEM (serum-free media) and 25 ml of fresh serum free media was added to each flask and incubated at 37° C. with 5% $CO_2$. Four days later, the conditioned serum-free media was collected, centrifuged to remove debris, and stored at −20° C. Flasks were again fed with 25 ml of serum-free media and conditioned serum-free media was collected every third or fourth day. An aliquot of the conditioned media from each collection was assayed for growth inhibitory activity (GIA) on A431 human epidermoid carcinoma cells. Usually, three to four rounds of conditioned media were collected from each batch of TPA treated MCF-7 cells.

6.2.2. Isolation of Crude AR

About 4500 ml conditioned media was thawed and centrifuged at 4° C. for 15 min at 3500 rpm. The supernatant was concentrated in an Amicon 2-liter concentrator using a YM10 membrane (Amicon) at 4° C. When volume of retenate became about 200 ml, 1000 ml of cold Mili-E-Q water was added and the mixture was reconcentrated to 200 ml.

The concentrate was removed and transferred to a pre-cooled 250 ml Corning centrifuge bottle. Concentrated acetic acid was slowly added with stirring to a final concentration of 1 M acetic acid. The mixture was allowed to stand for 1 h at 4° C. and centrifuged for 20 min at 40,000×g at 4° C. in a Sorval RC-5B centrifuge. The supernatant was removed and stored at 4° C. The pellet was suspended in 30 ml of 1 M acetic acid and recentrifuged as described above. The supernatant was again carefully removed and pooled with the first supernatant and then dialyzed against 17 liters of 0.1 M acetic acid in No. 3 spectrapore dialysis tubing (molecular weight cut off approximately 3000). The dialysis buffer was changed three times over a two day period. The retenate was lyophilized. The dry material was removed, pooled, weighed and stored at −20° C. till further use. We call this material crude powder.

6.3 Purification of Amphiregulin

6.3.1 Reversed Phase Liquid Chromatography 950 mg of crude powder (from approximately 9 liters of serum-free conditioned media) was suspended in 300 ml of 0.1% TFA (Trifluoroacetic-acid) and centrifuged for 20 min at 7,000×g. The supernatant was carefully removed and applied on a column of preparative C18 (2.54 cm×27 cm; 55-105 microns; Waters) equilibrated with 0.1% TFA in water. The chromatographic support was suspended in acetonitrile (MeCN) with 0.1% TFA, the slurry was poured into a 2.54 cm diameter column, and the column was washed with 400 ml of MeCN with 0.1% TFA and then equilibrated with 600 ml of 0.1% TFA in water. The flow rate was 4 ml/min and the chromatography was carried out at room temperature. The column was washed with 650 ml of 0.1% TFA in water. The breakthrough and wash were collected together. Then stepwise elution was performed as follows: (1) 650 ml of 20% MeCN/$H_2O$ with 0.1% TFA, (2) 650 ml of 40% MeCN/$H_2O$ with 0.1% TFA, (3) 650 ml of 60% MeCN/$H_2O$ with 0.1% TFA, and (4) 650 ml of 100% MeCN with 0.1% TFA. An aliquot was taken from each fraction and tested for GIA. About 77% of total GIA activity appeared in the breakthrough and wash fractions.

Breakthrough and wash fractions were injected isocratically onto a preparative Partisil 10 ODS-3 column (10 micron, 2.2×50 cm, Whatman) attached to a high performance liquid chromatography (HPLC) system (Waters). The flow rate was set at 4 ml/min. Once the sample had passed on to the column, the column was washed with 250 ml of 0.1% TFA in water. The linear gradient was generated between the primary solvent, 0.1% TFA in water, and the secondary solvent, acetonitrile containing 0.1% TFA. The gradient conditions were: 0 to 15% in 10 min, 15 to 15% in 30 min, 15 to 25% in 150 min, 25 to 65% in 100 min, and 65 to 100% in 10 min. All solvents were HPLC grade. Fractions of 14 ml were collected and aliquots of each fraction were assayed for GIA. Two broad peaks of activity were seen (FIG. 1). The early eluting peak (eluted between 20-23% of acetonitrile) was further purified and characterized.

Fractions 47 to 62 were pooled. 224 ml of 0.1% TFA in water was added to the pooled fraction. The mixture was isocratically injected onto a semi-preparative µ-Bondapak-C18 column (7.8×300 mm, Waters) at a flow rate of 2 ml/min at room temperature. The linear gradient conditions were 0 to 17% in 10 min, 17 to 17% in 30 min, 17 to 25% in 320 min, and 25 to 100% in 40 min. The flow rate was 1 ml/min during gradient and 4 ml fractions were collected. Aliquots were taken and assayed for GIA. Two major peaks of activity were observed eluting at acetonitrile concentrations of approximately 20% and 21% respectively (FIG. 2).

Fractions 49-53 were pooled. 20 ml of 0.1% TFA was added to the pooled fraction. The mixture was isocratically applied onto a µ-Bondapak-C18 column (3.9×300 mm, Waters) at a flow rate of 1 ml min at room temperature. The gradient conditions were 0–18% in 10 min, 18–18% in 30 min, 18–25% in 280 min, and 25–100% in 20 min. the flow rate was 0.4 ml/min and 2 ml fractions were collected. Most of the activity emerged from the column at about 21.5% acetonitrile concentration (FIG. 3A). Fractions 54–59 (FIG. 2) were pooled and chromatographed exactly as described above in FIG. 3A. Most of the activity eluted from the column at an acetonitrile concentration of approximately 22.2% (FIG. 3B).

6.3.2. Gel Permeation Chromatography

Figure 4B:
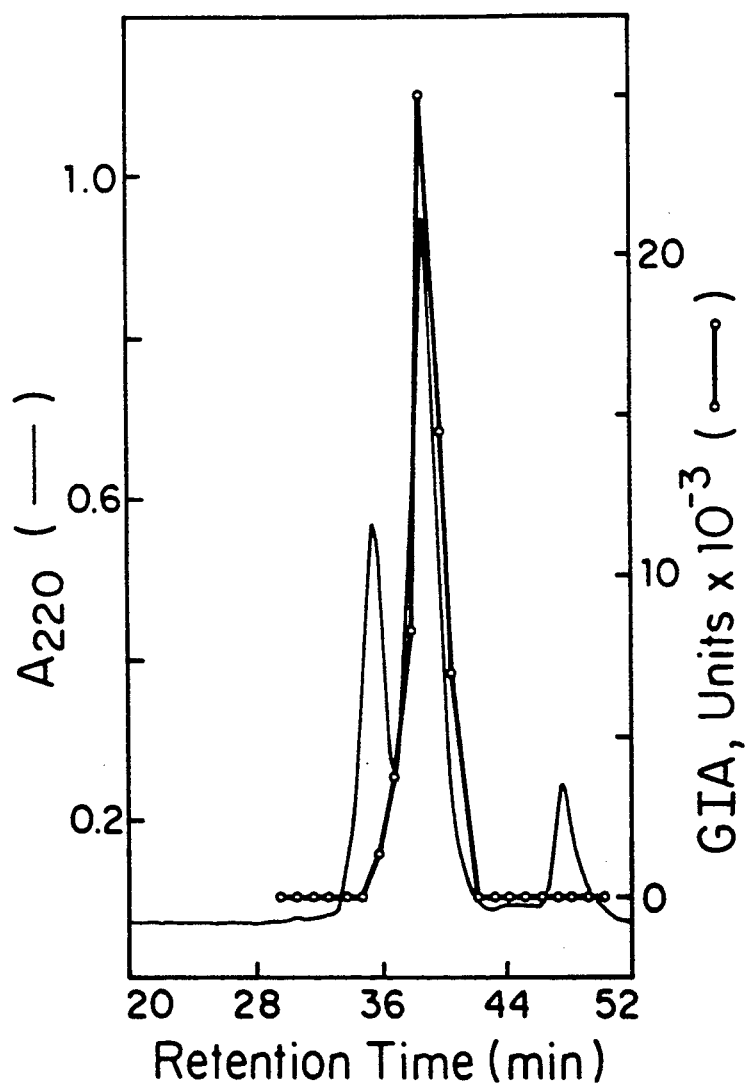
Figure 4C:
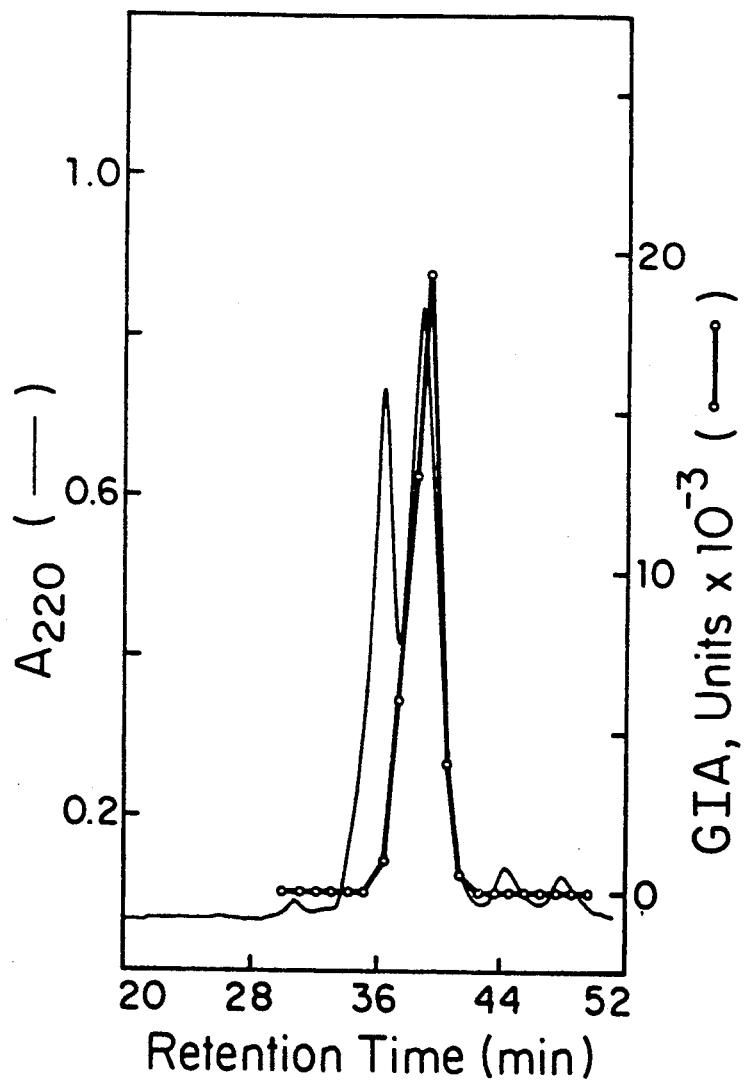

Fractions 35 to 38 (FIG. 3A) were individually concentrated to about 70 µl using a Speed-Vac concentrator (Savant), to which was added an equal volume of acetonitrile containing 0.1% TFA. This 140 µl sample was injected onto two Bio-sil TSK-250 columns (7.5×300 mm each, Bio-Rad) arranged in tandem. The elution was performed isocratically with a mobile phase of 50% acetonitrile/$H_2O$ with 0.1% TFA at room temperature. The flow rate was 0.4 ml/min and chart speed was 0.25 cm/min; 0.4 ml fractions were collected and aliquots were assayed for GIA. Chromatographic profiles of fractions 35, 36, and 37 (FIG. 3A) are shown in FIGS. 4A, 4B, and 4C respectively.

Figure 4D:
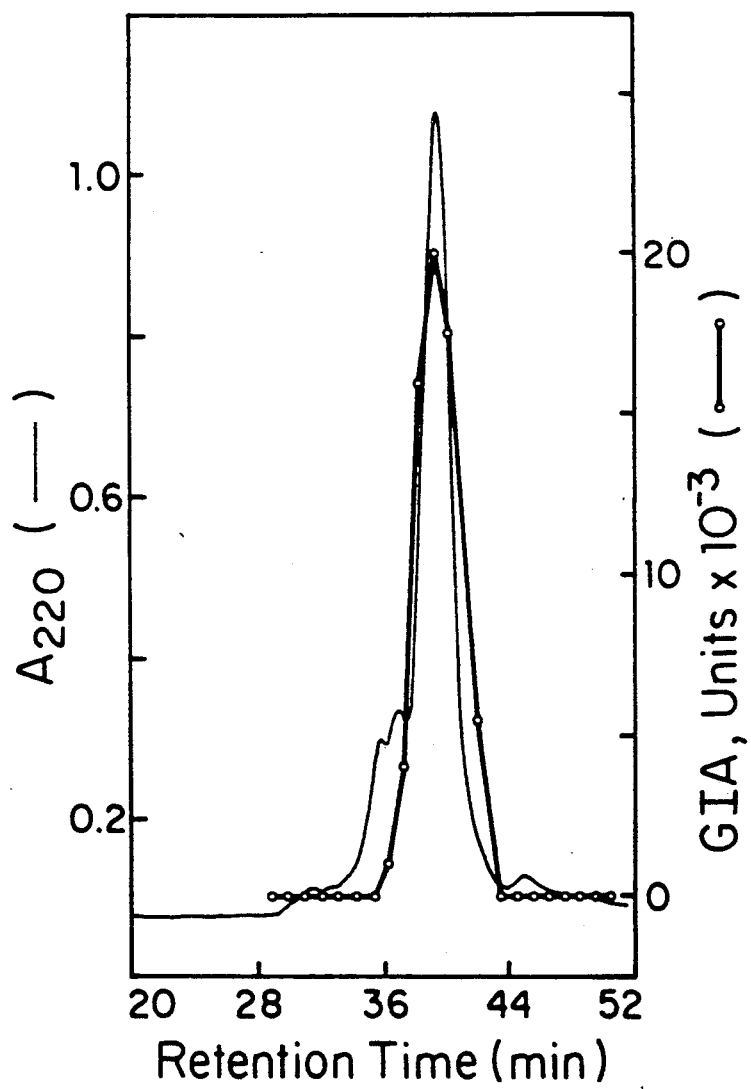

Fractions 41 and 42 (FIG. 3B) were pooled together and concentrated to 70 μl and then subjected to gel permeation chromatography as described above. The chromatographic profile is given in FIG. 4D.

6.4. Cell Growth Assays

6.4.1. Cell Growth Modulatory Assay Using $^{125}$I-Deoxyuridine Incorporation into DNA The assays were performed in 96 flat well plates (Falcon 3072). Human epidermoid carcinoma of vulva cells (A431) were used as test cells for growth inhibitory activity (GIA) and human foreskin fibroblasts (Sadamoto) as indicator cells for growth stimulatory activity (GSA). $3.5 \times 10^4$ cells in 50 μl of DMEM supplemented with 5% heat inactivated fetal bovine serum (FBS), penicillin/streptomycin (PS) and glutamine (test medium) were placed in all wells except peripheral wells. The peripheral wells received 50 μl PBS. Three hours later, 50 μl of test sample in test medium was added to each well, while control wells received only 50 μl of test medium. Three wells were used for each concentration of test sample. Plates were incubated at 37° C. for 2–3 days. After this, 100 μl of a solution of $^{125}$I-iodo-2′-$^{125}$I-deoxyuridine [4 Ci/mg - 0.5 mCi/ml (2 μl/ml in test medium)] was added to each well and plates were incubated at 37° C. After 4–6 hours, the medium was aspirated from the wells, washed once with 200 μl PBS. Then, 200 μl methanol was added to each well, plates were incubated for 10 minutes at room temperature, and methanol removed by aspiration. 200 μl of 1 M sodium hydroxide was added to each well, the plates were incubated for 30 minutes at 37° C. Sodium hydroxide was removed with titertek plugs (Flow Labs). The plugs were transferred into 12×75 mm plastic tubes and counted in a gamma counter to quantify $^{125}$I-IUdR incorporation.

6.4.2. Soft Agar Colony Assay

A 0.5 ml base layer of 0.5% agar (Agar Noble; Difco Laboratories, Detroit, Mich.) in DMEM containing 10% heat inactivated FBS was added to 24 well Costar tissue culture plates. 0.5 ml of 0.3% agar containing the same medium-FBS mixture, $5-10 \times 10^3$ test cells, and the factors to be tested at various concentrations were overlaid on the basal layer of agar. The plates were incubated at 37° C. in a humidified atmosphere of 5% $CO_2$ in air and refed after 7 days by addition of 0.5 ml of 0.3% agar containing the same medium and concentrations of test material. Colonies were enumerated unfixed and unstained and the number of colonies greater than 20 cells were scored between days 7 and 14.

6.4.3. Cell Growth Inhibitory Assay

A431 cells were plated at $2.1 \times 10^4$ cells per well in 0.3 ml medium (DMEM with 10% FBS, P/S, glutamine) in 24 well Costar plates (about 2 $cm^2$/well) and incubated for 2 hours at 37° C. Then, test samples at various concentrations in duplicate in 0.3 ml medium were introduced to each well. The control wells received medium without any sample. Plates were incubated at 37° C. for 72 hours. The medium was then aspirated, the cells were washed with 1 ml PBS/well, detached with 0.5 ml of trypsin (0.5%)-EDTA (0.5 mM) and counted using a Coulter counter.

6.5. Analysis of Ar Primary Structure

6.5.1. Reduction and S-Pyridylethylation

AR (20–30 μg) was dried in 1.5 ml microfuge polypropyline tube, suspended in 100 μl of 3 M urea in 0.05 M TRIS-HCl, pH 7.5. Four μl of 2-mercaptoethanol was added to the mixture, contents mixed, flushed with nitrogen, and incubated at 25° C. After 2.5 h, 4.5 μl of freshly distilled 4-vinylpyridine was added to the mixture, the tube was again flushed with nitrogen and incubated for 2 h at 25° C. The reaction mixture was acidified to pH 2.0 with 10% TFA. S-pyridylethylated AR was purified by rp HPLC using a μ-Bondapak C18 column (3.9×300 mm, Waters). The concentration of acetonitrile was increased linearly (1%/min.) during 55 min., at a flow rate of 1 ml/min. The primary solvent was 0.1% TFA. S-pyridylethylated AR (SPE-AR) eluted at about 26.5% acetonitrile, approximately at 4% higher acetonitrile concentration than untreated AR.

6.5.2. N-Glycanase Treatment

AR or S-pyridylethylated AR (10–20 μg) was dried in 1.5 ml-polypropylene microfuge tube, suspended in 80 μl of 0.1 M phosphate buffer pH 5.5, 10–20 μl of N-Glycanase (0.25 unit/ μl Genzyme) was added, the mixture was incubated for 16 h at 37° C. and 0.9 ml of 0.2% TFA added to the reaction mixture and sample injected onto ultrapore RPSC C3 rp HPLC column (4.6×75 mm, Altex) at a flow rate of 1 ml/min previously equilibrated with the primary solvent 0.1% TFA. Acetonitrile with 0.1% TFA was used as secondary solvent. The concentration of acetonitrile was increased linearly (0.4%/min.) during 85 min. at room temperature. N-deglycosylated-AR and N-deglycosylated S-pyridylethylated AR eluted approximately 16.5 and 20.5% acetonitrile concentration respectively.

6.5.3. Enzymatic Cleavage of N-Glycanase Treated S-Pyridylethylated Ar

Cleavage with endopeptidase Lys-C was done in 60 μl of 0.1 M TRIS-acetic acid buffer, pH 8.0 at 25° C. for 16 h. The enzyme/substrate ratio was 1 to 5 (w/w). Endopeptidase-Arg and S. aureus V8 protease digestions were done in 80 μl of 0.05 M TRIS-HCl, pH 8.0 and 0.1 M ammoniumbicarbonate at 37° C. for 16 h. The enzyme/substrate ratio was again 1 to 5.

6.5.4. Chemical Cleavage

For CNBr cleavage at methionine residue, 5 μg of N-Glycanase treated S-pyridylethylated AR were dried in 1.5 ml polypropylene microfuge tube, suspended in 75 μl of 70% formic acid, then 25 μl of CNBr solution (25 mg/ml in 70% HCOOH) was added, mixed, and tube was flushed with nitrogen. The reaction was carried out for 22 h at 25° C. in dark. The reaction mixture was diluted to 1.1 ml with water and dried in a Speed-Vac concentrator. The dried sample was suspended in 20 μl 2-aminoethanol, allowed to stand for 10 min at 22° C. and then vacuum dried. The mixture was suspended in 0.9 ml of 0.2% TFA.

6.5.5. Peptide Isolation

Peptides were separated on a reverse phase HPLC C8 column (4.6×100 mm, Whatman) attached to a HPLC system (Waters). Acidified sample (pH, 2.0) was applied onto a column equilibrated with 0.1% TFA (primary solvent) at flow rate of 1 min ml and the column was further washed with about 15 ml of 0.1% TFA. Linear gradients were used between the primary solvent and the secondary solvent acetonitrile with 0.1% TFA. The gradient conditions were 0 to 50% in 125 min. at a flow rate of 0.5 ml/min.

6.5.6. Amino Acid Analysis

Dried samples were hydrolyzed with constant boiling HCl (5.7 M, Pierce) containing 1% (v/v) phenol under reduced pressure in a Teflon-sealed glass hydrolysis bulb (Pierce) at 105° C. for 16 h. The hydrolysates were dried in a Speed Vac concentrator (Savant Instruments) and derivitized with phenylisothiocynate for 20 min. at room temp. Phenylthiocarbamyl amino acid derivative were analyzed by rp HPLC on a Octadecyl column (4.5×250 mm, IBM). The linear gradient was performed between primary solvent 0.15 M sodium acetate pH 6.4, 0.05% triethylamine titrated to pH 6.4 with acetic acid and the secondary solvent 60% acetonitrile at a flow rate of 1 ml/min at 38° C.

6.5.7. Amino Acid Sequence Determination

Peptide sequences were determined with an Applied Biosystem model 475 gas phase sequencer as described (Hewick et al., 1981, J. Biol. Chem. 256: 7990-7997). Three precycles of Edman degradation were performed prior to sample application for each run. 25% TFA was used to convert the Triazoline derivatives to phenylthiohydantoin amino acids. Identification of phenyl thiohydantoin amino acids was carried out, on-line, on Model 120A PTH analyzer (Applied Biosystem) as described (Hunkapiller and Hood, 1983, Science 219: 650-659).

6.5.8. Various Treatments 50-100 units of either semipure (semi prep. rp C18 step) or apparently pure AR were used for these experiments (Table 1). N-Glycanase and 0-Glycanase were from Genzyme Corp., Boston; all other enzymes were from Boehringer Mannheim Biochemicals or Worthington Biochemicals. Treatments were carried out in 50-200 µl of appropriate buffer. An excess of enzymes were used, usually 5-20% (w/w) of substrate concentration. After treatments, samples were analyzed for GIA by removing interfering materials by various analytical means. In most cases, sample pH was adjusted to about 2 with 10% TFA. The samples were applied on a reverse-phase ultra-pore RPSC C3 column (4.6×75 mm, Altex) equilibrated with 0.1% TFA. The column was washed further with primary solvent 0.1% TFA. Then elution was started using acetonitrile with 0.1% TFA as a secondary solvent. The gradient conditions were 0 to 50% for 0.2 min and 50 to 50% for 19.8 min. The flow rate was 0.5 ml/min and 2 ml fractions were collected. Aliquots were taken and assayed for GIA. AR activity usually eluted in fraction 4.

6.6. Dna Binding Studies

The binding of AR to native calf thymus DNA cellulose, denatured calf thymus DNA, and cellulose was performed as described (Herick and Alberts, 1971, Methods in Enzymology 21:198). Celluloses (10 mg) were rehydrated in 500 µl loading buffer (20 mM Tris pH 7.4, 10% glycerol, 1 mM EDTA, 1 mM β-mercaptoethanol, 100 µg/ml BSA, and 50 mM NaCl). Reactions were carried out in duplicate in 1.5 ml eppendorf tubes with 300 µl hydrated (packed volume) cellulose samples washed 5 times with loading buffer. Then, 0.2 ng of $^{125}$I-AR specific activity of 425 µCi/µg) or other $^{125}$I-labeled protein in 250 µl loading buffer was added to each tube. Samples were mixed and incubated at 4° C. for 20 min with periodic agitation and then washed 5 times with 200 µl loading buffer per wash. Elution was performed stepwise with 0.1 M, 0.15 M, 0.25 M, 0.6 M, 1 M and 2 M NaCl in loading buffer (5 times with 200 µl at each concentration). Specifically bound material was defined as that eluting at a concentration of 0.25 M NaCl or greater. Material eluting at a concentration of 0.15 M NaCl or less was considered non-specifically bound.

6.7. Results

6.7.1. Production of AR by Tpa Treated Mcf-7 Cells

MCF-7 cells grown on a plastic substratum exhibit typical epitheloid features: cells are small and polygonal in shape. TPA induces dramatic morphological changes in a dose-dependent manner. Following TPA treatment, MCF-7 cells lose their well defined morphology, become rounded, and spread out. TPA elicits a dose-dependent reduction in cell number and an increase in cell volume compared to untreated cells.

Serum-free conditioned media from MCF-7 cells did not contain any detectable growth inhibitory activity for A431 cells. However, serum-free supernatants collected from MCF-7 cells treated with TPA for 2-3 days were found to inhibit the proliferation of A431 epidermoid carcinoma cells. The optimum induction of inhibitory activity was observed between 25 to 100 ng/ml TPA. Even after removing TPA, TPA treated MCF-7 cells secreted this activity in serum free medium for at least eight days. Although a reduction in growth inhibitory activity was noticed with time after TPA removal, these results indicate amphiregulin that induced or increased in expression in MCF-7 cells that have been treated with TPA.

6.7.2. Initial Characterization

Table I summarizes the effect of various physical, chemical, and enzymatic treatments on the antiproliferative activity of amphiregulin. The GIA (growth inhibitory activity) of amphiregulin was resistant to treatment of 1 M acetic acid, 1 M ammonium hydroxide, 6 M urea, 0.01 M sodium metaperiodate, heating at 56° C. for 30 minutes, and treatments with neuraminidase, N-Glycanase, O-Glycanase, Lipase, phospholipase A2, C or D. However, activity was sensitive to heating at 100° C. for 10 minutes, to reduction, to reduction and 4-vinylpyridine treatment, and to digestion with proteinases such as Trypsin, endopeptidase Lys-C, endopeptidase-Arg and endopeptidase-Glu (V-8). These results suggest that amphiregulin is a protein containing cysteins in disulfide linkage(s) which are essential for its biological activity. This protein may contain oligosaccharides- and/or lipo-moieties that are not obligatory for the biological activity.

TABLE II

| Effects of Various Treatments on GIA of Amphiregulin | |
|---|---|
| Treatment | Percent Control |
| 1M Acetic acid for 2 h at 4° C. | 102 |
| 1M NH4OH for 2 h at 4° C. | 97 |
| 56° for 30 min | 96 |
| 100° for 10 min | 5 |
| 6M urea (2 h at 25° C.) | 82 |
| 0.2M 2-mercaptoethanol (2.5 h at 25° C.) | 6 |
| 2-mercaptoethanol + 4 vinylpyridine | 1 |

TABLE II-continued
Effects of Various Treatments on GIA of Amphiregulin

| Treatment | Percent Control |
|---|---|
| (2.5 h at 25° C.) + (2 h at 25° C.) | |
| 0.01M Sodium metaperiodate (6 h at 4° C. in dark) | 86 |
| TPCK - trypsin (6 h at 37° C.) | 3 |
| TPCK-trypsin + soybean trypsin inhibitor (6 h at 37° C.) | 82 |
| Soybean trypsin inhibitor (6 h at 37° C.) | 109 |
| Endopeptidase Lys-C (20 h at 25° C.) | 5 |
| Endopeptidase Arg (16 h at 37° C.) | 4 |
| Endopeptidase Glu (16 h at 37° C.) | 6 |
| Neuraminidase (16 h at 37° C.) | 103 |
| N-Glycanase (16 h at 37° C.) | 90 |
| O-Glycanase (16 h at 37° C.) | 102 |
| Neuraminidase + N-Glycanase (16 h at 37° C.) | 94 |
| Neuraminidase + O-Glycanase (16 h at 37° C.) | 105 |
| Phospholipase A2 (6 h at 37° C.) | 82 |
| Phospholipase C (6 h at 37° C.) | 95 |
| Phospholipase D (6 h at 37° C.) | 80 |
| Lipase (6 h at 37° C.) | 111 |

6.7.3. Purification of Amphiregulin

A summary of amphiregulin purification is presented in Table III. A 1,842-fold purification with 5.1% yield has been achieved for TSK 250-I fraction and a 2,270-fold purification with 1.7% yield has been obtained for TSK 250-II fraction. The method is reproducible. We have purified amphiregulin on four different occasions with similar results. The specific activity of purified amphiregulin falls into a range of 2.7 to $3.4 \times 10^6$ units/mg protein. Purified amphiregulin from the TSK-250-I column having a specific activity of about $3.0 \times 10^6$ was used for structural determinations and other biochemical studies.

TABLE III
Summary of Purification of Amphiregulin (GIA)

| Fraction | Volume (mL) | Protein (μg) | GIA* (units × 10$^{-3}$) | Specific Activity Units × 10$^{-3}$ per mg | Yield % | Purification (fold) |
|---|---|---|---|---|---|---|
| Crude | 300 | 916,600 | 1363 | 1.49 | 100 | 1 |
| Prep. C18 Flow-thru and wash | 950 | 532,000 | 1052 | 1.98 | 77.2 | 1.3 |
| Prep. rp. ODS | 225 | 2,281 | 286 | 125.43 | 21.0 | 84.2 |
| Semi prep. rp. C18-I | 20 | 339 | 97 | 286.14 | 7.1 | 192.0 |
| -II | 20 | 235 | 92 | 391.49 | 6.7 | 262.7 |
| Anal rp. C18-I | 6 | 242 | 50 | 206.61 | 3.7 | 138.7 |
| -II | 6 | 173 | 46 | 265.89 | 3.4 | 178.4 |
| TSK 250-I | 3.6 | 25.5 | 70 | 2,745.10 | 5.1 | 1,842.3 |
| I-A | 1.6 | 6.6 | 15 | 2,272.73 | 1.1 | 1,525.3 |
| I-B | 1.2 | 11.4 | 33 | 2,894.74 | 2.4 | 1,942.8 |
| I-C | 0.8 | 7.5 | 22 | 2,933.33 | 1.6 | 1,968.7 |
| TSK 250-II | 1.2 | 6.8 | 23 | 3,382.35 | 1.7 | 2,270.0 |

*The details are given in Section 6.1.3, and its subsections, supra. One unit of GIA was defined as the amount of factor required to inhibit $^{125}$I-deoxyuridine incorporation into A431 cells by 50%.

Figure 5B:
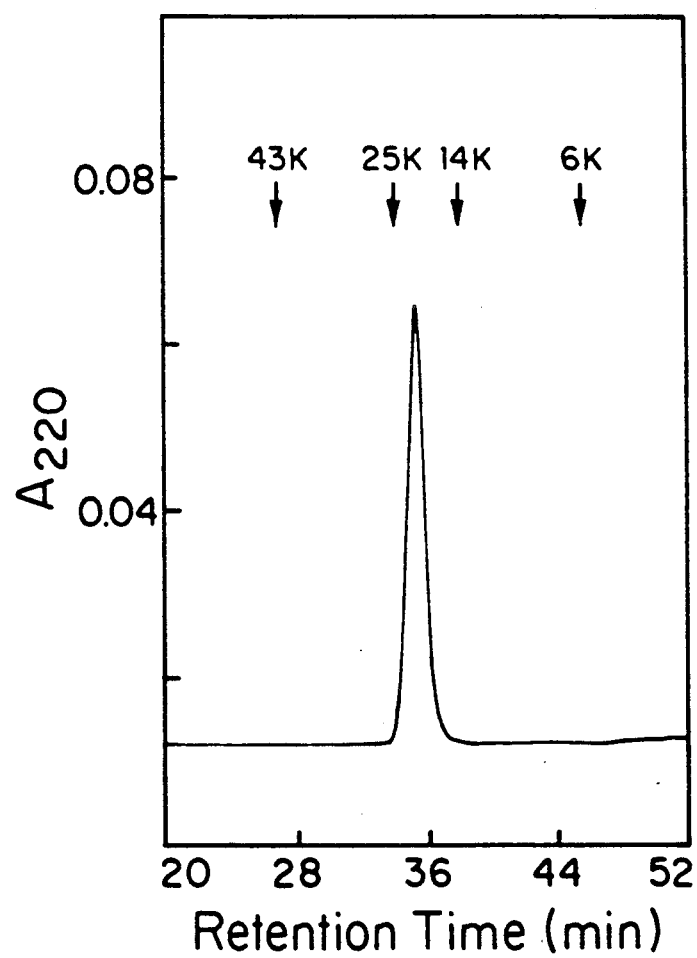

6.7.4. Analysis of Amphiregulin (AR) and S-Pyridylethylated Amphiregulin (Spe-Ar) by Hplc Gel permeation chromatography of AR and SPE-AR on a TSK 250 column (7.5×600 mm, Bio-Rad) is shown in FIG. 5A and 5B respectively. The activity coeluted with the protein peak (5A). The molecular weight of AR and SPE-AR was determined from the data in FIG. 5 and found to be approximately 14,000 and 17,000 respectively. Calculated molecular weights for the structures of truncated AR and AR shown in FIG. 12 are approximately 8500 and 9100 daltons respectively.

AR and SPE-AR eluted as symmetrical single peaks from an ultrapore RPSC C3 rp HPLC column (4.6×75 mm, Altex) (FIG. 6A and B). The GIA coeluted with protein peak (FIG. 6A). SPE-AR eluted at about 21% of acetonitrile concentration, approximately 4% higher acetonitrile concentration than the untreated protein. These results suggest that AR is rich in cysteine residues which are modified by 4-vinyl pyridine, thus making AR more hydrophobic concomitantly eluting at a higher concentration of acetonitrile.

6.7.5. Sds-Page Analysis of Ar

Figure 7A:
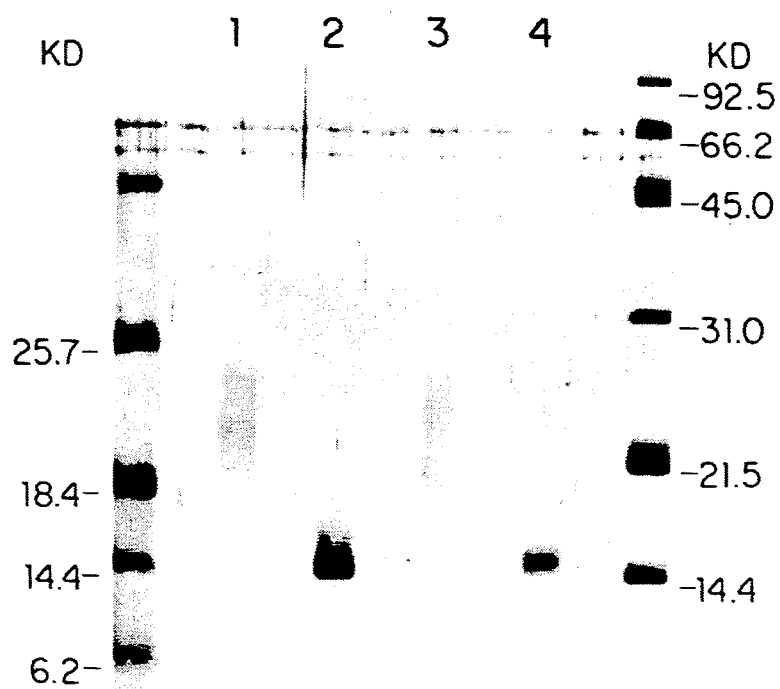

FIG. 7A shows an analysis of AR, N-Glycanase-treated AR (NG-AR), SPE-AR, and N-Glycanase-treated SPE-AR (NG-SPE-AR) in 15% acrylamide under reducing conditions (FIG. 7A). AR and SPE-AR migrated in the gel as a broad, diffused single band with median relative molecular weight of 22,500 within a range of about 20,000 to 25,000 (Lanes 1 and 3). The treatment of AR and SPE-AR with N Glycanase resulted in the faster migration of these proteins. NG-AR and NG-SPE-AR migrated as a single band with median molecular weights of 14,000 and 14,500 daltons, respectively. Similar results were observed when proteins were run in 15% gel under non-reducing conditions (data not shown). The treatment of AR with neuraminidase, O-Glycanase, or neuraminidase and O-glycanase together, did not alter its electrophoretic mobility in gel either in reducing or non-reducing conditions. Thus, AR is a single chain glycoprotein containing N-linked oligosaccharide chain(s) which are not required for GIA of AR in vitro.

Figure 7B:
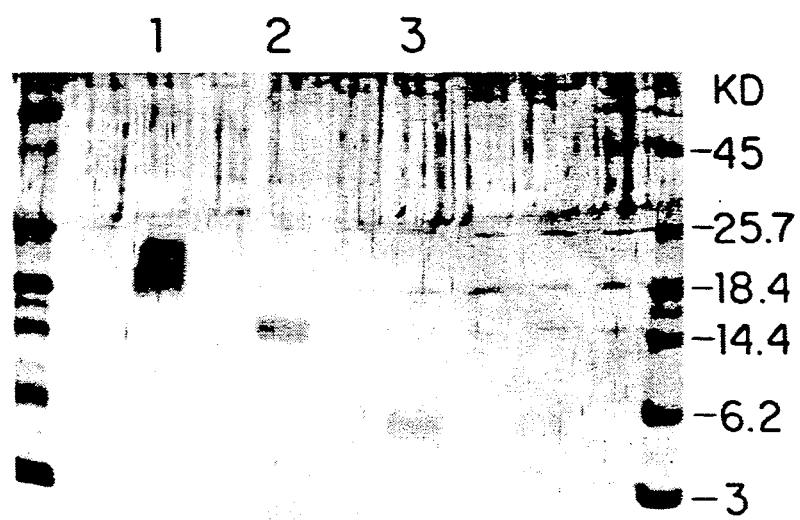

The treatment of NG-AR or AR with phospholipase D (PLD) (cabbage) resulted in the reduction of GIA to 80% of control. PLD treated NG-AR was subjected to rp-HPLC on a C3 column and purified active peaks were analyzed on 20% SDS-PAGE (FIG. 7B). A single band of Mr 5600 was observed. These results indicate that PLD or some contaminating protease(s) in the PLD preparation convert AR to active fragment(s).

6.7.6. Isoelectrofocusing (IEF) Analysis of Ar

IEF analysis of $^{125}$I-labeled AR was carried out as described in Section 6.1.1.2, supra. AR focused as a single broad band with P$_I$ between 7.6 and 8 (FIG. 8). NG-AR focused as a single band with PI of about 8.05. Thus AR is a basic single chain N-linked glycoprotein.

6.7.7. Biological Properties

Figure 9A:
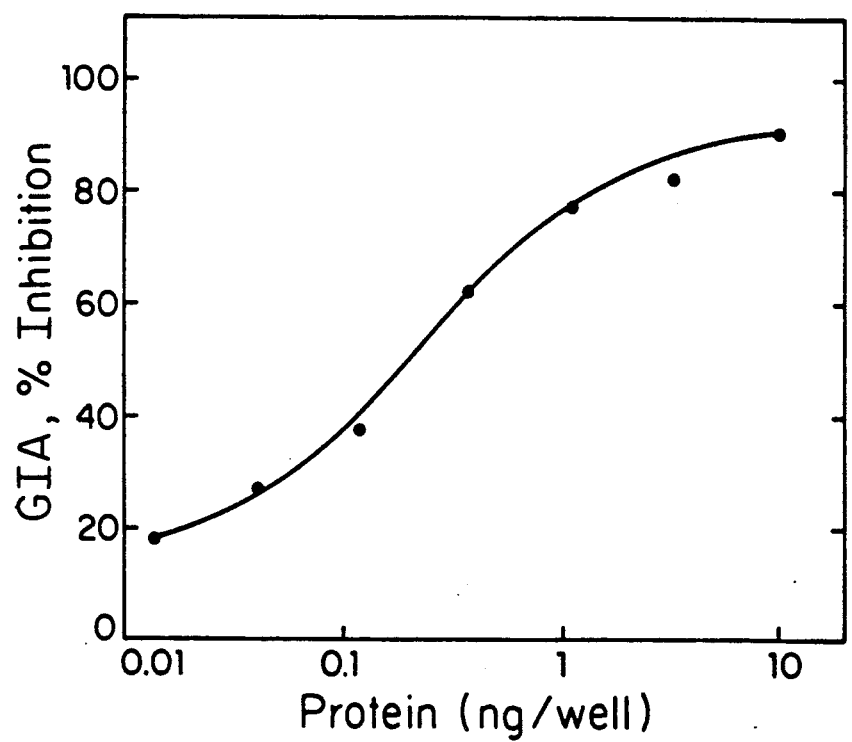

The inhibition of $^{125}$I-deoxyuridine incorporation into DNA of A431 cells by different concentration of the purified AR is given in FIG. 9A. A 50% inhibition of DNA synthesis was observed at approximately 0.2 ng/well. Thus, a 50% DNA synthesis inhibition in A431 human epidermal carcinoma cells was seen at approximately 0.13 nM concentration of pure protein. However, it should be noted that GIA of AR depends on experimental conditions such as number of cells/well (cell density), time of factor application, duration of treatment, serum concentration, and other variables.

When A431 cells were grown in the absence and presence of various concentrations of AR, and cell growth monitored by a direct cell count, it was found that AR inhibited A431 proliferation in a dose-dependent manner (data not shown). Thus, the extent of $^{125}$I-deoxyuridine incorporation into DNA is a good measure of cell growth.

Figure 9B:
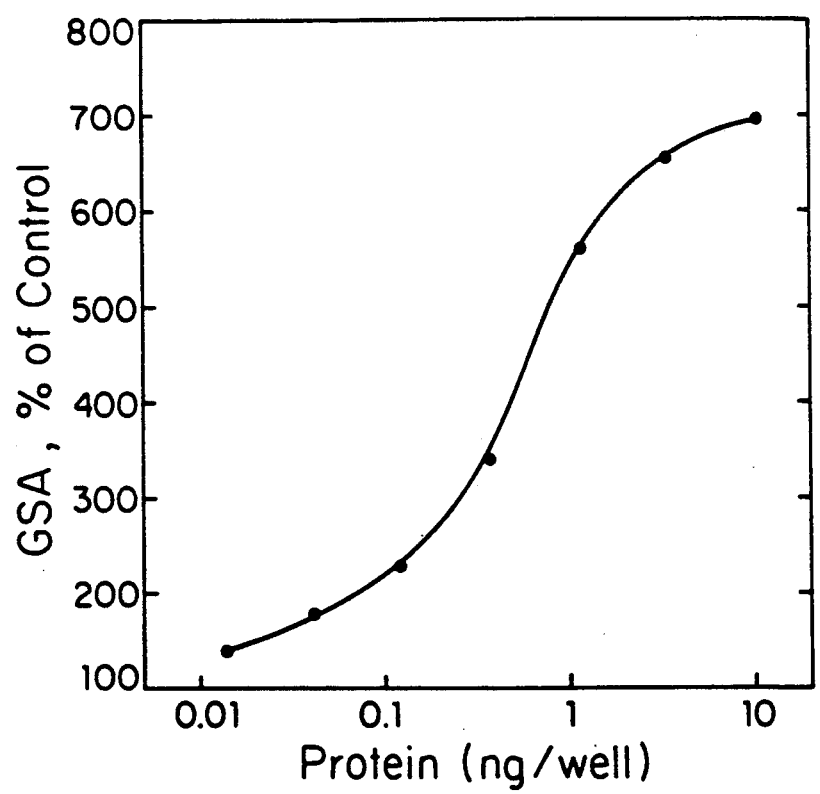

The stimulation of $^{125}$I-deoxyuridine incorporation into DNA of human foreskin fibroblasts (Sadamoto) by various concentrations of the purified AR is shown in FIG. 9B. A two-fold stimulation of $^{125}$I-deoxyuridine incorporation was seen at approximately 0.7 ng/ml or approximately 0.05 nM AR. The maximum response was approximately a six-fold stimulation of $^{125}$I-deoxyuridine incorporation into these fibroblasts. Thus, AR acts as a growth factor for human fibroblasts even in the presence of 5% FBS.

The effect of AR on the incorporation of $^{125}$I-deoxyuridine into DNA of various tumor and non-tumor human cell lines, and some non-human cell lines was investigated. The data are presented in Table IV. AR inhibited the growth of various clones of A431 cells, human breast carcinoma cells HTB 132, human ovary teratocarcinoma cells HTB 1575, human epidermal carcinoma of cervix cells CRL 155, human papillary adenoma of ovary cells HTB 75, and human adenocarcinoma of breast cells HTB 26. It did not exhibit any significant effect on a variety of cells (Table 3). AR stimulated the incorporation of $^{125}$I-deoxyuridine to several human fibroblasts cell lines, human pituitary tumor cells CRL 7386, human ovarian adenocarcinoma cells HTB77, African Green Monkey kidney cells BSC 1, and rat kidney cells SA6. AR did not significantly affect the proliferation of T, B, or endothelial cells. AR did not suppress human proliferative or cytotoxic T cell responses in mixed leukocyte culture reactions (MLC).

AR is a monomeric protein which requires intrachain disulfide bonds for activity, does not require glycosylation for activity, is stable under moderate acid and base treatments, and is stable when heat treated at 56° C. for 30 minutes. AR loses complete biological activity when reduced, when heated at 100° C. for 5 minutes, when digested with trypsin, endopeptidase Lys-c, endopeptidase ARG, or endopeptidase GLU.

TABLE IV

| | | Effects of Amphiregulin on the Proliferation of Cells[a] | |
|---|---|---|---|
| | Indicator Cells | Growth Inhibitory Activity (units)[b] | Growth Stimulatory Activity (units)[c] |
| Human | Epideroid carcinoma of vulva A431 | 125 | |
| Human | Adenocarcinoma of breast HTB 132 | 240 | |
| Human | Epidermoid carcinoma of cervix CRL 1550 | 28 | |
| Human | Papillary adenoma of ovary HTB 75 | 19 | |
| Human | Teratocarcinoma of ovary HTB 1572 | 55 | |
| Human | Adenocarcinoma of breast HTB 26 | 5 | |
| Human | Melanoma A375 | N.D. | N.D. |
| Human | Adenocarcinoma of breast ZR 75 30 | N.D. | N.D. |
| Human | Adenocarcinoma of breast MCF-7 | N.D. | N.D. |
| Human | Adenocarcinoma of lung A549 | N.D. | N.D. |
| Human | Adenocarcinoma of prostate PC3 | N.D. | N.D. |
| Human | Carcinoma of colon H3347 | N.D. | N.D. |
| Human | Lymphoblastoid (T cells) CEM | N.D. | N.D. |
| Human | EBV transformed B cells | N.D. | N.D. |
| Human | Epidermal carcinoma of larynx Hep 2 | N.D. | N.D. |
| Human | Cervical carcinoma CRL 1594 | N.D. | N.D. |
| Human | Adenocarcinoma of ovary HTB 77 | | 25 |
| Human | Foreskin fibroblasts (Sadamoto) | | 225 |
| Human | Foreskin fibroblasts (Goodwin) | | 70 |
| Bovine | Fetal heart endothelial cell | N.D. | N.D. |
| Murine | Balb/3T3 | N.D. | N.D. |
| Simian | African green monkey kidney BSC-1 | | 65 |
| Rat | Kidney SA6 | | 45 |

[a]125 units (GIA on A431 cells) of AR were suspended in 250 μl test media, serially diluted 5-fold with test media. Six dilutions were used for each cell. The fractions were assayed for growth modulatory activity and the GIA and GSA units were calculated.
[b]One GIA unit was defined as the amount of factor needed to inhibit $^{125}$I-deoxyuridine incorporation into cells by 50%.
[c]One GSA unit was defined as the amount of factor required to increase $^{125}$I-deoxyuridine incorporation into cells by 100%.
N.D. = Not Detectable.

The effect of AR and EGF on NRK-SA6 cell colony formation in soft agar in the absence and presence of TGF-β was carried out and results are shown in Table V. EGF induced anchorage independent growth of SA6 cells in a dose dependent manner in the presence of TGF-β, whereas, AR was found to be a very weak inducer of SA-G colony formation in soft agar (Table V).

TABLE V

| Effect of AR and EGF on NRK-SA6 Cell Colony Formation in Soft Agar | |
|---|---|
| Addition (per mL) | Number of Colonies per 6 Fields |
| None | 0 |
| TGF-β (1 ng) | 0 |
| AR (2 ng) | 0 |
| AR (4 ng) | 0 |
| AR (2 ng) + TGF-β (1 ng) | 7 |
| AR (4 ng) + TGF-β (1 ng) | 8 |
| EGF (2 ng) | 0 |
| EGF (4 ng) | 6 |
| EGF (2 ng) + TGF-β (1 ng) | 30 |

TABLE V-continued
Effect of AR and EGF on NRK-SA6
Cell Colony Formation in Soft Agar

| Addition | Number of Colonies |
| --- | --- |
| (per mL) | per 6 Fields |
| EGF (4 ng) + TGF-β (1 ng) | 114 |

Assays were performed as described in Section.
Colonies were defined as a cluster of at least six cells.

6.7.8. Effect of Ar on the Binding of Egf to its Specific Receptors

AR was found to inhibit the binding of $^{125}$I-EGF to A431 cells as well as to A431 plasma membranes (FIG. 10). A 50% inhibition of $^{125}$I-EGF binding to fixed cells and membranes was seen at about 1.1 nM and 1.8 nM EGF respectively, while at 50% reduction in EGF binding to cells and membranes was seen at approximately 1.8 nM and 5.7 nM AR respectively. Unlabeled EGF complete inhibited the $^{125}$I-EGF-receptor interaction at higher concentrations in both systems. However, the maximum competition with AR was 75% and 50% for binding to cells and membranes respectively. The competition curves for AR were also not parallel to that seen with EGF. These results suggest that AR exhibits lower affinity for EGF receptors than EGF. Also, AR might have its specific receptor closely related to EGF receptor.

Several clones of the A431 cell line with varying sensitivity to AR inhibition were selected and a lack of correlation between AR sensitivity and number of EGF receptor per cell or $K_D$ was observed (Table VI).

TABLE VI
Lack of Correlation Between Amphiregulin Sensitivity
of Various A431 Clones and Number of $K_D$ of EGF-Receptor

| A431 Clone | EGF Binding Parameters | | Relative Sensitivity (GIA) to AR |
| --- | --- | --- | --- |
| | Binding Sites per Cell | $K_D$ (NM) | |
| A-3 | 4.6 × 10$^5$ | 1.80 | 34 |
| F-8 | 9.0 × 10$^5$ | 3.13 | 20 |
| A-2 | 5.1 × 10$^5$ | 1.38 | 11 |
| A-8 | 5.3 × 10$^5$ | 3.18 | 1 |

Various clones of A431 were selected by growth in soft agar.
EGF binding was performed as described in Section 6.6.1.5., supra.
$K_D$ and numbers of binding sites were calculated from Scatchard plots (Scatchard et al., 1949, Ann. N.Y. Acad. Sci. 51:660-672.

6.7.9. Chemical Structure of Amphiregulin

The amino acid sequence of AR was deduced from microsequence analysis of S-pyridylethylated protein (SPE-AR) and fragments generated by the endoproteinase Lys C, Staphylococcal aureus V8 and endopeptidase Arg. The sequences of truncated protein and protein containing six additional amino acids are as follows:

Truncated AR

```
1                  10                    20
V V K P P Q N K T E  S E N T S D K P K R  K K K G G K N G K 30                 40                    50
N R R N R K K K N P C  N A E F Q N F C I H  G E C K Y I 60                 70          78
E H L E  A V T C K C Q Q E Y  F G E R C G E K
```

Larger AR

```
1                  10                    20
S V R V E Q V V K P  P Q N K T E S E N T  S D K P K R K K K 30                 40                    50
G G K N G K N R R N R  K K K N P C N A E F  Q N F C I 60                 70                    80        84
H G E C K Y I E H L E A V T C  K C Q Q E Y F G E R  C G E K
```

The above sequence uses the standard one-letter amino acid abbreviation for each amino acid. Amino acid residues about which there is doubt as to their identity are indicated in parentheses. The letter "X" denotes amino acid of unknown identity. The amount of larger AR was found to be about 16% to that of truncated AR.

The protein sequence of AR was compared with all proteins in the National Biomedical Research Foundation database (PIR 13). Genetic sequence Data Bank (Bolt Beranek and Newman, Inc., Los Alamos National Laboratory; Release #50) and the European Molecular Biology Laboratory DNA sequence library (Release γ #12). These searches revealed that AR is a novel protein and a member of the EGF super family of growth factors. This family includes EGF (mouse, human, rat, bovine, etc.), TGF-α, viral growth factors (vaccinia, myxo, and Shope fibroma), human plasminogen activator, bovine factor IX, human factor X, LDL receptor, bovine protein C, human proteoglycan core protein, product of Drosophila Notch gene, product of *C. elegans* lin 12 gene, and the product of cell lineage specific gene of sea urchin *S. purpuratus*. Alignment of the AR structure with the structures of EGF super family proteins reveals that AR, like other members of the EGF super family, contains the hallmark six essential cysteine residues, maintains conservation of cysteine residue spacing, and contains some of the characteristic and highly conserved amino acids. It is apparent that AR falls between the members of the growth factor family that look like EGF, TGF, and those that look like MGF, SFGF, especially in terms of the use of asparagine. For example, at position 2 (first cysteine=1) all TGFs and EGFs have proline, VGF has glycine, and MGF, SFGF, and AR have asparagine. In the same loop, at position 7, EGFs, VGFs have glycine, TGFs have glutamine, and MGF, SFGF, and AR have asparagine. However, in the third loop, AR does not have the conserved beta turn at position 34 (either an asparagine in MGF, SFGF, and a glycine in all the other members) but has a glutamic acid (low beta turn potential). AR has a different structure for the highly conserved third loop which may affect receptor binding. AR does not have the asparagine residues possibly used in MGF and SFGF as glycosylation sites within the growth factor structure proper.

The N-terminal sequence of AR has some analogy with the N-terminal sequences of TGFs, VGF, and MGF in that it is rich in prolines, serines, and threonines and like TGFs and VGF has potential N-linked glycosylation sites (in fact has one such site) as well as the possibility for O-linked glycosylation in this region rich in serines, threonines, and prolines. This region is highly conserved between the N-terminus of the TGF precursors and the N-terminus of VGF and appears to be a highly glycosylated region.

AR is an extremely hydrophilic protein, especially in the region containing amino acids 8 to 45 (FIG. 2). The hydropathy profile of AR exhibits little similarity to those of the other members in the EGF family. The hydropathy profile of the C-terminal portion of AR, though structurally related to other members of the EGF-family, is unlike the profiles of other members of this family (FIG. 11 B and C).

6.7.10. Ar Specifically Binds Dna $^{125}$-I-AR was tested for its ability to bind cellulose, denatured DNA cellulose and native DNA cellulose using the assay described in Section 6.6, supra. The results presented in FIG. 14A indicate that AR specifically binds both denatured and native DNA cellulose but does not bind to cellulose. Binding native DNA was three to four times greater than binding to denatured DNA.

Figure 14B:
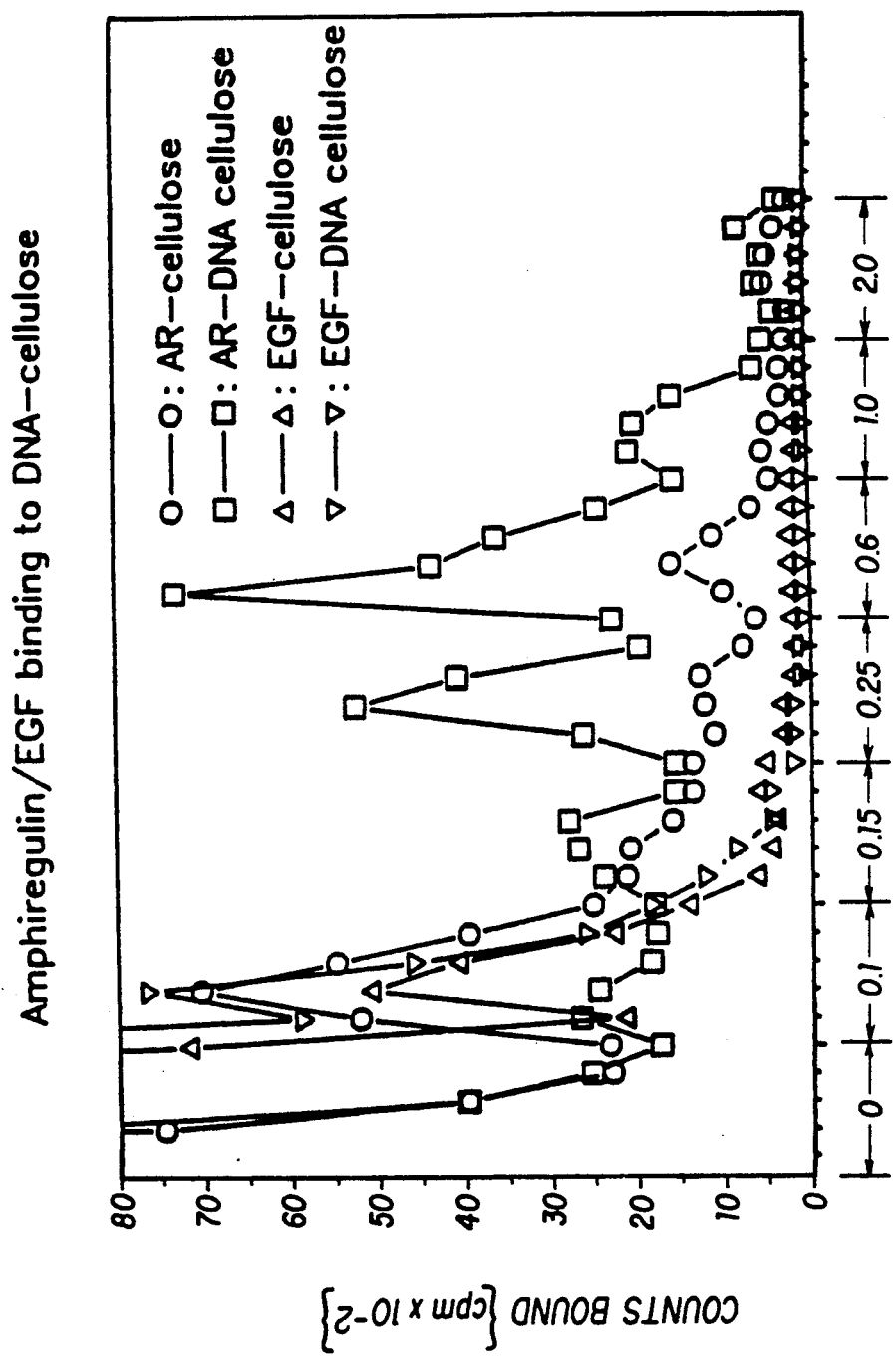

The ability of AR to specifically bind DNA differentiates AR from all other members of the EGF superfamily. For example, EGF is not able to bind DNA cellulose (FIG. 14B). The results strongly suggest that the hydrophillic 45 amino acid N-terminal domain of AR, not present in EGF or in other members of the EGF family, may be a nuclear localization sequence involved in targeting AR to the nucleus, where the factor interacts with DNA.

7. EXAMPLE: ANTIBODIES TO AMPHIREGULIN

The production of antibodies to AR and synthetic AR and AR-precursor peptides is described in the subsections below.

7.1. Materials and Methods

7.1.1. Solid Phase Peptide Synthesis

Amphiregulin was produced and purified as described in Section 6, supra. Five peptides corresponding to residues 31-50 (No. 279), 71-90 (No. 280), 108-130 (No. 264), 166-184 (No. 259), and 221-240 (No. 281) of the AR primary structure (FIG. 15) were synthesized by solid phase techniques on an Applied Biosystems Inc. automatic peptide synthesizer essentially as described (Merrifield, 1963, J. Amer. Chem. Soc. 85:2149). Synthesized peptides were cleaved from resin supports using a high HF cleavage procedure (Tam et al., 1988, J. Amer. Chem. Soc. 105:6442). Synthetic peptides were purified by reverse-phase HPLC.

7.1.2. Antibody Production

Polyclonal antisera to mature AR and synthetic AR-peptides, chemically conjugated to keyhole limpet hemocyanin (KLH) were prepared in young adult New Zealand white rabbits. The synthetic peptides were conjugated to KLH as described (Ishikawa et al., 1983, Immunoassay 4:235); mature AR was not coupled.

AR or peptide conjugates were emulsified with Ribi adjuvant system (Ribi Immunochem. Research, Inc., Hamilton, Mont.) A 1 ml total dose was administered to each rabbit: 0.8 ml intramuscularly at two sites in each hind leg and 0.2 ml subcutaneously at one site. To generate antisera against mature AR, 30 μg of mature AR was used for the primary inoculation and 15 μg used for the subsequent booster injections. To generate antisera against the synthetic AR-peptides, 100 μg of conjugated peptide was used for the primary inoculation and 50 μg for the subsequent boosters. Booster inoculations were administered every 3 to 4 weeks and rabbits were bled 10 to 14 days after the booster injections.

7.1.3. Immunoprecipitation

AR was radiolabeled with $^{125}$I using the chloramine T method (Barridge, 1978, Methods Enzymol. 50:54-65). 10 μl polyclonal sera (or dilution in PBS) was combined with 10 μl $^{125}$I-AR (50 ng/ml, specific activity 425 μCi/μg) and 30 μl PBS and assayed essentially as described (LeBier et al., 1982, J. Immunol. 129:2287-2292).

7.1.4. Radioimmunoassay

Polyclonal sera were diluted 1:50 in PBS. $^{125}$I-AR (1 μg/ml, specific activity 425 μCi/μg) was diluted 1:200 with TNEN/0.1% BSA (20 mM Tris pH 7.4, 5 mM EDTA, 150 mM NaCl, 0.05% NP-40, 0.1% BSA). 10 μl unlabeled AR (1 mg/ml), 10 μl diluted polyclonal sera and 30 μl diluted $^{125}$I-AR were combined and incubated at room temperature for 45 minutes. Protein A-sepharose solution was prepared as follows: 200 mg dry Pharmacia protein A-sepharose was rehydrated with 1.4 ml PBS and 80 μl of the rehydrate was washed and diluted to 440 μl with a solution containing 100 mM Tris pH 8.1, 150 mM NaCl, 0.5% Triton X-100, 2 mM PMSF, 1% Aprotinin and 0.5 μg/ml Levpeptin. 20 μl protein-A solution was then added to the mixture and allowed to incubate for an additional 30 minutes. The sepharose beads were then washed twice with 500 μl TNEN/0.1% BSA, resuspended in 50 μl SB (80 mM Tris pH 6.8, 3% SDS, 15% glycol, 0.01% bromophenol blue, 5% β-mercaptoethanol) and heated at 100° C. for 5 minutes. Samples were centrifuged and supernatants assayed for radioactivity in a gamma counter. This procedure detected as little as 100 pg AR.

7.1.5. Enzyme-Linked Immunosorbent Assay

The solid-phase micro-ELISA procedure was modified from U.S. patent Ser. No. 740, 124, filed May 30, 1985. Terasaki microtrays were prepared by addition to each well of 5 μl of AR synthetic peptides, diluted in PBS to various concentrations, and then allowing the solution to dry overnight at room temperature. 5% Blotto in PBS was added to the plates and allowed to stand at room temperature for 1 hour. Next, 10 μl dilutions of polyclonal antibody solution (diluted in PBS/1% Blotto/0.05% Triton X-100) were added to each well, incubated for 1 hour at room temperature, and then washed four times with PBS. 5 μl of peroxidase-conjugated goat anti-rabbit IgG (Cappel) at a dilution of 1:1000 in PBS/1% Blotto/0.05% Triton X-100 was added to each well, incubated for 1 hour at room temperature, and then washed six times with PBS. 10 μl MicroEIA Chromogan Solution (Genetic systems Corp.) was added at a 1:20 dilution, and absorbance was then read at OD$_{492}$ after 20 minutes and 40 minutes according to the Genetic systems Micro-EIA protocol.

7.1.6. Western Blotting

Samples were electrophoresised on a 15% polyacrylamide gel or a 16% tricine polyacrylamide gel, and a BioRad mini-gel apparatus. The gel was then placed adjacent to a sheet of nitrocellulose and sandwiched in the cassette such that the nitrocellulose was positioned on the cathodic side. Protein transfer was performed using a current of 400 mA at constant power for 30 minutes. The nitrocellulose was then removed and soaked in 2.5% Blotto/PBS/0.2% NP-40 overnight at 4° C.

The nitrocellulose filter was then exposed to antiserum diluted in 2.5% Blotto/PBS/0.2% NP-40 reaction buffer for 90 minutes at room temperature on a rocking platform, followed by four washes (5 minutes each wash) in 2.5% Blotto/PBS/0.2% NP-40.

Alkaline phosphatase-conjugated Protein A (Cappel) diluted 1:500 in 2.5% Blotto/PBS/0.25% NP-40 was then added to the nitrocellulose sheet, and incubated for 60 minutes at room temperature on a rocking tray. The filter was then washed four times (3 minutes each wash) with PBS/0.2% NP-40, followed by 5 minutes in "APS" buffer (100 mM Tris pH 9.5, 100 mM NaCl, 5 mM MgCl$_2$). The filter was developed in color reagent (40 ml APS buffer, 12 mg 5-bromo-4-chloro-3 indoyl phosphate (Sigma), 6.8 mg nitroblue tetrazolium (Sigma), made up just prior to use and filtered through a 0.2 μm filter) quenched with H$_2$O, and then allowed to air dry.

7.2. Characterization of Ar Antibodies

Polyclonal sera raised against mature Ar and synthetic AR-peptides were characterized by radioimmunoprecipitation, radio immunoassay, ELISA, and Western blotting. The results are given in Table VII.

TABLE VII

CHARACTERIZATION OF ANTIBODIES TO AMPHIREGULIN AND SYNTHETIC AR-PEPTIDES

| Polyclonal Sera to | Assay Method | | | |
|---|---|---|---|---|
| | RIP | RIA | ELISA | WB |
| Mature AR | 1:256[a] | 1:250 (.100 pb)[b] | ND | 1:250 (1 ng) |
| Peptide 259 | 1:256 | ND | ND | ND |
| Peptide 264 | 1:256 | 1:250 (.100 pb) | 1:100 (5 ng) | 1:100 (0.1 ng) 1:500 (1 ng) |
| Peptide 279 | ND | ND | 1:100 (5 ng) | ND |
| Peptide 280 | ND | ND | 1:100 (5 ng) | ND |
| Peptide 281 | ND | ND | 1:100 (5 ng) | ND |

[a]Dilution of Antisera required.
[b]The values in parenthesis indicate the sensitivity of method.
RIP = radioimmunoprecipitation
RIA = radioimmunoassay
ELISA = enzyme linked immunosorbent assay
WB = Western blot
ND = not determined

8. EXAMPLE: cDNA CLONING OF THE AMPHIREGULIN PRECURSOR

The following example describes the cloning and analysis of cDNAs encoding the Amphiregulin precursor from TPA-treated MCF-7 human breast carcinoma cells.

8.1. Materials and Methods

8.1.1. Rna Preparation

RNA was isolated from subconfluent cells grown in T150 tissue culture flasks or from fresh frozen tissue samples using the Guanidinum method as described by Chirgwin (1979, Biochemistry, 18,5294). Cells from four T150s were washed in PBS, trypsinized, rewashed in PBS and the pellet resuspended in 8 ml 4 M guanidinium isothiocyanate solution. DNA was sheared by passing the solution through an 18 gauge needle. The sample was overlayed onto 2.4 ml 5.7 M CsCl in a Beckman SW41Ti tube and centrifuged at 32,000 rpm for 20 hr at 20° C. Pellets were resuspended in 300 μl 2.5 M CsCl, and precipitated with 2 volumes EtOH at room temperature. The pellets were resuspended in 300 μl H$_2$O, then 35 μl 3 M sodium acetate (pH 5.2) and 800 μl EtOH added and the RNA precipitated at −70° C. Precipitation was repeated and the RNA was then dried briefly, resuspended in 100 μl H$_2$O, quantitated at OD$_{260}$, and stored at −70° C.

8.1.2. Random Primed Labeling with $^{32}$P-TTP

AR coding region specific fragments were excised from low gel temperature agarose (BioRad) and labeled with $^{32}$P-TTP (NEN, 3000 Ci/mmol) using the random primed method developed by Feinberg (1983, Anal. Biochem., 137,266). Unincorporated deoxyribonucleosides were removed by chromatography on a 1.5 ml Sephadex 50 column. Specific activities were typically 0.5–2.5×10$^9$ cpm/μg.

8.1.3. Rna Gels and Northern Blot Analysis

Ten or twenty μg of total RNA was electrophoresed on 1.2% agarose/formaldehyde gels for Northern analysis. The agarose/formaldehyde gels were prepared in 40 mM N-morpholinopropanesulfonic acid (MOPS), pH 7.0/1 mM EDTA/10 mM sodium acetate/2/2 M deionized formaldehyde (pH5.6) in an IBI VCV gel apparatus with frosted plates. RNA was denatured in the same buffer with 50% formamide at 65° C., and run in 1×MOPS, at 20–30 mA for 3–5 hr. The gel was rinsed in 10×SSC for 30 min and transferred to Hybond-N membranes (Amersham), UV-crosslinked (1200 μJoules), prehybridized and hybridized in 5×SSPE (1×SSPE is 0.18 M NaCl/10 mM sodium phosphate, pH 7.7, 0.1 mM EDTA), 5×Denhardt's, 0.5% SDS, and 20 μg/ml denatured salmon sperm DNA as carrier. Hybridizations were carried out at 42° C. for 16 hr with 2×10$^6$ cpm/ml of the $^{32}$P-ARBP1. Blots were washed several times in 2×SSC with 0.1% SDS at room temperature followed by 1×SSC/0.1% SDS, 65° C., and exposed on Kodak X-OMAT with two Dupont Lightning Plus intensifying screens at −70° C. Bands were scored as (+) if clearly visible after overnight exposure, (+/−) if visible after 3 day exposure, and (++) if detectable after 6 hr.

8.1.4. cDNA Cloning

MCF-7 cells were harvested for RNA after treatment with 100 μg/ml of 12-0-tetradecanoyl-phorbol-13-acetate (TPA) for 24, 40, and 72 hours. Poly(A)+RNA was isolated from pooled aliquots of these samples and used as the template for double-stranded cDNA synthesis essentially as described (Gubler and Hoffman, 1983, Gene 25:263). G-tailed cDNA was ligated into the EcoRI site of λgt10 using BR1 oligonucleotide adapters (Rose et al., 1986, Proc. Natl. Acad. Sci. U.S.A. 83:1261-1265).

Specifically, 5 μg TPA treated MCF-7 poly(A)+ RNA was heat denatured and primed with 5 μg Oligo(dT) using 100 U of reverse transcriptase in a 45 μl reaction volume. Second strand synthesis was performed with 4 U RNase H and 115 U E. coli DNA pol I. Ten μg T4 DNA polymerase was used to remove 3' overhangs, creating blunt ends. The entire 6.8 μg of double-stranded cDNA was sized over a Sephadex G50 column to select for cDNAs over 500 bp, and then 150 ng cDNA was dG-tailed with terminal deoxynucleotidyl transferase. dG-tailed cDNA was ligated with the EcoRI site of λgt10 using BR1 adapters (AATTCCCCCCCCCCCC). Ligated DNA was packaged in vitro (Grosveld et al., 1981, Gene 13:227-237) and plated on E. coli C600 rK−mK hfl with an efficiency of 10⁶ recombinants/μg cDNA Duplicate nitrocellulose lifts were taken on 2.5 × 10⁵ recombinants and filters were screened with [$^{32}$P]-labeled best guess and degenerate oligonucleotide probes (Table VIII, below) derived from the AR primary sequence as determined by automated Edman degradation of N-Glycanase treated-reduced and S-pyridylethylated AR (Section 6, supra).

striction and sequence analysis. All of these clones had identical restriction maps based on BsmI, EcoRV, PvuII, SstI, and SmaI, except pAR9 which had a 3' truncation of 100 bp and was later found to originate from an A$_5$ track, presumably sufficient for priming with oligo(dT).

8.2. Nucleotide Sequence Analysis of Ar cDNA Clones

Exact oligonucleotide primers were used to sequence both strands of the 1,230 bp pAR1 clone using the dideoxy chain-termination method (Sanger et al., 1977, Proc. Natl. Acad. Sci. U.S.A. 74:5463-5467). The complete nucleotide and deduced amino acid sequence of clone pAR1 is shown in FIG. 16. An open reading frame of 965 bp begins at nucleotide number 1. The first AUG lies at position 210, but does not conform with the Kozak optimal consensus for translational start sites (Kozak, 1984, Nucleic Acids Research 12:857-872; Kozak, 1986, Cell 44:283-292) due to the absence of a purine at position −3. However, such AUG triplets can serve as the initiator codon, as Kozak observed in some 3% of the messages examined, and of possible importance is the presence of an adenosine at position −1 in all of these 'less favored' AUGs and in the mRNA of AR. Although a second methionine is located at nucleo-

TABLE VIII

| Probe | Sequence | Length (Degeneracy) |
|---|---|---|
| Degenerate | | |
| ARD41 | C     K     C     Q     Q     E    (Y)<br>3' ACA TTT ACA GTT GTT CTT AT  5'<br>     G     C     G     C     C     C | 20<br><br>(64-fold) |
| ARD58 | E     C     K     Y     I     E    (H)<br>3' CTT ACA TTT ATA TAA CTT GT  5'<br>     C     G     C     G          C | 20<br><br>(32-fold) |
| Best Guess | | |
| ARK31 | K   N   P   C   N   A   E   F   Q   N   F   C<br>3' TTC TTG GGT ACG TTA CGA CTC AAG GTC TTG AAG ACG<br><br>I   H   G   E   C   (K)<br>TAG GTA CCG CTC ACG TT  5' | 53 |
| ARK41 | (Y)  I   E   H   L   E   A   V   T   C   K   C<br>3' AG TAA CTC GTA GAC CTC CGA CAC TGG ACG TTC ACG<br><br>Q   Q   E   Y   F   G   E   R   C   G   (E)<br>GTC GTC CTC ATG AAA CCG CTC GCC ACA CCG CT  5' | 67 |
| ARNT | V   V   K   P   P   Q   D   K   T   E   S   E<br>3' CAC CAC TTC GGG GGG GTC CTG TTC TGT CTC AGG GTC<br><br>N   T   S   D   K   P   K   (R)<br>TTG TGG AGA CTC TTC GGG TTG TG | 59 |

Restriction analysis revealed a paucity of sites in the cDNA insert of pAR1, with single sites for BsmI, EcoRV, HgaI, NaeI, PvuII, SmaI, and SstI, and two sites for SspI. No digestion within the insert occurred with BamHI, ClaI, EcoRI, HindIII, KpnI, PstI, PvuI, SphI, StuI, and XbaI. A 170 bp BsmI to PvuII fragment was isolated and used to probe a second cDNA library of 100,000 recombinants which was made essentially as described above. Thirteen positive clones were identified having inserts ranging from 300 bp to 1.3 kb, six being greater than 1 kb and five which contained a single SstI site known to be within 100 bp from the 5' end of pAR1. Four of the later five inserts were subcloned (pAR3, pAR5, pAR9, pAR13) for further retide 378 which does conform with the initiator consensus sequence, the first AUG is believed to be the true translational start site since it is followed by a predicted 19 amino acid stretch of predominantly hydrophobic residues interrupted by 3 prolines, typical of a signal peptide sequence (Heijne, 1983, J. Biochem. 133:17-21).

The longest open reading frame starting with a methionine encodes a 252 amino acid polypeptide that includes the 19-residue signal peptide. The coding sequence is preceded by 209 nucleotides of 5'-untranslated sequence and is followed by a translational termination signal, TAA, and 262 nucleotides of 3'-untranslated sequence. A potential poly(A) addition signal sequence, AATAA, is located 64 nucleotides upstream from a stretch of 15 adenylate residues, presumed to be the poly(A) tail. The AR 3' untranslated region contains four copies of the sequence ATTTTA, which is also present in certain lymphokines, cytokines, and proto oncogenes. In GM-CSF, this sequence mediates RNA destabilization and degradation (Shaw, 1986, Cell 46:659-667). Conservation of this motif in functionally similar molecules suggests that AR may also be related to this class of lymphokines.

The cDNA sequence confirms the mature AR peptide sequence (Section 6, supra) except at amino acid position 113 (FIG. 15) which was sequenced as aspartic acid (D) by protein analysis and was deduced as asparagine (AAT=N) from the cDNA clones. Of five cDNAs examined, all had their 5' ends within the first 25 bp of the pAR1 sequence.

Figure 11D:
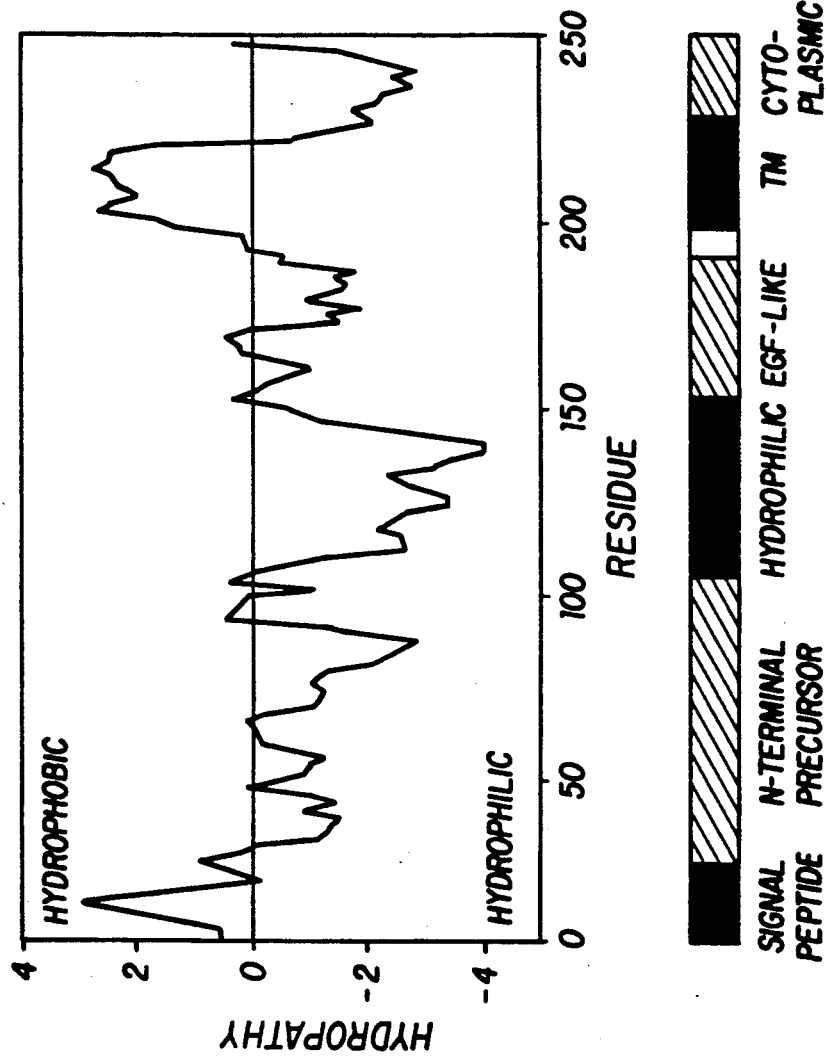
Figure 11E:
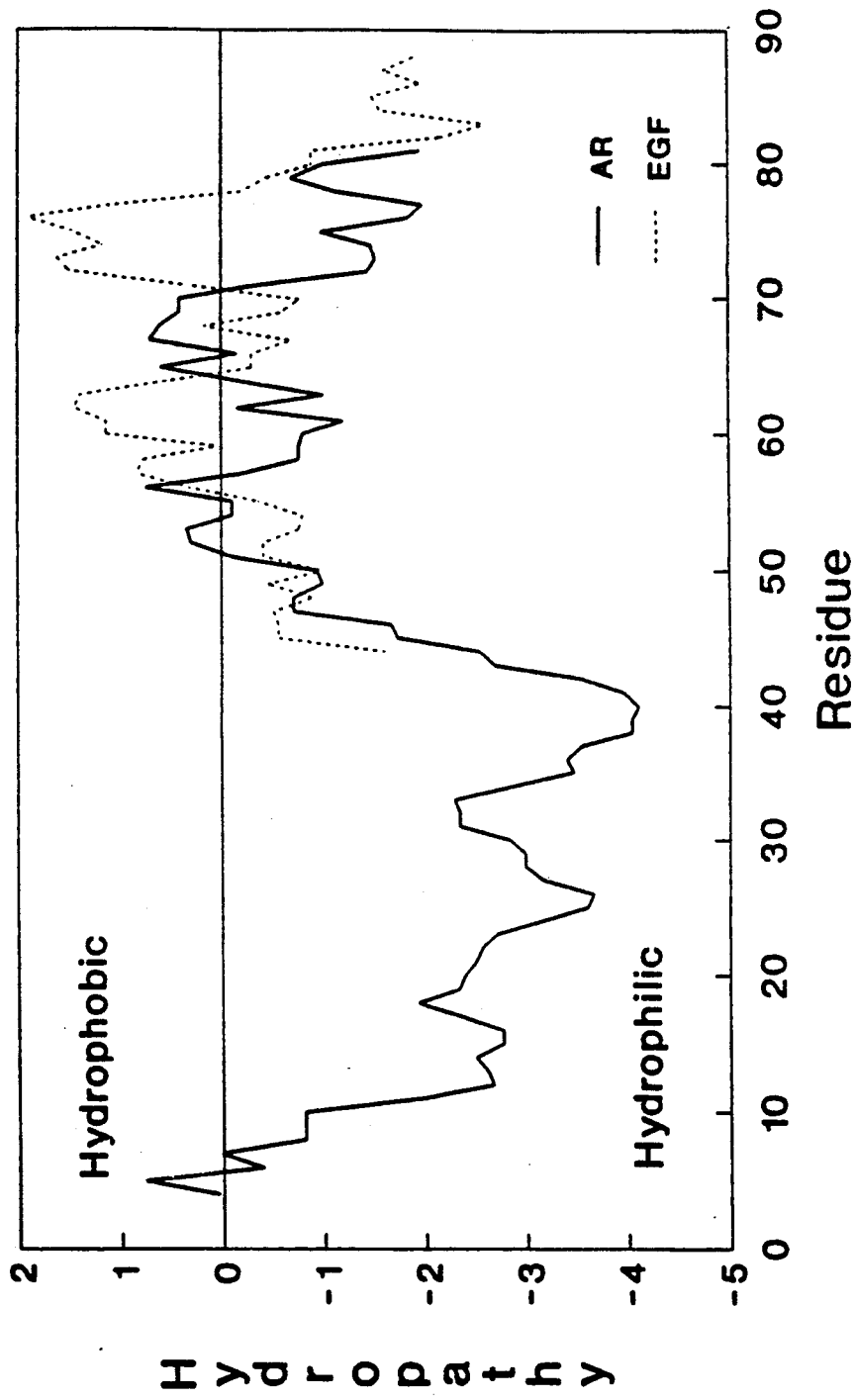

Comparison of the cDNA sequence with the best guess probes showed 74% (ARK41) and 77% (ARK31) overall homology. Neither probe had more than an eight consecutive bp match, but, overall, 50 of 67 nucleotides aligned for ARK41 produced a detectable signal under conditions of very low stringency. The codon usage by AR mRNA sequence differs considerably from the usage frequencies reported by Lathe (Lathe, 1985, J. Mol. Biol. 183:1-12), explaining why the degenerate oligonucleotides provided stronger signals in this instance. From the cDNA and protein sequences, two proteins, of 9772 and 9173 molecular weight, are predicted for the two forms of mature AR based on the cDNA (FIG. 16) and protein (Section 6.7.9, supra) sequence. The hydropathy profile of the AR precursor is depicted in FIG. 11D.

The AR precursor has 3 potential N-glycosylation sites, one in the N-terminal domain (position 30 in FIG. 16) and 2 in the hydrophilic region of mature AR (positions 113 and 119). Glycosylation is known to contribute 10-12 kd to the molecular weight of mature AR, and it is likely to occur from carbohydrate addition at one or both of these sites in the hydrophilic domain.

The N-terminal serine-rich domain of the AR precursor (FIG. 15) contains three potential tyrosine sulfation sites at $Y^{81}$, $Y^{83}$, $Y^{87}$, based on the presence of acidic residues, turn-inducing amino acids, and the absence of residues which could contribute to steric hinderance (Huttner, 1987, TIBS 12:301-303). Most tyrosine-sulfated proteins are secetory proteins. Tyrosine-sulfation modifications are believed to be involved in activation, transport, or proteolytic processing of precursor proteins. The serine-rich domain of AR may also contain O-linked carbohydrate chains given the abundance of serine/threonine residues (23 of 81) in this region of the molecule, which are sites for such linkages. In this regard, O-glycosylated forms of another member of the EGF family, TGF-α, have been identified (Ignotz et al, 1986, PNAS, 83, 6307-6311).

None of the serine residues in the AR precursor fit the consensus sequence for cAMP-dependent kinase phosphorylation sites (Grima, et al., 1985, Proc. Natl. Acad. Sci. U.S.A. 82:617-621), nor do any of the tyrosine residues exhibit flanking sequence similarity to known phosphotryosine residues.

The hydrophilic domain of the mature AR protein is composed of numerous positively charged amino acids (16 of 37 residues are lysine or arginine), including two consecutive stretches of 4-5 basic, charged residues. The nuclear targeting signal of SV40 large T antigen is similar to this region of AR and contains a characteristic KKKRK sequence preceded by small amino acids (glycine, alanine, proline) which may permit the formation of an α-helical structure (Burglin et al., 1987, EMBO 6:2617-2625; Dingwall, et al, 1987, EMBO 6:69-74). Mutation analysis defined four consecutive basic residues as the predominant feature of the SV40 nuclear localization sequence (Lanford, 1984, Cell, 37, 801-813). Other nuclear proteins with similar stretches of basic amino acids believed to be involved in nuclear targeting include nucleoplasmin, polyoma virus large T, histones, and c-myc. Fusion of various nuclear signal sequences to the genes for chicken pyruvate kinase, albumin, immunoglobulin, ferritin, and β-galactosidase, results in the localization of these otherwise cytoplasmic proteins to the nucleus (Moreland, 1987, Mol. Cell. Biol. 7:4048-4057). Whether the hydrophilic sequences in AR are involved in targeting this growth modulator to the nucleus has not been verified; however, the ability of AR to specifically bind DNA implies that AR has a functional role within the nucleus. In this regard, AR may regulate DNA synthesis, the cell cycle, or a variety of other nuclear events.

The TGF-α precursor contains multiple cysteines in the C-terminal cytoplasmic domain, some of which undergo covalent palmitate attachment (Bringman, 1987, Cell, 48, 429-440) In contrast, the AR precursor lacks any cysteines in its cytoplasmic domain and therefore is not expected to contain palmitate residues. Although the biological function of palmitate attachment is unknown, this represents yet another difference between AR and other members of the EGF superfamily.

8.3. Cellular Sources of Amphiregulin Synthesis

Northern blot analysis (Thomas, 1980, PNAS, 77, 5201) using $\alpha^{32}$P-labeled AR cDNA fragments showed hybridization to a single 1.4 Kb RNA species from a variety of normal human tissues and tumor cell lines. A single band was seen on Northern blots, using either AREB1 (a 480 bp BstEII - Pvu II fragment of pAR1-containing the entire coding region of mature AR and part of the N-terminal precursor and transmembrane domains) or AR170 (a 170 bp BsmI - PvuII fragment of pAR1 containing only the C-terminal half of mature AR) as labelled probes. The results presented in Table IX, below, show that low-level expression (+) of AR RNA was observed in normal adult lung and pancreas tissue. Lower, yet detectable expression (+/−) was observed in normal kidney, liver and brain tissue.

TABLE IX

| Normal Human Tissue | AR RNA |
|---|---|
| Lung | + |
| Liver | +/− |
| Pancreas | + |
| Kidney | +/− |
| Spleen | − |
| Brain | +/− |
| Placenta | − |
| Intestine, fetal | − |

Since AR was originally isolated from TPA treated MCF7 cells, it was of interest to determine the time course for TPA induction of AR RNA in these cells. MCF-7 cells were treated with TPA for 0, 1, 3, 6, 18, 24, and 48 hours, total RNA was isolated and 10 μg run on each lane of a 1.2% formaldehyde agarose gel, transferred to nylon membranes and screened with ARBP1 probe complementary to the entire coding region of mature AR. An impressive increase in the 1.4 kb AR RNA species was seen as early as 1 hour after treatment with TPA, with maximal levels reached at between 18 and 24 hours. Subsequent Northern blots, probed with $^{32}$P-ARBP1 showed TPA-stimulation of AR RNA synthesis in other breast cancer cell lines although maximal levels were never as high as in the TPA induced MCF-7 cells.

A panel of tumor cell lines was tested for AR RNA levels both before and after 24 hour induction with TPA. The results are summarized in Table X, below. With but a few exceptions, the only sources of detectable AR RNA were in human breast cancer lines treated with TPA. One such exception is Caki-1, a human clear cell kidney carcinoma line which constitutively expresses high levels of AR RNA comparable to the amounts seen in the TPA induced MCF-7 cells. All of the TPA treated breast cancer cell lines surveyed showed AR-specific hybridization.

AR apparently serves some functional role in the adult lung, pancreas, kidney, liver and brain, possibly being involved in a wide variety of processes including wound healing, tissue regeneration, and maintenance of neuronal cells.

extensively in 1×SSC, 65° C., and autoradiographed overnight at −70° C.

9.1.2. Genomic Library Construction

Bacteriophage lambda L47.1 was selected as the cloning vector and phosphatase-treated arms were prepared after digestion with BamHI, EcoRI, and HindIII. High molecular weight DNA from MCF-7 cells was digested with HindIII, electrophoresed on 0.8% low gel temperature agarose (BioRad), and size fractionated. The agarose fraction maximally enriched for the desired restriction fragment was melted at 65° C., the DNA was extracted with phenol and NaOAc, then ethanol precipitated and resuspended at 25-100 μg/ml. Library constructions consisted of an overnight ligation at 14° C. of 100 ng lambda L47.1 arms and 40 ng extracted size fractionated DNA in a 5 μl reaction volume, using T4 DNA ligase (Biolabs). Recombinant phage were packaged in vitro with extracts (Grosveld, 1981, Gene, 13, 227-237) prepared with E. coli strains BHB2688 N205 recA− (lambda imm$^{434}$ cIts b2 red3 Eam4 Sam7), and BHB2690 N205 recA− (lambda imm$^{434}$ cIts b2 red3 Dam15 Sam7). Libraries were titered on E. coli LE392.

TABLE X

| Human Cell Line | Origin | AR RNA Level[1] UNINDUCED | TPA INDUCED |
|---|---|---|---|
| MCF-7 (HTB 22) | Breast Adenocarcinoma | + | + + + + |
| HBL-100 (HTB 124) | Breast, Normal | − | + |
| BT-474 (HTB 20) | Breast Ductal Carcinoma | − | + |
| MDA-MB-157 (HTB 24) | Breast Medulla Carcinoma | + | + + |
| MDA-MB-361 (HTB 27) | Breast Adenocarcinoma Brain Metastasis | + | + + |
| SK-BR-3 (HTB 30) | Breast Adenocarcinoma | − | + |
| BT-476 | Breast Carcinoma | − | + |
| JEG-3 (HTB 36) | Choriocarcinoma | − | +/− |
| Caki-1 (HTB 46) | Kidney Clear Cell Carcinoma Skin Metastasis | + + + | + + + |
| SK-HEP-1 (HTB 52) | Liver Adenocarcinoma | − | − |
| G-401 (CRL 1441) | Wilm's Tumor | − | − |
| HEPM (CRL 1486) | Embryonic Palatal Mesenchyme | − | +/− |
| A-431 (CRL 1555) | Epidermoid Carcinoma | − | − |
| HBL-299 (CCL 137) | Embryonic Lung | − | − |
| HUF | Foreskin Fibroblast | − | +/− |

9. EXAMPLE: GENOMIC CLONING AND ANALYSIS OF THE AMPHIREGULIN GENE

The following example describes the genomic cloning of the human amphiregulin gene, its structure and intron/exon organization. Functional and evolutionary implications with regard to the EGF superfamily of growth factors is also discussed.

9.1. Materials and Methods 9.1.1. Southern Blot Hybridizations

Total genomic DNA was isolated (Maniatis, 1982, In Molecular Cloning: A Laboratory Manual) from subconfluent cells in T150 tissue culture flasks. 20 μg DNA was digested with restriction enzymes as specified, electrophoresed on 0.8% agarose gel, blotted onto Hybond-N (Amersham) with 20×SSC bottom buffer (Southern, 1975, J. Mol Bio., 98, 503-517), and DNA bound by exposure to 1200 μJoules short wave UV. Filters were hybridized at 65° C. overnight in hybridization buffer (6× SSC, 5× Denhardt's solution, 0.5% SDS and 20 μg/ml sheared denatured salmon sperm DNA) containing 2×10$^6$ cpm of $^{32}$P-labeled AR specific fragment per ml. Probes were random prime labeled to a specific activity of 5-25×10$^8$ cpm/μg. Filters were washed Genomic clones were screened with the AR specific DNA probes by in situ plaque hybridization (Benton, 1977, Science 196, 180-182), and DNA was isolated from plaque purified positives clones (Huynh, 1985, In DNA cloning techniques: a practical approach, D. Glover, ed. (Oxford: IRL Press), pp. 49-78). HindIII inserts were excised and subcloned into pEMBL 18 for restriction analysis and propagation.

9.1.3. Primer Extension Assay

RNA was isolated from MCF-7 cells as described in Section 8, supra. Synthetic oligonucleotides complimentary to nucleotides 40 to 60 (ARAP) and 76 to 97 (ARCP) in the AR cDNA sequence were $^{32}$P-end labeled with T4 polynucleotide kinase to a specific activity of 2-5×10$^8$ cpm/μg. One million cpm of labeled oligonucleotide was used to prime first strand cDNA synthesis on 50 μg MCF-7 RNA essentially as in Section 8.1.4 supra. The products were treated with RNase A, extracted with phenol and chloroform, ethanol precipitated, heat denatured in 80% formamide, 100° C., 5 minutes, and analyzed by electrophoresis on standard 8% polyacrylamide-7M urea sequencing gels.

9.1.4. Cat Assay

MCF-7 cells were grown as described in Section 6.2.1 supra. For each assay, $1-2 \times 10^6$ cells were plated in a 100 mm dish in 10 ml media, and 24 hours later, 20 μg calcium phosphate precipitated supercoiled plasmid DNA was added to the cells (Southern and Berg, 1982). The cells were rinsed with fresh media 4 hours after transfection and subjected to a 25% glycerol shock for 90 seconds. Cells were again rinsed and overlayed with 20 ml fresh media containing 0 or 100ng/ml TPA. Cells were washed and harvested 40 hours after glycerol shock and lysed by sonication in 100 μl 1 0.25 M Tris-HCl (pH 7.8). CAT activity was assayed essentially as detailed by Gorman et al. (1982). Cell extract (3-50 μl) was added to 2.5 mCi $^{14}$C-chloramphenicol (NEN), in a 150 μl reaction volume of 0.5 M Tris (pH 7.8), 0.5 mM AcetylCoA. The reactions were incubated at 37° C. for 2 hours, extracted with 1 ml ethyl acetate and developed on silica gel TLC plates with $CHCl_3$:1-butanol (95:5). TLC plates were dried and autoradiographed. The acetylated and unacetylated $^{14}$C-chloramphenicol was quantitated by counting excised spots in Optifluor. Units of CAT enzymatic activity were calculated as μg chloramphenicol acetylated per hour per μg protein in the cell extract.

9.1.5. In Situ Chromosomal Hybridization

Plasmid pAR9 was random prime labeled with $^3$H-TTP and used for hybridization to normal human metaphase cells prepared from phytohemagglutinin-stimulated peripheral blood lymphocytes at the 500-800 band stage. This probe corresponds to an AR cDNA lacking much of the 3' untranslated region and inserted into the EcoRI site of pEMBL18.

Hybridization was as described previously (Le Beau, 1985, PNAS, 82, 6692-6696) with 2, 4, 20, and 40 ng probe per ml of hybridization mixture. Autoradiographs were prepared using Kodak NTB-2 nuclear track emulsion and slides exposed for 7-60 days. Chromosome banding was visualized by staining with quinicrine mustard.

9.2. Chromosomal Location of the Ar Gene

The chromosome assignment of the human AR gene was determined by in situ hybridization of $^3$H-labelled AR cDNA to normal metaphase chromosomes. Silver grains were scored on 50 metaphase spreads with 30% being non-randomly distributed at bands 4q13-4q21. The result was confirmed by polymerase chain reaction (PCR) on hamster/human somatic cell hybrid DNA containing only human chromosome 4. Oligonucleotide primers derived from AR exon 3 and the flanking intron generated a 220 bp PCR fragment only in human DNA, and the hybrid DNA containing chromosome 4, whereas the hamster DNA was negative.

Chromosome region 4q13-4q21 also contains the genes for gro or Melanoma growth stimulatory activity (Anisowicz, A., et al., 1987, Proc. Natl. Acad. Sci. U.S.A., 84, 7188-7192; Richmond, A., et al., 1988, EMBO J. 7,2025-2033), c-kit receptor (Yarden et al., 1987, EMBO J. 6,3341-3351), platelet factor 4 (PF4)(Griffin et al., 1987, Cytogenetic Cell Genet., 45,43-73), the interferon-gamma inducible factor IP-10 (Luster, A.D., et al., 1987, Proc. Natl. Acad. Sci. U.S.A., 84, 1868-1871), vitamin D binding protein (Group specific component) (Cooke, N.E. et al., 1986, Human Genetics 73,225-229; McCombs J. L. et al., 1986,) Cytogenet Cell Genet, 42, 62-64), and statherin, a calcium regulating salivary protein (Sabatini L. M. et al., 1987, Am. J. Hum. Genet., 41,1048-1060). The gene for EGF is located distally at 4q25.

Gro, IP-10, and PF4 belong to a class of structurally related peptides which may constitute a family of growth factors clustered on chromosome 4. c-Kit encodes a cell surface receptor that is structurally and functionally related to several growth factor receptors which contain tyrosine-specific kinase activity, including EGF receptor, Neu oncogere, PDGF receptor, and insulin receptor. Generally the genes for ligands and their receptors map to distinct chromosomes but some have mapped to common chromosomal locations (Groffin, 1983, Nucl. Acids Res. 11:6331-6339; Pettenati, 1987, Proc. Natl. Acad. Sci. U.S.A. 84:2970-2974) The ligand for c-kit has not been identified, and AR must be tested for such an activity.

Specific translocations are seen in many malignancies. The most frequently recorded cytogenic aberration in congenital acute lymphoblastic leukemia (ALL), t(4;11)(q21;q23), involves the region to which AR has been mapped (Heim, S. et al., 1987, Leukemia, 1, 16-23). ALLs are now classified by morphology as defined by the French-American-British Cooperative Group (FAB), B and T cell markers, and chromosomal analysis. These classifications serve as the basis for diagnosis, prognosis, and treatment of ALL. One-third of all cases of ALL involve specific translocations, and t(4;11) corresponds to a poor prognosis group most frequent in infants less than 16 months of age with a median survival of less than 1 year (Kocova et al., 1985, Cancer Genetics and Cytogenetics 16, 21-32). Translocations involving region 4q21 have also been reported in T-lymphomas (Levine, E. G. et al., 1986, Cancer Res, 46, 6481-6488) and a case of acute myeloblastic leukemia (AML) (Selypes, A. et al., 1987, Human Genet, 76, 106-108). This region also contains the genes for a dental dysgenesis syndrome and the 'piebald trait', an inherited disorder resulting in patchy skin pigmentation due to deficient melanoblast migration and differentiation (Hoo, J. J., et al., 1986, Human Genet., 73, 230-231).

Linkage studies between AR and the genetic disorders localized to chromosome 4q13-4q21 will allow us to determine the significance of this co-localization. Current cytogenetic analysis suggests region 4q21 contains genes involved in lymphocytic differentiation. Ultimately these associations may suggest further biological activities or applications for this growth regulatory molecule.

9.3. Genomic Cloning

Southern blot analysis (section 9.1 supra) of MCF-7 DNA digested with HindIII, EcoRI or BamHI showed single bands of 12 kb, 8 kb, and 20 kb, respectively, when hybridized with an 830 bp probe ($^{32}$P-labeled PvuII/BsmI digested pAR1) containing the 5' portion of the AR gene, suggesting that AR is a single copy gene. A 170 bp probe (AR 170, BsmI-PvuII) from the 3' end of mature AR, including the transmembrane and cytoplasmic domain coding regions, hybridized to the same HindIII, EcoRI, and BamHI fragments and also to an additional 7.5 kb HindIII fragment, implying that the majority of the AR coding region is split between two HindIII fragments of 12 and 6.5 kb. Identical banding was seen by Southern analysis of digests from human placenta, brain, melanoma (SK-MEL 28), breast cancer (HTB36), epidermoid carcinoma (A431), and lung cancer DNA and suggests that the AR gene has not experienced any gross rearrangements or amplifications.

Applicants elected to clone the two HindIII fragments from MCF-7 DNA since they were likely to contain most if not all of the AR gene and its flanking sequences. HindIII digested MCF-7 DNA was size-fractionated and the appropriate fractions were ligated into λL47.1. Of numerous positives, two clones, λARH12 and λARH6, were selected for more detailed characterization. The 12 and 6.4 kb inserts were subcloned into pEMBL18 and mapped for several restriction sites. Using exact oligonucleotide primers and direct sequencing of various smaller subclones, the sequence of all exons and their intron junctions were determined, revealing no discrepancies with the cDNA sequence.

9.4 Characterization of the Ar 5' Regulatory Region

Genomic cloning of AR led to the isolation of 6.5 kb of 5' flanking sequence contained in the 12 kb HindIII fragment. The 688 bp fragment from the first EcoRI site 5' of exon 1 to the SmaI site in exon 1 (position 40 in cDNA) was subcloned and sequenced on both strands. This data is shown in FIG. 17.

Primer extension was performed on MCF-7 RNA with 2 separate oligonucleotides from exon 1. A major transcriptional start site, confirmed by both oligonucleotides, was localized to 1 bp 5' to the longest cDNA clone. Two minor sites were seen at position +1 and +2 in the cDNA sequence, confirming that many of the cDNA clones were almost full length. In order to functionally confirm the regulatory region of the AR gene, we constructed a chimeric gene (pXARE1CAT) containing the 688 bp EcoRI to SmaI AR 5'flanking region (sequences 648 to +40, with +1 being the major transcriptional start site) driving expression of a promotorless chloramphenicol acetyltransferase (CAT) gene. This construct was able to stimulate transcription of the CAT gene when introduced transiently into MCF-7 cells, and activity was stimulated 6-7 fold by the addition of TPA. This confirms both structurally and functionally that we have cloned the 5' end of the AR gene. We then constructed a series of 5' CAT deletion mutants containing AR sequences −539 to +40 (E1a), −387 to +40 (E1b), −277 to +40 (E1c), −148 to +40 (E1d), −77 to +40 (E1e), −79 to +40 (E1g), or +19 to +40 bp (E1h) in the same vector. Basal activity was lost when deleting beyond portion −77, i.e. E1h showed no measurable activity, and all of these constructs exhibited 3.5-7 fold enhanced expression in response to 40 hour treatment with 100 ng/ml TPA. These constructs can also be used in transient assays to assess the effects of any morphogens, mitogens, growth factors, drugs, or crude fermentation extracts on the regulation of AR expression, enabling one to identify new therapeutic agents.

Nuclear run-off experiments show 3-5 fold increased transcription of AR in response to TPA, suggesting increased promoter activity is at least partially responsible for the TPA induction of AR. Northern analysis of MCF-7 cells treated with TPA in the presence or absence of actinomycin D identifies AR as a relatively stable RNA, with a half-life greater than 4 hours. The induction of AR expression in response to TPA is therefore mutlifaceted, involving increased transcription of a rather stable mRNA.

9.5. Intron/Exon Organization of the Ar Gene, Ar Protein Domains, Evolutionary and Functional Implications The complete human Amphiregulin genomic sequence is depicted in FIG. 17 and the relationship between exons and the protein domains of the AR molecule is represented schematically in FIG. 18.

Primer extension analysis of AR mRNA and studies using chimeric AR/CAT promoter (CAT=Chloramphenicol acetyltransferase, a marker gene) constructs localize a functional promoter within the 64 bp 5' to the end of the longest cDNA clone. Moreover, there is a consensus TATA box 29 bp upstream of the 5'-end of the cDNA sequence. The 3' end of the gene is preceded by a consensus polyadenylation signal sequence, 64 nucleotides from the poly(A) tail in the cDNA. The primary transcript of the AR gene is approximately 10.2 kb.

Six exons encode the human AR precursor and span 10.2 kb of genomic DNA. The AR exons range from 112 to 270 bp in length and are interrupted by introns of between 1.25 kb and 2.1 kb. The five introns of AR interrupt the coding sequence such that many of the protein domains are products of a single exon. Exon 1 encodes the 5' untranslated and signal peptide domains, exon 2 encodes the N-terminal precursor, exon 5 contains the cytoplasmic region, and exon 6 represents the 3' untranslated region. Together, exons 3 and 4 encode the mature AR protein, including both the hydrophilic and EGF-like sequences, as well as the putative transmembrane domain. The junction between exons 3 and 4 occurs between the second and third loops of the EGF-like region.

When the exon junctions are overlayed on an alignment of the amino acid sequences of AR, EGF, and TGF-α, it is evident that all of these proteins are encoded by two exons and that the interrupting intron is located in the same position. Moreover, the 3' exon of each also encodes the transmembrane domain of the corresponding precursor proteins. In contrast, the EGF-like region is contained on a single exon in all other mammalian EGF homologs for which the exon structure has been determined: including the nine EGF-like repeats in the EGF precursor; (Gray, 1983, Nature, 303, 722-725); the three in LDL receptor (Yamamoto, 1984, Cel, 39, 27-38); and the one each in rat fibronectin (Patel, 1987, Embo J., 6, 2565-2572) and human coagulation factor XII (Cool, 1987, J. Biol. Chem., 262, 13662-13673). Invertebrate homologs such as the Drosophilia Notch gene and lin-12 from C. elegans also contain multiple EGF-like repeats (Kidd, 1986, Molec. Cell. Biol., 6, 3094-3108; Greenwald, 1985, Cell, 43, 583-590). Unlike the mammalian genes, most of the EGF-like repeats in Notch are contained in a single coding region with only four of the thirty-six motifs being split by intervening sequences. Notably, two of these four exhibit stronger alignment with AR than with the Notch repeat consensus and one is even interrupted by an intron at the same CXC sequence as EGF, TGF-α, and AR. The nematode lin-12 gene contains at least eleven EGF-like units, nine of which are contained on the first exon and the remaining two are on separate exons with the intact EGF-like unit flanked by introns.

Differences in the structure of the exons encoding the EGF-like repeats from various organisms suggest they may have different origins. One group contains the EGF-like motif bounded by introns and the other group, of which AR is a member, has an interrupted motif. The sequence similarity between the two groups could be the result of convergent evolution or intron insertion after their divergence from a common ancestral gene.

The intron location within the same CXC sequence of EGF, TGF-α, AR and one of the Notch repeats suggests a common origin, but closer examination reveals different intron phasing. Intron phasing refers to whether the intron interrupts the reading frame after the first (I) second (II) or third (O) nucleotide of a codon. Phasing is believed to be of evolutionary importance inasmuch as it may permit the shuffling of functional domain containing exons among different proteins. EGF and TGF-α have a phase II intron in the EGF-like unit, whereas AR and Notch have phase I introns. A similar shift of one nucleotide is seen in the penultimate intron within the protease domain of complement factor B and elastase (Cambell, 1983, PNAS, 80, 4464; Swift, 1984, J. Biol. Chem. 259, 14271). The non-random positions of these introns may imply that a specific intron insertion sequence is present in these genes. Alternatively, there may have been selective pressure to divide the coding region at this site. Comparison of sequences at the exon-intron junction site within the EGF-like unit for human EGF, TGF-α, AR and the first Notch repeat, reveal no direct repeats as often seen with transposable elements. However, all four have the sequence, 'gtaagt' bordering the junction. This sequence may play some role in the origin or splicing of this intron.

The viral EGF homologs contain no introns; however, an alignment between VGF, EGF, TGF-α, and AR shows homology extending through the transmembrane domain whereas the growth factors from myxoma and shope viruses terminate before this hydrophobic region. Recent studies provide evidence that the TGF-α precursor is synthesized as a transmembrane protein and differential proteolytic cleavage results in secretion of larger forms which may be cell type specific (Teixido, 1987, Nature, 326, 883–885).

Other EGF homologs which contain transmembrane domains include the clotting factors, LDL, and the homeotic genes Notch and lin-12, though none are adjacent to an EGF-like repeat. The presence of the EGF motif in several membrane bound precursors suggests that in some instances they may be processed as a secreted growth factor or may remain associated with the membrane and may play a role in intercellular and/or intracellular communication.

Some of the AR homologs include invertebrate homeotic genes. Homeotic gene products are involved in regulation of cell development. For example, the Notch gene product mediates the correct progression of an ectodermal cell into a neuroblast or a dermoblast. In Notch mutants, all these cells become neuronal and the offspring, all brain and no skin, die. A homeotic gene may function in an autocrine fashion to establish or maintain a determined state in cells expressing the gene product and may be involved with regulating such states in adjacent cells via cell-cell interactions. Whether AR also functions to regulate the developmental state of certain cell types should be investigated.

9.6. Processing of Mature Amphiregulin

Characterization of AR cDNA revealed that the 78 and 84 amino acid forms of AR are synthesized as the middle portion of a 252 amino acid transmembrane precursor (Section 8.2, supra). The sites for proteolytic cleavage of the AR precursor which would result in the release of mature AR do not fit the cleavage sites of any known protease. On the N-terminal end the sites are Asp-Asp/Ser-Val and Glu-Gln/Val-Val while the C-terminal site is Glu-Lys/Ser-Met. The two forms of AR appear to be the result of alternate proteolytic processing from a common precursor since all cDNA and genomic clones revealed the same sequence in this region. Interestingly, an intron lies between the two N-terminal cleavage sites and it is possible that "intron sliding: might also account for these differences.

MCF-7 cells produce 80% of their AR in the larger 84 amino acid form whereas the choriocarcinoma cell line HTB-36 produces 80% of its AR in the smaller 78 amino acid form. To determine if this difference is linked to alterations at the DNA level, we utilized the polymerase chain reaction technique (Scharf, 1986, Science, 233, 1076-1078) to isolate AR exon 3 from MCF-7 cells and HTB-36 cells, a line which constitutively produces high levels of AR mRNA. An AR intron specific "sense" oligonucleotide and an "antisense" oligonucleotide from the coding region of exon 3 were used to specifically amplify the intervening 220 bp fragment of the AR gene from both DNA sources. Direct sequence analysis showed no discrepancies in either the intron-exon junction or in the exon 3 coding sequence between these two human DNA sources, further suggesting that the two forms of AR result from alternate proteolytic cleavage of the precursor.

9.7. Structural Comparison of Ar and Egf-Like Growth Factors

AR clearly shows sequence homology with other EGF-like proteins, with the conservation of 6 cysteines involved in 3 disulfide bonds which define the secondary structure of the mature growth factors. Previous (computer assisted) comparisons of amino acid sequences have led to the categorization of EGF-like motifs into two distinct groups: growth factors and blood coagulation factors (see FIG. 13). We have selected two sequence patterns for comparison with AR and other known DNA or protein sequences. Selection was based on the apparent ability of these sequences to distinguish between the two groups of proteins and because very few gaps were needed for optimal alignments. The exact sequences are shown in Table 1. The first region corresponds to the first 11 amino acids of the second loop of EGF and the second corresponds to the third cysteine loop of EGF. Four representatives from each group of growth factor and blood coagulation factors were selected for generation of consensus sequences based on their well established functional and structural homology. Human sequences were selected whenever possible since we ultimately wanted to compare them with human AR. The growth factors include: human EGF, TGF-α, VGF and Shope growth factor, and the coagulation factors include: human factor IX, X, XII, and protein C. AR was also scored against the database for both of these homology blocks. The consensus sequence was weighted based on the frequency that a residue appeared at a given position.

Structure-function analysis of various TGF-α, VGF, and EGF derivatives have recently led to the identification of several residues which are necessary for the biological activity of these growth factors. Recombinant proteins, synthetic peptides, site-specific chemical derivatives and proteolytic degradation have all been useful for generating altered molecules. Some generalizations include (positions are relative to the alignment in FIG. 15): the 6 cysteines (position 1, 19, 15, 26, 28 and 37) and their disulfide loops (1–15, 9–26, 28–37) are required for biological activity, N-terminal extensions have little effect on activity, an aromatic residue (F, Y) is required at position 8, a nonconservative change of $Y^{32}$, $D^{41}$, or $L^{42}$ results in loss of activity and/or dramatic loss in receptor binding or autophosphorylation.

AR fits all but the last two criteria defining residues necessary for EGF receptor binding and/or mitogenic activity. Mature AR truncates just prior to $D^{41}$ and completely lacks this and the "crucial" leucine 42, yet it still competes for EGF receptor binding and substitutes for EGF in some mitogenic assays. However, these differences may be responsible for the nonsaturable receptor binding kinetics and its marked functional differences from EGF in certain assays such as TGF-$\beta$ synergism, the differential effect on selected A431 subclones, cross-linking, phosphorylation assays, and its ability to bind DNA. The extremely hydrophilic stretch at the N-terminus of mature AR may also impart some of these differences in receptor binding, or biologic activity.

9.8. Ar Subcategory of Egf Superfamily

We calculated a matrix of evolutionary distances based on the alignment in FIG. 13 and computer analysis based on Table I (p. 25). This matrix was used to derive a dendrogram for the EGF superfamily. The search requires the presence of the cysteines and adds a point for each residue that matches the weighted consensus sequence. This evolutionary tree predicts that AR falls within a new subcategory of the EGF-like growth factors, based on both structural and functional homology. Such a model predicts that other members of this growth factor family may exist and that they can be identified by homology with the above sequence patterns based on three criteria: a combined score with the two growth factor regions of more than 20, a combined coagulation factor region score of less than 20, and a combined AR region score of more than 20. All new molecules fitting these criteria would be expected to also have some functional homology with EGF, TGF-$\alpha$, VGF or AR. Molecules with combined AR region score of more than 40 would be classified as a member of the AR family within the EGF superfamily and would be within the scope of the invention.

10. EXAMPLE: BACTERIAL EXPRESSION OF AMPHIREGULIN

10.1 Materials and Methods

10.1.1. Plasmid Construction

Plasmid pARD1. Plasmid pARD1 contains the 1.4 kb EcoRI cDNA fragment (pAR1) in pEMBL18 with a T to C change at nucleotide position 532 in the cDNA corresponding to the valine-valine sequence at the amino-terminus of the mature AR. This base change was accomplished by site directed mutagensis and confirmed by sequence analysis. The construct allows access to the junction between the AR amino-terminal precursor domain and the hydrophilic region by creating a DdeI site (CTAAG).

Plasmid pARSTOP. Plasmid pARSTOP is an intermediate construct used in the preparation of an AR secretion vector. pARD1 was digested with SspI and XbaI and the 515 bp fragment encoding the carboxy-terminal 9 amino acids of mature AR, the transmembrane and cytoplasmic domains, and the 3' untranslated region was isolated. The 4.7 kb (SspI-XbaI) fragment containing the remaining amino-terminal portion of AR cDNA was gel purified and ligated with kinased, annealed, complimentary oligonucleotides ARSTOP1 and ARSTOP2 (depicted below). These oligonucleotides have a 5' blunt end compatible with an SspI site followed by a sequence encoding the carboxy-terminal 9 amino acids of the mature AR sequence, a TAA stop codon and EcoRV and XbaI sites.

```
                Y F G E R C G E K * EcoRV/XbaI

ARSTOP    5'   ATTTCGGTGAACGGTGTGGGGAAAAGTAAGATATCT
ARSTOP    3'   TAAAGCCACTTGCCACACCCCTTTTCATTCTATAGAGTC
```

Plasmid pbAR. Plasmid pbAR contains a promoterless TGF-$\beta$ leader attached to the mature 78 amino acid form of AR. It was constructed by ligation of the oligonucleotides bLARN3 and bLARN4 with the 240 bp DdeI to XbaI fragment from pARSTOP into EcoRI/XbaI digested pEMBL18. bLARN3 and bLARN4 are complimentary, creating a 5'EcoRI and a 3'DdeI overhang and a single internal NaeI site compatible with the one near the carboxy-terminal end of the TGF-$\beta$ leader sequence. Ligation will destroy the DdeI site and regenerate the correct amino acid sequence valine-valine at the amino-terminus of mature AR.

```
              SstII
              A  G  V  V  K  P  P  Q  N  K  T  E  S  E
PHIL1   5'   GGGAGTAGTTAAGCCGCCCCAAAACAAGACGGAAAGTGA
PHIL2   3'   CGCCCTCATCAATTCGGCGGGGTTTTGTTCTGCCTTTCACT

N  T  S  D  K  P  K  R  K  K  K  G  G
PHIL1   5'   AAATACTTCAGATAAACCCAAAAGAAAGAAAAAGGGAGG
PHIL2   3'   TTTATGAAGTCTATTTGGGTTTTCTTTCTTTTTCCCTCC

EcoRI
              K  N  G  K  N  R  R  N  R  K  K  K  N
PHIL1   5'   CAAAAATGGAAAAAATCGAAGAAACAGAAGAAGAAG
PHIL2   3'   GTTTTTACCTTTTTTAGCTTCTTTGTCTTTCTTCTTAA
```

Plasmid pDCHBAR1. Plasmid pDCHBAR1 is a mammalian expression vector (FIG. 19) designed for secretion of the processed, mature 78 amino acid form of AR. It contains the TGF-$\beta$ leader/mature AR sequence from pbAR driven by the CMV/HIV promoter, flanked by an SV40 polyadenylation signal. The vector also contains SV2dhfr, in the same transcriptional orientation. PSVDR/bOM was digested with NaeI and XbaI, and the 6 kb vector was purified away from the excised OncoM coding sequence. pbAR was also digested with NaeI and XbaI, and the 260 bp fragment encoding the carboxy-terminal 5 amino acids of TGF-$\beta$ signal sequence, and the 78 amino acid mature AR sequence followed by a termination codon and EcoRV and XbaI sites. Junctions were verified by sequence analysis.

Plasmid pDCHBPHILE. Plasmid pDCHBPHILE is a mammalian expression vector designed for secretion of a chimeric AR/EGF protein. The plasmid is also configured to facilitate future fusion constructs between the AR hydrophilic domain and other growth factors. This construct was created by ligation of the 6.5 kb SstII/XbaI digest pDCHBARI vector fragment, the 175 bp EcoRI/XbaI fragment containing the synthetic human EGF gene, and oligonucleotides PHIL1 and PHIL2. These oligonucleotides are complimentary with 5' SstII and 3' EcoRI extensions and encode the last residue of the TGF-$\beta$ signal sequence and the entire AR hydrophilic domain. pDCHBAR1 provides the CMV/HIV promoter, all but the last amino acid of the TGF-$\beta$ signal sequence, and the SV40 polyadenylation sequence. The EGF fragment was obtained from Dr. Timothy M. Rose (Oncogen), and includes convenient sites for future manipulation.

10.1.2. Preparation of pTAC Vector

Plasmid TacPak/EGF was obtained from Dr. Timothy M. Rose (Oncogen) and is composed of the following units: trp-lac hybrid promoter and Cro gene Shine-Delgarno sequence isolated as a BglII/BamHI fragment from expression vector p135-1 which in turn was derived from pDR540 (Pharmacia); alkaline phosphatase signal sequence derived from synthetic oligonucleotides TacPak1 and TacPak2 (Dr. Rose, Oncogen); synthetic EGF sequence shuttled from plasmid pBM22/PAK-/EGF; transcriptional termination region; pBR322 backbone with the neomycin resistance gene all derived from plasmid p135-1. TacPak/EGF was digested with BamHI, 2-base filled with dATP and dGTP to create a site compatible with the 2-base filled SalI, and then digested with PvuI. This digestion removes the synthetic EGF gene and the majority of the alkaline phosphatase signal sequence, but leaves the Tac promoter, and Shine-Delgarno sequences and initiating ATG intact. The 2.8 kb fragment was gel purified.

10.1.3. Preparation of Modified Amphiregulin cDNA

Plasmid pARSTOP was digested with SalI, 2-base filled with TTP and dCTP to create a site compatible with a BamHI 2-base filed (dATP, dGTP) extension and then digested with DdeI and BglI. The later digest was necessary to remove comigrating DNA from the desired 242 bp fragment, which encodes the short form of mature AR beginning with VKPP and ending with CGEK, followed by a synthetically introduced stop codon. The 243 bp fragment was gel purified.

10.1.4. Preparation of Alkpar1 and Alkpar2 Synthetic Oligonucleotides

Complementary synthetic oligonucleotides ALKPAR1 and ALKPAR2 were designed with a 5' PvuI overhang compatible with TacPak/EGF PvuI/BamHI-partial filled fragment and a 3' DdeI extension comparible with the pARSTOP DdeI/SalI-partial filled fragment. They were synthesized on an Applied Biosystems Oligonucleotide Synthesizer and purified from an acrylamide gel. Phosphates were added to the oligonucleotides with T4 Kinase, and equimolar amounts annealed with slow cooling after heat denaturation.

```
                 PvuI                                           DdeI
             I    A   L   A   L   L   P   L   L   F   T   P   V   T   K   A   V   V
ALKPAR1  5'       CGCCCTCGCACTTCTCCCACTGCTGTTCACTCCAGTGACAAAAGCTGTAG              3'
ALKPAR2  3'  TAGCGGGAGCGTGAAGAGGGTGACGACAAGTGAGGTCACTGTTTTCGACATCAAT              5'
```

10.1.5. Ligation and Isolation of pTacAPAR1

The 243 bp DdeI to SalI-partial filled AR fragment, the 2.8 kb PvuI/BamHI-partial filled TacPak/EGF vector fragment; and kinased, annealed ALKPAR1+2 oligonucleotides were ligated using DNA ligase, transformed into competent E. coli JM109 cells and selected on LB/neomycin plates. The correct construct was confirmed with restriction digests and DNA sequencing. The sequence of pTacAPAR is depicted in FIG. 20.

10.1.6. Preparation of Chimeric Ar Hydrophilic Domain/Egf Gene Fragment

Plasmid pDCHBPHILE was digested with SstII and XbaI to generate the 286 bp fragment, which encodes the last 2 residues of the TGF-$\beta$ signal sequence (AG), 37 residues from the hydrophilic domain of AR (VVKP ... RKKK) and the 53 residue synthetic sequence of mature human EGF sequence (NSDS ... WELR). The 286 bp fragment was gel purified.

10.1.7. Preparation of Aparegf1 and Aparegf2 Synthetic Oligonucleotides

Complemenary synthetic oligonucleotides APAREGF1 and APAREGF2 were designed with a 5' PvuI overhang compatible with pTacAPAR1 PvuI/XbaI fragmant and a 3' SstII extension compatible with the pDCHBPHILE SstII/XbaI fragment. Oligonucleotides were synthesized on an Applied Biosystems Oligonucleotide Synthesizer and purified from an acrylamide gel. Phosphates were added to the oligonucleotides with T4 Kinase, and equimolar amounts annealed with slow cooling after heat denaturation.

```
                  PvuI                                          SstII
              I    A   L   A   L   L   P   L   L   F   T   P   V   T   K
APAREGF1  5'       CGCCCTCGCACTTCTCCCACTGCTGTTCACTCCAGTGACACC              3'
APAREGF2  3'  TAGCGGGAGCGTGAAGAGGGTGACGACAAGTGAGGTCACTGTGGCG              5'
```

Fragment

10.1.8. Ligation and Isolation of pTACAPHILE

The 286 bp SstII/XbaI fragment encoding the hydrophilic domain of AR attached to mature EGF sequence, the 2.8 kb PvuI/XbaI pTacAPAR1 vector fragment and kinased, annealed APAREGF1+2 oligonucleotides were ligated using DNA ligase, transformed into competent *E. coli* JM109 and selected on LB/neomycin plates. The correct construct was confirmed with restriction digests and DNA sequencing. The nucleotide sequence of pTacAPHILE is shown in FIG. 21. The expected translation product should be cleaved between the dipeptide Ala-Gly just following the alkaline phosphatase signal sequence, thereby adding one additional residue (glycine) to the AR hydrophilic domain. Nucleotide residues which differ from the normal human sequence are displayed in bold type (FIG. 20).

10.1.9. Purification of Recombinant Amphiregulin

Plasmids pTacAPAR1 and pTacAPHILE were transformed into competent *E. coli* JM109 and grown to confluency in 10 ml LB at 37° C. to an $A_{600}$ of 0.7. Cultures were then induced with 100 uM IPTG and allowed to grow for 24-72 hours. The cultures were centrifuged twice at 5000 rpm, 15 min. each, the pellet saved and the purification continued with the supernatant. Samples were concentrated 10 fold on an Amicon ultrafiltration apparatus with YM5 membranes (5000 MW cutoff) The concentrate was diluted with 5 volumes MilliQ water and reconstituted to one-tenth the original culture volume. Glacial acetic acid was added to 1 M, and the samples placed at 4° C. for 2-24 hours. The samples were centrifuged at 19,000 rpm, 20 min., 4° C. in Oakridge tubes in the SS34 rotor, the pellet extracted with 20 ml 1 M acetic acid and the supernatants pooled. The cleared supernatants were then dialyzed against 0.1 M acetic acid for 2 days, lyophilized and stored at −20° C.

Cell pellets and crude dried supernatants were assayed by immunoblotting and growth inhibitory assays (GIAs) for AR protein. The cell pellet from 50 ul confluent culture or 100-200 ul dried supernatant was run on a 16% Tricine polyacrylamide gel, stained with Fast Green and transferred to nitrocellulose. Western blots were performed as described in section 7.1.6. supra.

10.2. Results and Discussion

Cell pellets from transformants carrying pTacA-PAR1 showed abundant amounts of immunoreactive protein migrating at 10 kD as well as some degradation products and probable dimers. The supernatants had approximately 100-200 ng/ml of secreted immunoreactive AR. GIA on the supernatents measured activity at approximately 150 ng/ml AR on the A431-A3 indicator cell line, as compared with purified native AR standards. Large amounts of immunoreactive protein were produced in this system, most of which remained aggregated within the cell. Assays on periplasmic preparations and supernatants showed secretion of active protein after growth for 2-3 days.

pTacAPHILE provides a convenient means by which to attach the hydrophilic domain of AR onto the N-terminus of any cloned gene. This region might impart altered binding characteristics to the ligand's normal receptor, function as a nuclear localization sequence, bind to DNA, or permit transport across lipid or other membranes normally impermeable to the attached factor.

11. Deposit of Microorganisms

The following microorganisms have been deposited with the Agricultural Research Culture Collection, Northern Regional Research Center (NRRL) and have been assigned the following accession numbers:

| Microorganism | Plasmid | Accession No. |
| --- | --- | --- |
| *Escherichia coli* HB101 | pAR1 | |
| *Escherichia coli* SCS-1 | pARH12 | |
| *Escherichia coli* SCS-1 | pARH6 | |
| *Escherichia coli* JM109 | pTacAPAR1 | |
| *Escherichia coli* JM109 | pTacAPHILE | |

The present invention is not to be limited in scope by the cell lines deposited or the embodiments disclosed herein which are intended as single illustrations of one aspect of the invention and any which are functionally equivalent are within the scope of the invention. Indeed, various modifications of the invention, in addition to those shown and described herein, will become apparent to those skilled in the art from the foregoing description. Such modifications are intended to fall within the scope of the appended claims.

It is also to be understood that all base pair and amino acid residue numbers and sizes given for nucleotides and peptides are approximate and used for the purposes of description.

What is claimed is:

1. A protein having an amino acid sequence:

```
1           10            20
VVKPPQNKTE SENTSDKPKR KKKGGKNGK 30          40          50
NR R NRKKKNPC NAEFQNFCIH GECKYI 60          70       78
       EHLE AVTCKCQQEY FGERCGEK
```

2. The protein of claim 1 having a pI in the range of about 7.6 to 8.0.
3. A glycosylated protein of claim 1.
4. An un-glycosylated protein of claim 1.
5. A protein having an amino acid sequence:

```
1               10              20
S V R V E Q V V K P  P Q N K T E S E N T  S D K P K R K K K 30              40              50
G G K N  G  K N R  R  N R  K K K N P C N A E F  Q N F C I 60              70          80      84
H G E C K Y I E H L E A V T C  K C Q Q E Y F G E R  C G E K
```

6. The protein of claim 5 having a pI in the range of about 7.6 to 8.0.
7. A glycosylated protein of claim 5.
8. An un-glycosylated protein of claim 5.
9. The protein of claim 1 or a peptide fragment thereof that inhibits the growth of human epidermoid carcinoma of vulva A431 cells, human adenocarcinoma of breast HTB 132 cells, human epidermoid carcinoma of cervix CRL 1550 cells, human papillary adenoma of ovary HTB 75 cells, human teratocarcinoma of ovary HTB 1572 cells, or human adenocarcinoma of breast HTB 26 cells.

10. The protein of claim 1 or a peptide fragment thereof that stimulates the growth of human foreskin fibroblasts cultured in vitro.

11. The protein of claim 10 in which the human foreskin fibroblasts comprise Sadamoto or Goodwin cell lines.

12. The protein of claim 1 or a peptide fragment thereof that inhibits the growth of human epidermoid carcinoma of vulva A431 cells, human adenocarcinoma of breast HTB 132 cells, human epidermoid carcinoma of cervix CRL 1550 cells, human papillary adenoma of ovary HTB 75 cells, human teratocarcinoma of ovary HTB 1572 cells, or human adenocarcinoma of breast HTB 26 cells and stimulates the growth of human denocarcinoma of ovary HTB 77 cells, Sadamoto human foreskin fibroblast cells, Goodwin human foreskin fibroblast cells, African green monkey kidney BSC-1 cells, or rat kidney SA6 cells.

13. The protein of claim 5 or a peptide fragment thereof that inhibits the growth of human epidermoid carcinoma of vulva A431 cells, human adenocarcinoma of breast HTB 132 cells, human epidermoid carcinoma of cervix CRL 1550 cells, human papillary adenoma of ovary HTB 75 cells, human teratocarcinoma of ovary HTB 1572 cells, or human adenocarcinoma of breast HTB 26 cells.

14. The protein of claim 5 or a peptide fragment thereof that stimulates the growth of human foreskin fibroblasts cultured in vitro.

15. The protein of claim 14 in which the human foreskin fibroblasts comprise Sadamoto or Goodwin cell lines.

16. The protein of claim 5 or a peptide fragment thereof that inhibits the growth of human epidermoid carcinoma of vulva A431 cells, human adenocarcinoma of breast HTB 132 cells, human epidermoid carcinoma of cervix CRL 1550 cells, human papillary adenoma of ovary HTB 75 cells, human teratocarcinoma of ovary HTB 1572 cells, or human adenocarcinoma of breast HTB 26 cells and stimulates the growth of human adenocarcinoma of ovary HTB 77 cells, Sadamoto human foreskin fibroblast cells, Goodwin human foreskin fibroblast cells, African green monkey kidney BSC-1 cells, or rat kidney SA6 cells.

17. An Amphiregulin precursor corresponding to the amino acid sequence depicted in FIG. 16 from amino acid residue number 1 to amino acid residue number 252.

18. The protein of claim 4 having a molecular weight of about 8,500 daltons.

19. The protein of claim 3 having a molecular weight in the range of about 8,500 to 25,000 daltons.

20. The protein of claim 8 having a molecular weight of about 9,100 daltons.

21. The protein of claim 7 having a molecular weight in the range of about 9,100 to 25,000 daltons.

22. The protein of claim 1 or a peptide fragment thereof that stimulates the growth of human adenocarcinoma of ovary HTB 77 cells, Sadamoto human foreskin fibroblast cells, Goodwin human foreskin fibroblast cells, African green monkey kidney BSC-1 cells, or rat kidney SA6 cells.

23. The protein of claim 5 or a peptide fragment thereof that stimulates the growth of human adenocarcinoma of ovary HTB 77 cells, Sadamoto human foreskin fibroblast cells, Goodwin human foreskin fibroblast cells, African green monkey kidney BSC-1 cells, or rat kidney SA6 cells.

* * * * *

UNITED STATES PATENT AND TRADEMARK OFFICE
CERTIFICATE OF CORRECTION

PATENT NO. : 5,115,096
DATED : May 19, 1992
INVENTOR(S) : Shoyab et al

It is certified that error appears in the above-indentified patent and that said Letters Patent is hereby corrected as shown below:

On the cover page of the patent, in the amino acid sequence formula, the first seven amino acid residues reading "VVKPPQD$^1$" should read -- VVKPPQN$^1$ --.

In the drawings, Sheet 24, Fig. 12A, the first seven amino acid residues reading "VVKPPQD$^1$" should read -- VVKPPQN$^1$ --; and in Fig. 12B, the thirteenth amino acid residue reading "D" should read "N".

Column 3, lines 60-61, "mature AR and (B) truncated AR" should read -- truncated AR and (B) mature AR --.
Column 14, line 47, "chmotripsin" should read -- chymotrypsin --.
Column 18, line 63, "J. Biol. Chem. 245" should read -- J. Biol. Chem 254 --.
Column 20, line 46, "ml min" should read -- ml/min --.
Column 22, line 68, "min ml" should read -- ml/min --.
Column 29, line 24, "Section" should read -- Section 6.4.2. --.
Column 41, line 13, "100 µl 1 0.25" should read -- 100 µl 0.25 --.
Column 42, line 11, "oncogere" should read -- oncogene --.

UNITED STATES PATENT AND TRADEMARK OFFICE
CERTIFICATE OF CORRECTION

PATENT NO. : 5,115,096
DATED : May 19, 1992
INVENTOR(S) : Shoyab et al

It is certified that error appears in the above-indentified patent and that said Letters Patent is hereby corrected as shown below:

Column 49, line 66, "filed" should read -- filled --.
Column 52, lines 12-16, the table listing the microorganism deposits should read as follows:

| Microorganism | Plasmid | Accession No. |
|---|---|---|
| *Escherichia coli* HB101 | pAR1 | NRRL B-18438 |
| *Escherichia coli* HB101 | pARH12 | NRRL B-18439 |
| *Escherichia coli* HB101 | pARH6 | NRRL B-18440 |
| *Escherichia coli* JM109 | pTacAPAR1 | NRRL B-18441 |
| *Escherichia coli* JM109 | pTacAPHILE | NRRL B-18442 |

Signed and Sealed this

Twenty-third Day of May, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,115,096
DATED : May 19, 1992
INVENTOR(S) : Shoyab, et. al.

It is certified that error appears in the above-indentified patent and that said Letters Patent is hereby corrected as shown below:

In the drawings, Sheet 29, Fig. 16, the amino acid residue at position 172 reading "A" should read -- C --.

Signed and Sealed this

Second Day of July, 1996

*Attest:*

BRUCE LEHMAN

*Attesting Officer*   *Commissioner of Patents and Trademarks*